US009290820B2

(12) United States Patent
Lee et al.

(10) Patent No.: US 9,290,820 B2
(45) Date of Patent: Mar. 22, 2016

(54) METHODS FOR DETECTION OF PARVOVIRUS B19

(71) Applicant: GRIFOLS THERAPEUTICS INC., Research Triangle Park, NC (US)

(72) Inventors: Douglas C. Lee, Apex, NC (US); Todd M. Gierman, Cary, NC (US); Chris Glenn, Holly Springs, NC (US); Burton Beams, Raleigh, NC (US); Brett Buno, Durham, NC (US); Lori Rinckel, Clayton, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 0 days.

(21) Appl. No.: 14/053,245

(22) Filed: Oct. 14, 2013

(65) Prior Publication Data
US 2014/0106337 A1    Apr. 17, 2014

Related U.S. Application Data

(63) Continuation of application No. 12/523,309, filed as application No. PCT/US2008/051083 on Jan. 15, 2008, now abandoned.

(60) Provisional application No. 60/885,074, filed on Jan. 16, 2007, provisional application No. 60/942,762, filed on Jun. 8, 2007.

(51) Int. Cl.
*C12Q 1/70*    (2006.01)
*C12N 7/00*    (2006.01)

(52) U.S. Cl.
CPC  *C12Q 1/701* (2013.01); *C12N 7/00* (2013.01); *C12N 2750/14221* (2013.01)

(58) Field of Classification Search
None
See application file for complete search history.

(56) References Cited

U.S. PATENT DOCUMENTS

| | | |
|---|---|---|
| 6,936,442 B2 | 8/2005 | Pichuantes et al. |
| 7,291,452 B1 | 11/2007 | Nguyen et al. |
| 2003/0124578 A1 | 7/2003 | Brentano et al. |
| 2005/0221300 A1 | 10/2005 | Pichuantes et al. |
| 2006/0008469 A1 | 1/2006 | Brown et al. |
| 2006/0057643 A1 | 3/2006 | McCarthy et al. |

FOREIGN PATENT DOCUMENTS

WO    WO-2005/075686 A1    8/2005

OTHER PUBLICATIONS

E. D. Heegaard, et al., "Human Parvovirus B19," Clinical Microbiology Reviews, Jul. 2002, vol. 15, No. 3, pp. 485-505.
Q. Nguyen, et al., "Novel Human Erythrovirus Associated with Transient Aplastic Anemia," Journal of Clinical Microbiology, Aug. 1999, vol. 37, No. 8, pp. 2483-2487.
Shade et al., GenBank Accession No. M13178.1, May 17, 1995.
Nguyen et al., GenBank Accession No. Ay064476.1, Mar. 4, 2004.
Nguyen, NCBI Reference Sequence: NC_004295.1, Oct. 26, 2006.
Hicks et al., GenBank Accession No. Z68146.1, Sep. 9, 2004.
Q. T. Nguyen, et al., "Identification and Characterization of a second novel human erythrovirus variant, A6," Virology, vol. 301, No. 2, Sep. 30, 2002, pp. 374-380.

*Primary Examiner* — Diana B Johannsen
(74) *Attorney, Agent, or Firm* — Womble Carlyle Sandridge & Rice, LLP; Carl B. Massey, Jr.

(57)  ABSTRACT

Nucleic acid molecules derived from sequences of novel human parvovirus B19 variant genomes are provided. Also provided are assays and kits comprising the nucleic acid molecules.

3 Claims, 39 Drawing Sheets

5'-
CAGCTCTTTCTTTTGGGGTTGCTTTTACCTGGACTTTTCTTGCTGTCTTTTGCGTGCTAACTAACAGGTATTTATACTACTTGTTAACTTACTAACATG
GAGTTATTTAGAGGGGTGATTCAAGTTTCTTCTAACATTCTTGACTGTGCTAACGATAACTGGTGGTGCTCTATGCTGGATTTAGACACTTCTGACTGGG
AACCATTAACTCATTCTAACAGACTAATGGCAATATATTTAAGCAGCGTGGCTTCTAAGCTTGACTTTACAGGGGGGCCCTTAGCTGGGTGCTTGTACTT
TTTTCAGGTGGAATGTAACAAATTTGAGGAAGGCTATCATATCCATGTGGTTATTGGGGACCAGGGCTAAACCCTAGAAACCTAACAGTGTGTGTAGAG
GGATTATTTAATAATGTACTTTACCACCTTGTAACTGAAAATGTAAAGCTTAAATTTTTACCAGGAATGACTACAAAAGGCAAATATTTTAGAGATGGAG
AACAATTTATAGAAAATTATTTAATGAAAAAAATACCTTTAAATGTTGTATGGTGTGTAACCAATATTGATGGGTACATAGATAGCTGCATTTCTGCTTC
TTTTAGACGGGGAGGCTTTCAGGCTAAAAAACCCCGCATTAGTGCAAACACTGATGGGGGTTCTAATGAACCAGGGGAATCTAGCGCTACAGGGGGAGAT
GTTGTGCCATTTGCTGGGAAGGGACTAAAGCTGGAATAAAATTTCAAACTATGGTAAATTGGTTGTGTGAAAATAGGGTTTTTACAGAGGATAAGTGGA
AACTAGTTGACTTTAACCAGTACACTTTACTTAGCAGTAGTCACAGTGGGAGCTTTCAAATACAAAGTGCATTAAAACTAGCTATTTATAAGGCTACCAA
TTTAGTGCCTACAAGTACATTTTGTTACACACAGACTTTGAGCAGGCTAACTGTATTAAAGAAAATAAAATAGTTAAACTGTTACTGTGTCAAAATTAT
GACCCCTTGCTGGTGGGACAGCATGTGTTAAAGTGGATTGATAAAAAATGTGGCAAAAAAAATACACTGTGGTPTTATGGCCCACCAAGTACAGGAAAAA
CAAATTTAGCAATGGCTATTGCTAAAACTGTTCCAGTGTATGGTATGGTTAATTGGAATAATGAAAATTTTCCATTTAATGATGTAGTAGGAAAAAGCTT
GGTGGTCTGGGATGAGGGTATTATTAAGTCTACTATTGTAGAAGCTGCAAAAGCCATTTTAGGAGGCAACCAACCAGGGTAGATCAAAAAATGCGTGGA
AGTGTAGCAGTGCCTGGAGTACCAGTGGTAATAACCAGCAATGGTGACATTACTTTTGTTGTTAGTGGGAACACTACAACAACTGTCCATGCTAAAGCCT
TAAAGGAGCGAATGGTAAAGTTAAACTTTACCATAAGATGTAGCCCTGACATGGGCTTACTTACAGAGGCTGACGTGCAGCAATGGCTTACATGGTGTAA
TGCACAAAGCTGGAGCCACTATGAAAACTGGGCAATAAACTACACTTTTGATTTCCCTGGAATAAATGCAGATGCCCTCCACCCAGACCTCCAAACCACC
CCAATTGTCACAGACACCAGTGTCAGCAGCAGTGGTGGTGAAAAGCTCTGAAGAACTCAGTGAAAGCAGCTTTCTCAACCTCATCACCCCAGGCGCCTGGA
ACACTGAAACCCCGCGCTCTAGTACGCCAGTCCCCGGGACCAGTTCAGGAGAATCATTTGTCGGAAGCTCAATTTCCTCCGAAGCTGTAGCTGCATCGTG
GGAAGAAGCCTTCTACACACCCTTTGGCAGATCAGTTTCGTGAACTGTTAGTTGGGGTTGACTATGTATGGGATGGTATAAGGGGTTTACCTGTTTGTTGT
GTGCAACATATTAATAACAGTGGGGGAGGCTTGGGATTTTGTCCCCATTGCATTAATGTGGGGGCTTGGTATAATGGATGGAAGTTTCGAGAATTTACCC
CAGATTTGGTGCGGTGTAGCTGTCATGTAGGAGCTTCTAATCCTTTTTCTGTGTTAACCTGCAAAAAATGTGCTTACCTATCTGGCTTGCAAAGTTTTGT
AGATTATGAGTAAAGAAATTGGTAAATGGTGGGAAAGTGATGATAAATTTGCTAAGGACGTGTATAAGCAATTTGTAGAAATTTATGAAAAAGTTACTGG
AACAGACTTAGAGCTTATTCAAATATTAAAAGATCATTACAATATTTCTTTAGATAATCCTCTAGAAAACCCATCTTCTTTGTTTGACTTAGTGGCTCGT
ATTAAAAGTAACTTAAAAACTCTCCAGACTTATATAGTCATCATTTTCAAAGTCATGGACAGTTATCTGACCACCCCCATGCCTTATCATCCAGTAACA
GTGATGCAGAACCTAGAGGAGAAAATGCAGTATTATCTAGTGAAGACTTACACAAGCCTGGGCAAGTTAGCATACAACTACCCGGTACTAACTATGTTGG
GCCTGGCAATGAGCTACAAGCTGGGCCCCCGCAGAGTGCTGTGGACAGTGCTGCCAASGATTCATGACTTTAGGTATAGCCAACTGGCTAAGCTGGGAATA
AATCCATATACTCATTGGACTGTAGCAGATGAGGAGCTGTTAAAAAATATAAAAAATGAAACTGGGTTTCAAGCTCAAGTAGTAAAAGACTACTTTACTT
TAAAAGGTGCAGCTGCCCCTGTGGCCCATTTTCAAGGAAGTTTGCCGGAAGTTCCCGCTTACAACGCCTCAGAAAAATACCCAAGCATGACTTCAGTTAA
TTCTGCAGAAGCCAGCACTGGTGCAGGAGGGGGCGGCAGTAATCCTACTAAAAGCATGTGGAGTGAGGGGCTACTTTTACTGCCAACTCTGTAACTTGT
ACATTTTCCAGACAGTTTTTAATCCCATATGATCCAGAGCACCATTATAAAGTGTTTCTCCCGCAGCCAGTAGCTGCCACAATGCCAGTGGAAAAGAGG
CAAAAGTTTGCCACCATTAGTCCCATAATGGGATACTCCACACCATGGAGATACTTAGATTTTAATGCTTTAAATTTATTTTTTTCACCCTTTAGAGTTTCA
ACATTTAATTGAGAATTATGGAAGTATAGCTCCTGATGCTTTAACTGTTGCCATATCGAAATTGCCATTAAAGATGTTACAGACAAAACTGGAGGAGGG
GTACAGGTTACTGACAGTACTACAGGGCGTTTATGCATGTTAGTAGACCATGAATACAAGTACCCATATGTATTAGGTCAAGGACAAGATACCTTAGCCC
CAGAGCTTCCAATTTGGGTGTACTTTCCACCTCAATATGCTTACTTAACAGTAGGAGATGTAAACACGCAGGGAATTTCTGGGGACAGTAAAAAATTAGC
TAGTGAAGAATCAGCGTTTTATGTCCTGGAACACAGCTCTTTTGAACTTTTAGGTCAGGGGGCTCTGCTACTATGTCTTATAAGTTCCCTCCAGTGCCC
CCAGAGAATTTAGAAGGCTGTAGTCAACACTTTTATGAAATGTACAACCCGTTATATGGATCCCGTTTAGGAGTCCCTGATACATTAGGAGGGGACCCCA
AATTTAGATCTTTAACACATGAAGACCAGCAGTTCAGCCACAAAATTTTATGCCAGGGCCACTGGTAAACTCAGTTTCCACAAAGGAGGGAGACAGTTC
TAACACAGGAGCGGGAAAAGCCCTAACAGGCCTTAGCACAGGCACTAGTCAAAGTACTAGAATATCATTACGCCCTGGTCCTGTCTCAACCATATCAC
CACTGGGACACAGATAAAATGTAACAGGGATAAATGCCATTTCTCATGGTCAAACCACTTATGGCAATGCTGAAGACAAAGAGTATCAACAGGGCGTGG
GTAGGTTTCCCAATGAAAAAGAACAACTAAAACAGTTACAGGGTTAAATATACACACATATTTTCCCAATAAAGGTACCCAGCAATATACAGATCAAAT
TGAGCGCCCCCTAATGGTAGGGTCTGTATGGAACAGAAGAGCCCTTCACTATGAAAGCCAGCTGTGGAGTAAAATACCAAATTTAGATGACAGCTTTAAA
ACTCAGTTTGCAGCTTTAGGAGGTTGGGGACTACATCAGCCACCCCCTCAAATATTTTAAAAATATTACCACAAAGTGGGCCAATTGGGGTATTAAGT
CAATGGGAATAACAACATTAGTTCAATATGCTGTGGGTATTATGACAGTAACTATGACATTTAAATTAGGGCCTCGCAAAGCTACAGGACGGTGGAATCC
TCAACCTGGAGTGTACCCTCCTCACGCAGCAGGCCATTTACCCATATGTACTATATGACCCCACAGCTACAGATGCAAAGCAACACCACAGACATGGATAT
GAAAAGCCTGAAGAATTGTGACTGCCAAAAGCCGTGTGCACCCATTGTAACACTCCCCACCGTGCCCTCAGCCAGGATGTGTAACTAAACGCCCACCA
GTGCCACCTAGACTGTATTTACCCCCCCCTGTACCTATAAGACAGCCTACCACAAAAGACACAGACAATGTAGAGTTTAAATACTTAAGCCGCTATGAAC
AACATGTAATTAGAATGTTAAGATTGTGTTAATATGTATAAAAATTTAGAAAAATAAACACTTGTTGCAGTTAATAAATTGCGTATGTGTGTTTAAAAA
TTTAAAAGAAGACACCAAATCAGATGCCGCCGGTCGCCGCCGGTAGGCGGGACTTCCGGTACAAGATGGCGGAAATTCA - 3'

```
ACGCGGGGACTACAGTATATATAGCACGGCACTGCCGCAGCTCTTTCTTTCTGAGCTGCTTTTTCCTGGAC
TTTCTTGCTGTTGTTTGTGAGCTAACTAACAGGTATTTATACTACTTGTTAACATACTAACATGGAGCTAT
TTAGAGGGGTGCTTCAAGTTTCTTCTAATGTTCTGGACTGTGCTAACGATAACTGGTGGTGCTCTTTACTG
GATTTAGACACCTCTGACTGGGAACCACTAACTCATACTAACAGACTAATGGCAATATACCTAAAACAGTG
TGGCTTCTAAGCTTGACTTTACCGGGGGGCCACTAGCAGGGTGCTTGTACTTTTTCAAGTTGAATGTAAC
AAATTTGAAGAAGGCTATCATATTCATGTGGTTATTGGGGGCCAGGGTTAAACCCCAGAAACCTAACAGT
GTGTGTAGAGGGGTTATTTAACAATGTACTTTATCACCTTGTAACTGGAGATGTAAAGCTAAAATTTTGC
CAGGAATGACTACAAAAGGCAAATACTTTAGAGATGGAGAGCAGTTTATAGAAAACTATTTAATGAAAAA
ATACCTTTGAATGTTGTATGGTGTGTTACTAATATTGATGGATATATAGATACCTGTATTTCTGCTACTTT
TAGAAGGGGAGCTTGCCATGCCAAGAAACCCGCATGACCACAGCCATAAATGATACTAGTAGTGATGCTG
GGGAGTCTAGCGGCACAGGGGCAGAGGTTGTGCCATTTAATGGAAAGGGAACTAAGGCTAGCATAAAGTTT
CAGACTATGGTAAACTGGTTGTGTGAAAATAGAGTGTTTACAGAGGATAAGTGGAAACTAGTTGACTTTAA
CCAGTACACTTTACTAAGCAGTAGTCACAGTGGAAGTTTTCAAATTCAAAGTGCACTAAAACTAGCAATTT
ATAAAGCAACTAATTTAGTGCCTACTAGCACATTTTTATTGCATACAGACTTTGAGCAGGTTATGTGTATT
AAAGACAATAAAATTGTTAAATTGTTACTTTGTCAAAACTATGACCCCCTATTGGTGGGGCAGCATGTGTT
AAAGTGGATTGATAAAAAATGTGGCAAGAAAAATACACTGTGGTTTATGGGCCGCCAAGTACAGGAAAAA
CAAACTTGGCAATGGCTATTGCTAAAAGTGTTCCAGTATATGGCATGGTTAACTGGAATAATGAAAACTTT
CCATTTAATGATGTAGCAGGGAAAAGCTTGGTGGTCTGGGATGAAGGTATTATTAAGTCCACAATTGTAGA
AGCTGCAAAAGCCATTTTAGGCGGGCAACCTACCAGGGTAGATCAAAAAATGCGTGGAAGTGTAGCTGTGC
CTGGAGTACCTGTGGTTATAACCAGCAATGGTGACATTACTTTTGTTGTAAGCGGGAACACTACAACAACT
GTACACGCTAAAGCCTTAAAAGAGCGCATGGTAAAGTTAAACTTTACTGTAAGATGCAGCCCTGACATGGG
GTTACTAACAGAGGCTGATGTACAACAGTGGCTTACATGGTGTAATGCACAAAGCTGGGACCACTATGAAA
ACTGGGCAATAAACTACACTTTTGATTTCCCTGGAATTAATGCAGATGCCCTCCACCCAGACCTCCAAACC
ACCCCAATTGTCACAGACACCAGTATCAGCAGCAGTGGTGGTGAAAGCTCTGAAGAACTCAGTGAAAGCAG
CTTTTTTAACCTCATCACCCCAGGCGCCTGGAACACTGAAACCCGCGCTCTAGTACGCCCATCCCCGGGA
CCAGTCAGGAGAATCATCTGTCGGAAGCCCAGTTTCCTCCGAAGTTGTAGCTGCATCGTGGGAAGAAGCC
TTCTACACACCTTTGGCAGACCAGTTTCGTGAACTGTTAGTTGGGGTTGATTATGTGTGGGACGGTGTAAG
GGGTTTACCTGTGTGTTGTGTGCAGCATATTAACAATAGTGGGGGAGGCTTGGGACTTTGTCCCCATTGCA
TTAATGTAGGGGCTTGGTATAATGGATGGAAATTTCGAGAATTTACCCCAGATTTGGTGCGGTGTAGCTGC
CATGTGGGAGCTTCTAATCCCTTTTCTGTGCTAACCTGCAAAAAATGTGCTTACCTGTCTGGATTGCAAAG
CTTTGTAGATTATGAGTAAAGAAAGTGGCAAATGGTGGGAAAGTGATGATAAATTTGCTAAAGCTGTGTAT
CAGCAATTTGTGGAATTTTATGAAAAGCTTACTGGAACAGACTTAGAGCTTATTCAAATATTAAAAGATCA
TTACAATATTTCTTTAGATAATCCCCTAGAAAACCCATCCTCTCTGTTTGACTTAGTTGCTCGTATTAAAA
ATAACCTTAAAAACTCTCCAGACTTATATAGTCATCATTTTCAAAGTCATGGACAGTTATCTGACCACCCC
CATGCCTTATCATCCAGTAACAGTCATGCAGAACCTAGAGGAGAAAATGCAGTATTATCTAGTGAAGACTT
ACACAAGCCTGGGCAAGTTAGCGTACAACTACCCGGTACTAACTATGTTGGGCCTGGCAATGAGCTACAAG
CTGGGCCCCGCAAAGTGCTGTTGACAGTGCTGCAAGGATTCATGACTTTAGGTATAGCCAACTGGCTAAG
TTGGGAATAAATCCATATACTCATTGGACTGTAGCAGATGAAGAGCTTTTAAATAATATAAAAAATGAAAC
TGGGTTTCAAGCACAAGTAGTAAAAGACTACTTTACTTTAAAAGGTGCAGCTGCCCCTGTGGCCCATTTTC
AAGGAAGTTTGCCGGAAGTTCCCGCTTACAACGCCTCAGAAAAATACCCAAGCATGACTTCAGTTAATTCT
GCAGAAGCCAGCACTGGTGCAGGAGGGGGGGCAGTAATCCTGTTAAAAGCATGTGGAGTGAGGGGCCAC
TTTTAGTGCCAACTCTGTAACTTGTACATTTTCCAGACAGTTTTTAATTCCATATGACCCAGAGCACCATT
ATAAGGTGTTTTCTCCCGCAGCAAGTAGCTGCCACAATGCCAGTGGAAAGGAGGCAAAGGTTTGCACCATT
AGTCCCATAATGGGATACTCAACCCCATGGAGATATTTAGATTTTAATGCTTTAAATTTGTTTTTTTCACC
TTTAGAGTTTCAGCATTTAATTGAAAACTATGGAAGTATAGCTCCTGATGCTTTAACTGTAACCATATCAG
AAATTGCTGTTAAGGATGTTACAGACAAAACTGGAGGGGGAGTACAAGTTACTGACAGCACTACCGGGCGC
CTATGCATGTTAGTAGACCATGAATACAAGTACCCATATGTGTTAGGGCAAGGTCAGGATACTTTAGCCCC
AGAACTTCCTATTTGGGTATACTTTCCCCCTCAATATGCTTACTTGACAGTAGGAGATGTTAACACACAAG
GAATTTCTGGAGACAGCAAAAAATTAGCAAGTGAAGAATCAGCATTTTATGTTTTGGAACACAGTTCTTTT
CAGCTTTTAGGTACAGGAGGTACAGCAACTATGTCCTATAAGTTTCCTCCAGTGCCCCCAGAAAATTTAGA
GGGCTGCAGTCAACACTTTTATGAAATGTACAATCCCTTATACGGATCTCGCTTAGGGGTCCCTGACACAT
TAGGAGGTGACCCAAAATTTAGATCTTTAACACATGAAGACCATGCAATTCAGCCCCAAAACTTTATGCCA
```

```
GGGCCACTAGTAAACTCAGTGTCTACAAAGGAGGGAGACAGCTCTAGTACTGGAGCTGGAAAAGCCTTAAC
AGGCCTTAGCACAGGAACCTCTCAAAACACTAGAATATCCTTACGCCCTGGGCCAGTGTCTCAGCCATATC
ACCACTGGGACACAGATAAATATGTTACAGGAATAAATGCCATTTCTCATGGTCAGACCACATATGGTAAT
GCTGAAGATAAAGAGTATCAGCAAGGAGTGGGTAGATTTCCAAATGAAAAAGAACAGCTAAAACAGTTACA
GGGCTTAAACATGCACACCTATTTTCCCAATAAAGGAACCCAGCAATATACAGATCAAATTGAGCGCCCCC
TAATGGTGGGTTCTGTATGGAACAGAAGAGCCCTTCACTATGAAAGCCAGCTGTGGAGTAAAATTCCAAAT
TTAGATGACAGTTTTAAAACTCAGTTTGCAGCCTTAGGAGGATGGGGTTTGCATCAGCCACCTCCTCAAAT
ATTTTTAAAAATATTACCACAAAGTGGGCCCATTGGAGGTATTAAATCAATGGGAATTACTACCTTAGTTC
AGTATGCCGTGGGAATTATGACAGTCACTATGACATTTAAATTGGGGGCCCGTAAAGCTACGGGACGGTGG
AATCCTCAACCTGGAGTATATCCCCGCACGCCGCAGGTCATTTACCATATGTACTATATGACCCCACAGC
TACAGATGCAAAACAACACCACAGACATGGATATGAAAAGCCTGAAGAATTGTGGACAGCCAAAAGCCGTG
TGCACCCATTGTAAACACTCCCCACCGTGCCCTCAGCCAGGATGCGTAACTAAACGCCCACCAGTACCACC
CAGACTGTACCTGCCCCCGCGTATACCTATAAGACAGCCTAACACAAAAGATATAGACAATGTAGAA
```

```
ATCTGATTTGGTGTCTTCTTTTTAAAATTTTGGCGGGCTTTTTCCCGCCTTATGCAAATAAGCTGCCATGT
TTAATATTTTATTTTAATTTAATTGGACAGACGCCTAACGGTTATTATAGGCGGAGTTACGGGCGGTATAT
AAGCAGCTGTGCTCTGTGGCACTTTCTTTTCTGGTTGCTTTTGACTGGAACTCACTTGCTGTTCTTTGCCT
GCTAACTAACAGGTATTTATACTAACTTTTAATTTACTAACATGGAGCTATTTCGGGGTGTCTTGCACATT
TCCTCTAACATTCTGGACTGTGCTAATGATAACTGGTGGTGCTCTATGCTAGACTTAGATACTTCTGATTG
GGAACCACTAACTCATTCTAACAGATTAATGGCAATATATTTAAGCAGTGTTGCTTCTAAGCTTGATTTTA
CTGGGGGGCCGCTAGCAGGTTGCTTATACTTTTTCCAGGTGGAGTGTAACAAATTTGAGGAAGGCTATCAT
ATTCATGTAGTTATTGGTGGTCCAGGACTAAATGCTAGAAACTTAACTGTGTGTGTAGAAGGTTTATTTAA
TAATGTTCTTTACCACCTTGTAACTGAAAGTGTTAAACTTAAATTTTTGCCAGGGATGACTACCAAAGGAA
AATATTTTAGAGATGGAGAGCAGTTTATAGAAAATTACTTAATGAAAAAAATTCCTTTAAATGTTGTGTGG
TGTGTAACAAATATTGACGGGTATATAGACACCTGTATTTCCGCCTCTTTTCGGCGAGGAGCTTGTCAAGC
TAAAAGACCCCGCATTGCCGCAAATGCAGACAGTGTTACTAGTGAAACCGGGGAGTCTAGCTGTGCAGGGG
GAGATGTTGTACCATTTGCTGGAAAGGGAACAAAAGCGGGGTTAAAGTTTCAAACCATGGTAAATTGGCTA
TGTGAAAACAGAGTATTTACTGAAGATAAATGGAAGTTAGTAGATTTTAACCAGTATACCTTATTAAGTAG
TAGTCACAGTGGCAGCTTTCAAATACAAAGTGCCTTAAAGTTAGCTATTTATAAAGCTACTAACTTAGTAC
CCACTAGTACATTCTTGTTACATGCAGACTTTGAGCAGGTTACTTGCATTAAAGAAAATAAAATAGTTAAA
TTATTACTGTGTCAAAACTATGATCCTCTGCTAGTGGGGCAACATGTGTTAAGGTGGATTGACAAAAAATG
TGGTAAAAAAAACACCCTATGGTTTTACGGGCCACCAAGTACTGGAAAAACAAATTTAGCTATGGCTATTG
CTAAAACTGTACCCGTGTATGGAATGGTTAACTGGAATAATGAAAACTTTCCATTTAATGATGTGGCGGGG
AAAAGTTTGGTGGTCTGGGATGAAGGCATTATTAAGTCCACTATTGTGGAAGCTGCAAAAGCCATTCTAGG
TGGTCAGCCAACCAGGGTAGATCAGAAAATGCGTGGCAGTGTGGCAGTGCCCGGTGTGCCTGTGGTCATAA
CCAGCAACGGTGACATTACATTTGTTGTAAGTGGTAATACCACTACAACTGTGCATGCTAAAGCCTTAAAA
GAACGGATGGTAAAGCTAAATTTTACCATAAGGTGTAGCCCTGACATGGGTTTACTAACAGAGGCTGATGT
GCAACAGTGGCTAACTTGGTGTAATGCACAAAGCTGGAGCCACTATGAAAACTGGGCAATAAACTACACGT
TTGATTTCCCTGGAATAAATGCAGATGCCCTCCACCCAGATCTCCAAACCACCCCATTGTCCCAGACACC
AGTATCAGCAGCAGTGGTGGTGAAAGCTCTGAAGAACTCAGTGAAAGCAGCTTTTTCAACCTCATCACTCC
AGGCGCCTGGAACAGTGAAACCCCGCGCTCTAGTACGCCCGTCCCCGGGACCAGTTCAGGAGAATCATTTG
TCGGAAGCCCAGTTTCCTCCGAAGTGGTAGCCGCGTCGTGGGAGGAAGCTTTTTACACGCCGCTTGCAGAT
CAGTTTCGTGAACTGTTAGTAGGGGTTGACTATGTATGGGATGGTGTAAGGGGATTGCCTGTTTGCTGTGT
GGAACATATTAATAACAGTGGGGGAGGGTTGGGGCTTTGTCCTCATTGTATTCATGTGGGAGCTTGGTATA
ATGGATGGAAATTTAGAGAGTTTACTCCAGACTTAGTGCGCTGTAGTTGTCATGTAGGAGCCTCTAACCCA
TTTTCTGTGTTAACTTGTAAAAAATGTGCTTACCTGTCTGGTTTACAAAGCTTTGTAGATTATGAGTAAAA
CCACTGACAAATGGTGGGAAAGTAGTGACAAATTTGCCCAGGACGTGTATAAGCAGTTTGTACAATTTTAT
GAAAAGCTACTGGAACAGATTTAGAGCTTATTCAAATTTTAAAAGATCATTACAACATTTCTTTAGACAA
TCCTTTAGAAAACCCCTCTTCTTTATTTGACTTAGTTGCTCGCATTAAAAGCAATCTTAAAAACTCTCCAG
ACCTATATAGTCATCATTTTCAGAGCCATGGACAGTTATCTGACCACCCCCATTCCTTATCACCCAGTAAC
AGTAGTACAGAACCTAGAGGAGAAAATGCAGTATTATCTAGTGAAGACTTACACAAGCCTGGGCAAGTTAG
CATACAATTACCCGGTACTAACTATGTTGGGCCTGGCAATGAGCTACAAGCTGGGCCTCCGCAGAATGCTG
TGGACAGTGCTGCAAGGATTCATGACTTTAGGTATAGCCAATTGGCTAAGTTGGGAATAAATCCTTATACT
CATTGGACGGTAGCAGATGAGGAATTGTTAAAAAATATAAAAAATGAAACAGGGTTTCAAGCACAAGCAGT
AAAAGACTACTTTACTTTAAAAGGTGCAGCTGCCCCTGTGGCCCATTTTCAAGGAAGTTTACCGGAAGTGC
CCGCGTACAACGCCTCAGAAAAATACCCCAGCATGACTTCAGTTAACTCTGCAGAAGCCAGCACTGGTGCA
GGCGGGGAGGTAGCAACCCTACAAAAAGCATGTGGAATGAAGGGGCTACATTCACTGCTAATTCTGTAAC
ATGCACATTCTCTAGGCAATTTTTAATTCCATATGATCCAGAGCATCATTATAAAGTGTTCTCCCCAGCAG
CTAGTAGCTGCCACAATGCTAGCGGAAAAGAGGCAAAAGTGTGCACTATTAGTCCCATTATGGGTACTCT
ACTCCGTGGAGATACTTAGATTTTAATGCTTTAAACTTGTTTTTCTCACCATTAGAGTTTCAGCACTTAAT
TGAAAATTATGGCAGCATAGCTCCAGATGCTTTAACTGTAACTATTTCAGAAATTGCTGTAAAAGATGTTA
CAGACAAAACAGGGGGAGGTGTGCAAGTTACTGACAGCACAACAGGACGTTTGTGTATGTTAGTGGATCAT
GAGTATAAGTACCCATATGTGCTAGGTCAGGGACAAGACACACTAGCTCCAGAACTGCCCATTTGGGTGTA
CTTTCCCCCCAATATGCTTACTTAACAGTAGGTGAAGTAAACACACAAGGAATTTCAGGAGACAGCAAAA
AATTAGCTAGTGAAGAATCAGCTTTTTATGTGTTAGAGCACAGTTCATTTGAACTTTTAGGTACAGGGGGA
TCAGCCACAATGTCCTACAAATTTCCAGCAGTGCCCCCAGAAAACTTAGAAGGTTGCAGCCAACATTTTTA
TGAAATGTACAACCCCCTGTACGGTTCCCGATTAGGGGTACCTGACACATTAGGAGGGGACCCTAAATTTA
```

```
GATCATTAACACACGAAGACCATGCAATTCAGCCACAAAACTTTATGCCTGGGCCACTAATAAATTCAGTA
TCTACCAAAGAAGGAGACAATTCTAATACAGGTGCTGGAAAAGCCCTTACGGGGCTTAGTACTGGCACTAG
TCAAAACACCAGAATTTCCCTACGCCCAGGGCCAGTGTCTCAGCCATACCATCACTGGGACACTGATAAAT
ATGTTACAGGAATAAATGCCATTTCACATGGACAAACCACCTATGGAAATGCTGAGGACAAAGAATATCAG
CAAGGGGTAGGAAGATTTCCAAACGAAAAAGAACAGCTTAAGCAGTTACAGGGTCTTAACATGCACACATA
CTTTCCTAATAAAGGAACCCAACAATACACAGACCAAATTGAACGCCCCCTTATGGTAGGCTCTGTTTGGA
ACAGAAGAGCACTTCACTATGAAAGTCAGCTGTGGAGTAAAATCCCTAACTTAGATGATAGTTTTAAAACT
CAATTTGCAGCCCTAGGAGGTTGGGGTTTGCATCAACCACCCCCTCAAATATTTTTAAAAATACTACCGCA
AAGTGGGCCAATTGGAGGTATTAAATCCATGGGAATTACTACTTTAGTTCAATATGCTGTGGGAATAATGA
CAGTTACTATGACATTTAAATTGGGACCTCGAAAGGCTACTGGAAGGTGGAATCCCCAGCCTGGAGTGTAT
CCTCCTCATGCAGCTGGTCATTTACCATATGTACTGTATGACCCCACAGCTACAGATGCAAAGCAACACCA
CAGACACGGATATGAAAAGCCTGAAGAATTGTGGACTGCCAAAAGCCGTGTGCACCCATTGTAAACATTCC
CCACCGTGCCCTCTGCCAGGAACCGTCACCAATCGCCCACCTGTACCGCCCAGATTATATGTGCCCCCTCC
AATACCCCGTAGGCAACCATCTATAAAAGATACAGACGCTGTAGAGTATAAATTACTAACCCGATATGAAC
AACATGTAATAAGAATGCTAAGATTATGTAATATGTACACAAACTTGGAAAAATAAAAACCTTAAATAAAA
AATTAATAGTGTATGGTG
```

FIG. 3B

```
SEQ ID NO: 1     1   GATAACTGGTGGTGCTCTATGCTGGATTAGACACTTCTGACTGGAACCATTAACTC    58
SEQ ID NO: 130 493   GATAACTGGTGGTGCTCTTTACTGGATTAGACACTTCTGACTGGAACCACTAACTC   550
                     ||||||||||||||||||  |||||||||||||||||||||||||||||| |||||
SEQ ID NO: 131 290   GATAACTGGTGGTGCTCTATGCTGGATTAGACTTCTGACTGGAACCACTAACTC    349
                     ||||||||||||||||||||||||||||||||  ||||||||||||||||| ||||
SEQ ID NO: 132 385   GATAACTGGTGGTGCTCTATGCTAGACTTAGATACTTCTGACTGGAACCACTAACCC  442
                     ||||||||||||||||||||||| || ||| ||| |||||||||||||||| |||||
SEQ ID NO: 133 380   GATAACTGGTGGTGCTCTATGCTGGACCTAGACACTTCTGACTGGAGCCACTAACCC  437
                     |||||||||||||||||||||||||| | ||||||||||||||||| |||||| |||

SEQ ID NO: 1    59   ATTCTAACAGACTAATGGCAATATATATTAAGCAGCTGGCTTCTAAGCTTGACTTTACAG  118
SEQ ID NO: 130 551   ATACTAACAGACTAATGGCAATATACTTAAGCAGTGTGGCTTCTAAGCTTGACTTTACCG  610
                     || |||||||||||||||||||||| |||||||| |||||||||||||||||||||| |
SEQ ID NO: 131 350   ACTCTAACAGACTAATGGCAATATATTAAGTAATGTTGCTTCTAAACTGGATTTTACTG   409
                     |  ||||||||||||||||||||||  |||| || || |||||||| || ||||||| |
SEQ ID NO: 132 443   ATTCTAACAGATTAATGGCAATATATTAAGCAGTGTTGCTTCTAAACTTGATTTTACTG   502
                     || ||||||||  ||||||||||||| |||||| || |||||||| || ||||||| |
SEQ ID NO: 133 438   ACTCTAACAGACTCATGGCAATATATTAAGCAGCGTTGCTTCTAAGCTTGATTTTACTG   497
                     |  |||||||||  |||||||||||| |||||| || ||||||||||||| ||||| |

SEQ ID NO: 1   119   GGGGGCCCTTAGCTACTTTTTTCAGGTGGAATGTAACAAATTGAGGAAG              178
SEQ ID NO: 130 611   GGGGGCCACTACTAGCAGGTGCTTGTACTTTTTTCAAGTAAGTAGAATGTAACAAATTGAAGAAG   670
                     ||||||| ||    || ||||  || |||||||| |    |||||||||||||||||| |||||
SEQ ID NO: 131 410   GGGGGCCGCTGGCGGGTTGCTTATACTTTTTTCAGGTGGAATGTAACAAATTGAGGAAG        469
                     ||||||| |   |  |||||| |||||||||||| |||||||||||||||||||| |||
SEQ ID NO: 132 503   GGGGGCCGCTAGCAGGTGCTTGCTTATACTTTTTTCAGGTGGAATGTAACAAATTGAGGAAG    562
                     ||||||| |    ||||||||  |||||||||||| |||||||||||||||||||||||||
SEQ ID NO: 133 498   GGGGGCCACTACTGCAGGTGCTGCAGGTGCTTATACTTTTTTCAGGTGGAATGTAACAAATTGAGGAAG 557
                     ||||||| ||      ||||   ||| | ||||| |||||||| |||||||||||||||||||||||

SEQ ID NO: 1   179   GCTATCATATCCATGTGGTTATTGGGGGACCAGGCTAAACCCTAGAAACCTAACAGTGT  235
SEQ ID NO: 130 671   GCTATCATATTCATGTGGTTACTGGGGGCCAGGGTTAAACCCCAGAAACCTTACAGTGT  730
                     |||||||||| |||||||||| ||||||| |||| ||||||| |||||||| ||||||
SEQ ID NO: 131 470   GCTACCATATTCATCTAGTTATTGGTGGTCCAGGACTAAATGCTAAAACTTAACAGTGT  529
                     |||| ||||| |||  ||||| |||  | ||||| |||||  |  || ||||||||||
SEQ ID NO: 132 563   GCTATCATATCCATCTAGTTATTGGTGGTCCAGGACTAAATGCTAGAAACTTAACTGTGT 622
                     |||||||||| |||  ||||| |||  | ||||| |||||  |||||| |||| ||||
SEQ ID NO: 133 558   GCTATCACATTCATGTGGTTATTGGTGGTCCAGGACTGAATGCTAGAAATTTAACTGTGT 617
                     ||||||| || |||||||||| |||  | ||||| || |||||||||| ||||| ||||
```

```
SEQ ID NO:   1    719   TAAAACTAGCTATTTATAAGGCTACCAATTTAGTGCCTACAAGTACATTTTTGTTACACA  778
SEQ ID NO: 130   1211   TAAAACTAGCAATTTATAAAGCAACTAATTTAGTGCCTACTAGCACATTTTTATTGCATA 1270
SEQ ID NO: 131   1010   TAAAGCTAGCTATTTATAAAGCTACTAACTAGTTCCTACTAGTACATTTTTAATGCATT  1069
SEQ ID NO: 132   1103   TAAAGTTAGCTATTTATAAAGCTACTAACTTAGTAGTACCCACTAGTACATTCTGTTACATT 1162
SEQ ID NO: 133   1098   TAAAGTTAGCTATCTCTATAAAGCCACTAACTAGTACCTACTAGCACTTTTTTGTTACATT 1157

SEQ ID NO:   1    779   CAGACTTTGAGCAGGCTAACTGTATTAAAGAAAATAAAATAGTTAAACTGTTACTGTGTC  838
SEQ ID NO: 130   1271   CAGACTTTGAGCAGCAGGTTATGTGTATTAAAGACAATAAAATTGTTAAATTGTTACTTTGTC 1330
SEQ ID NO: 131   1070   CAGACTTTGAGCAGCAGGTTACCTGCATTAAAGAAAATAAAATAGTTAAACTATTATTATGCC 1129
SEQ ID NO: 132   1163   CAGACTTTGAGCAGCAGGTTACTTGCATTGCATTAAAGAAAATAAAATAGTAAAATTATTATTGTTGTC 1222
SEQ ID NO: 133   1158   CAGACTTTGAGCAGTTACTTGCATTAAAGATAATAAAATAGTTAAATTGTTACTGTGCC 1217
SEQ ID NO: 128     1    TATTAAAGACAATAAAATTGTTAAATTGTTACTTTGTC                         38
SEQ ID NO: 129     1    AATAAAATAGTTAAATTATTACTGTGTC                                    28

SEQ ID NO:   1    839   AAAATTATGACCCCTGTTGGTGGGACAGCATGTGTTAAAGTGGATTGATAAAAATGTG    898
SEQ ID NO: 130   1331   AAAACTATGACCCCCTATTGGTGGGCAGCATGTGTTAAAGTGGATTGATAAAAATGTG   1390
SEQ ID NO: 131   1130   AGAATTATGATCCTCTCTTTTAGTGGGTCAACATGTTTAAAGTGGATTGACAAAATGTG   1189
SEQ ID NO: 132   1223   AAAACTATGATCCTCTCTTTAGTGGGTCAACATGTGTTAAGGTGGATTGACAAAATGTG   1282
SEQ ID NO: 133   1218   AAAACTATGATCCTCTTCTAGTAGGGCAACATGTGTTAAGGTGGATTGACAAAAATGTG  1277
SEQ ID NO: 128    39   AAAACTATGACCCCCTATTGGTGGGCAGCAGCATGTTAAAGTGGATTGATAAAAATGTG    98
SEQ ID NO: 129    29   AAAACTATGATCCTCGCTAGTGGGCAACATGTGTTAAGGTGTTAAGGTGATTGACAAAAATGTG 88
```

| | | | | |
|---|---|---|---|---|
| SEQ ID NO: 1 | 1619 | TTTCCTCCGAAGCTGTAGCTGCATCGTGGGAAGAAGCCTTCTACACACCTTTGGCAGATC | 1678 |
| SEQ ID NO: 130 | 2111 | TTTCCTCCGAAGCTGTAGCTGCATCGTGGGAAGAAGCCTTCTACACACCTTTGGCAGACC | 2170 |
| SEQ ID NO: 131 | 1910 | TTTCCTCCGAAGTGGTAGCCGCGTCGTGGGAAGAAGCCTTTTACACTCCACTGCAGACC | 1969 |
| SEQ ID NO: 132 | 2003 | TTTCCTCCGAAGTGGTAGCCGCGTCGTGGGAAGAAGCCTTTTACACGCCGCTGCCGATC | 2062 |
| SEQ ID NO: 133 | 1998 | TTTCCTCCGAAGTTGTAGCTGGTAGCCGCGTCGTGGGAAGAAGCCTTTTACACGCCACTGCAGATC | 2057 |
| SEQ ID NO: 128 | 819 | TTTCCTCCGAAGTTGTAGCTGCATCGTGGGAAGAAGCCTTCTACACACCTTTGGCAGACC | 878 |
| SEQ ID NO: 129 | 809 | TTTCCTCCGAAGTTGTAGCTGCATCGTGGGAAGAAGCCTTCTACACACCTTTGGCAGATC | 868 |
| SEQ ID NO: 1 | 1679 | AGTTTCGTGAACTGTTAGTTGGGTTGACTATGTATGGGATGGTATAAGGGTTACCTG | 1738 |
| SEQ ID NO: 130 | 2171 | AGTTTCGTGAACTGTTAGTTGGGTTGATTATGTGTGGGACGGTGTAAGGGTTACCTG | 2230 |
| SEQ ID NO: 131 | 1970 | AGTTTCGTGAACTGTTAGTTGGGTTGACTATGTGTGGGATGGTGTGAGGGGATGGCCTG | 2029 |
| SEQ ID NO: 132 | 2063 | AGTTTCGTGAACTGTTAGTAGGGTTGACTTTGTATGGGATGGTGTGAGGGATTGCCTG | 2122 |
| SEQ ID NO: 133 | 2058 | AGTTTCGTGAACTGTTAGTAGGGTTGACTTTGTATGGGATGGTGTGAGGGATTGCCTG | 2117 |
| SEQ ID NO: 128 | 879 | AGTTTCGTGAACTGTTAGTTGGGTTGATTATGTGTGGGACGGTGTAAGGGTTACCTG | 938 |
| SEQ ID NO: 129 | 869 | AGTTTCGTGAACTGTTAGTAGGGTTGACTATGTATGGGATGGTGTAAGGGATTGCCTG | 928 |
| SEQ ID NO: 1 | 1739 | TTTGTGTTGTGCAACATGTTAATAACAGTGGGGGAGGCTTGGGATTTTGTCCCCATTGCA | 1798 |
| SEQ ID NO: 130 | 2231 | TGTGTTGTGTGCAACATATTAACAATAGTGGGGAGGGTTGGGACTTTGTCCCCATTGCA | 2290 |
| SEQ ID NO: 131 | 2030 | TTTGTGTGTGTGCAGCATATTAATAATATAGTGGGGAGGGTTAGGCCTTTGTCCCTCATTGTA | 2089 |
| SEQ ID NO: 132 | 2123 | TTTGCTGTGTGAACATATTAATAAACAGTGGGGAGGGTTGGGCTTTGTCCCCTTTCATTGTA | 2182 |
| SEQ ID NO: 133 | 2118 | TTTGCTGTGTGAACATATTAATAAACAGTGGGGAGGGTTGGGCTTTGTCCCTCATTGTA | 2177 |
| SEQ ID NO: 128 | 939 | TGTGTTGTGTGCAGCATATTAATAACAGTGGGGAGGGTTGGGACTTTGTCCCCATTGCA | 998 |
| SEQ ID NO: 129 | 929 | TTTGCTGTGTGAACATATTAATAACAGTGGGGAGGGCTTTGTCCCTCATTGTA | 988 |

FIG. 4I

```
SEQ ID NO: 1    1799  TTAATGTGGGGCTTGGTATAATGATGAAGTTTCGAGAATTTACCCCAGATTTGGTGC  1858
                      |||||||||||||||||||||||||||||||||||||||||||||||||||||||||
SEQ ID NO: 130  2291  TTAATGTAGGGCTTGGTATAATGATGAAGTTTCGAGAATTTACCCCAGATTTGGTGC  2350
                      |||||||| ||||||||||||||||||||||||||||||||||||||||||||||||
SEQ ID NO: 131  2090  TTAATGTGGGAGCTTGGTATAATGATGGAAGTTTCGTGAATTTACTCCAGATTTGGTAC  2149
                      |||||||| |||||||||||||||||| ||||||| ||||||||| |||||||||||| 
SEQ ID NO: 132  2183  TTAATGTGGGAGCTTGGTATAATGATGAAATTTAGAGAGTTTACTCCAGACTTAGTGC  2242
                      |||||||| ||||||||||||||||||||  |||| ||||||||| ||||| | |||
SEQ ID NO: 133  2178  TTAATGTGGGAGCTTGGTATAATGATGAAATTTAGAGAGTTTACTCCAGACTTAGTGC  2237
                      |||||||| ||||||||||||||||||||  |||| ||||||||| ||||| | |||
SEQ ID NO: 128  999   TTAATGTAGGGCTTGGTATAATGATGAAATTTCGAGAATTTACCCCAGATTTGGTGC  1058
                      |||||||| |||||||||||||||||||| |||||||||||||||||||||||||||
SEQ ID NO: 129  989   TTCATGTGGGGAGCTTGGTATAATGATGAAATTTAGAGAGTTTACTCCAGACTTAGTGC  1048
                      || |||||||  ||||||||||||||||||  |||| ||||||||| ||||| | |||

SEQ ID NO: 1    1859  GGTGTAGCTGTCATGTAGGAGCTTCTAATCCTTTTCTGTGTTAACCTGCAAAAAATGTG  1918
                      |||||||||||||||||||||||| ||||| || |||||||||||| |||||||||||
SEQ ID NO: 130  2351  GATGTAGCTGCCATGTGGGAGCTTCTAATCCCTTTTCTGTGCTAACCTGCAAAAAATGTG  2410
                       | |||||||| |||| ||||||| ||||| |||||||||| |||||||||||||||||
SEQ ID NO: 131  2150  GGTGCAGTTGCCATGTAGGAGCTTCTAATCCCTTTTCTGTGTTAACCTGCAAAAAATGTG  2209
                      ||||| || || ||||||||||||||||||  |||||||||||||||||||||||||||
SEQ ID NO: 132  2243  GCTGTAGTTGTCATGTAGGAGCCTCTAACCCATTTCTGTGTTAAACTTGTAAAAAATGTG  2302
                      | |||||| |||||||||||| |||||  |||||||||||| || || ||||||||||
SEQ ID NO: 133  2238  GCTGTAGTTGTCATGTAGGAGCCTCTAACCCATTTCTGTGTTAAACTTGTAAGAAATGTG  2297
                      | |||||| |||||||||||| |||||  |||||||||||| || || || ||||||||
SEQ ID NO: 128  1059  GGTGTAGCTGCCATGTGGGAGCTCCTCTAATCCCTCTAACCTGCAAAAAATGTG  1118
                      |||||||||| ||||| |||||| || ||| | |||||||||||||||||||||
SEQ ID NO: 129  1049  GCTGTAGTTGTCATGTAGGAGCCTCTAACCCATTTTCTGTGTTAACCTGTAAAAAATGTG  1108
                      | |||||| |||||||||||| |||||  |||| |||||||||||| ||||||||||||

SEQ ID NO: 1    1919  CTTACCTATCTGGCTTGCAAAGTTTTGTAGATTATGAGTAAAGAAATTGGTAAATGGTGG  1978
                      ||||||||| |||||||||||||| |||| ||||||||||||| ||| |||||| ||||
SEQ ID NO: 130  2411  CTTACCTGTCTGGATTGCAAAGCTTTGTAGAGTTTGTAAAAGTTGGCAAATGGTGG  2470
                      ||||||| ||||| ||||||||  |||||||  || ||||| |||| |||||||||
SEQ ID NO: 131  2210  CTTACTTGTCTGGATTACAGAGTTTTGTGATTATGGATTATGAGTAAAAAAAAGTGGCTGG  2269
                      |||||  |||||| ||||  || |||||| |  || | |||||| |   ||| |  ||||
SEQ ID NO: 132  2303  CTTACCTGTCTGGATTACAAAGTTTTGTAGATTATGAGTAAAACCACTAACAACAAAGTGGTGG  2362
                      ||||| |||||||  ||||||| |||||||||||||||||||  |||||| |  ||| |||||
SEQ ID NO: 133  2298  CTTACCTGTCTGGATTACAAAGCTTTGTAGATTATGAGTAAAACCACTAACAACAAAGTGGTGG  2357
                      ||||| |||||||  |||||||  |||||||||||||||||| |||||| |  ||| ||||||
SEQ ID NO: 128  1119  CTTACCTGTCTGGATTGCAAAGCTTTGTAGATTATGAGTAAAGAAAAGTGGCAAATGGTGG  1178
                      ||||| |||||||  |||||||  |||||||||||||||||| || ||| ||||||||||
SEQ ID NO: 129  1109  CTTACCTGTCTGGTTTACAAAGCTTTGTAGATTATGAGTAAAACCACTGACAAAACCACTGACAAATGGTGG  1168
                      ||||| |||||||  ||| ||||  |||||||||||||||||   |   | |||| ||||||||||||

FIG. 4J
```

```
SEQ ID NO: 1    1979  GAAAGTGATGATAAATTTGCTAAGGACGTGTATAAGCAATTTGTAGAATTTATGAAAAA  2038
                      |||||||||||||||||||||||||||||||||||||||||| |||||||||||||||
SEQ ID NO: 130  2471  GAAAGTGATGATAAATTTGCTAAAAGCTGTGTATCAGCAATTTGTGGAATTTATGAAAAG  2530

SEQ ID NO: 131  2270  GAAAGTGATGATAAATTTGCTAAGGACGTGTATAAGCAATTTGTAGAATTTATGAAAAA  2329
                      ||||||||||||||||||||| ||  ||||||||||||||||||||||||||||||||
SEQ ID NO: 132  2363  GAAAGCAGTGACACAAATTTGCCCCAGGACGTGTATAAGCAGTTTGTGCAATTTATGAAAAA  2422

SEQ ID NO: 133  2358  GAAAGTAATGACACATTGCCCAGGACGTGTATAAGCAATTTGTACAATTTATGAAAAA  2417
                      |||||| |||||  || |||| |||  ||||||||||  |||||| |||||||||||
SEQ ID NO: 128  1179  GAAAGTGATGATAAATTTGCTAAAGCTGTGTATCAGCAATTTGTGGAATTTATGAAAAG  1238

SEQ ID NO: 129  1169  GAAAGTAGTGACAAATTTGCCCAGGACGTGTATAAGCAGTTTGTACAATTTATGAAAAA  1228
                      ||||||| |||| ||||||||  |||||||||||||| ||||| ||||||||||||||
SEQ ID NO: 1    2039  GTTACTGGAACAGACTTAGAGCTTATTCAAATATTAAAAGATCATTACAATATTTCTTTA  2098

SEQ ID NO: 130  2531  GTTACTGGAACAGACTTAGAGCTTATTCAAATATTAAAAGATCATTATAATATTTCTTTA  2590
                      ||||||  |||||||||||||||||||||||||||||||||||||| ||||||||||||
SEQ ID NO: 131  2330  GTTACTGAGACAGACTTAGAGCTTATTCAAATATTAAAAGATCATTACAACATTTCTTTA  2389

SEQ ID NO: 132  2423  GCTACTGGAACAGACTTAGAGCTTAAGAACTTTAAAATTTCAAATTTAAAAGATCATCATTATAACATTTCTTTA  2482
                      | ||||||||||||||||||||||  |   ||||||| |||||||||||||||||   |||| ||||||||||
SEQ ID NO: 133  2418  GTCACTGGTACAGATTTAGAGCTTAGAACTTTAAAATTTCAAATTTAAAAGATCATCATTATAACATTTCTTTA  2477

SEQ ID NO: 128  1239  CTTACTGGAACAGACTTAGAGCTTATTCAAATATTAAAATTTCAAATTTAAAAGATCATTACAATATTTCTTTA  1298
                      |||||||||||||||||||||||||||||||||| |||||||| ||||||||||||| ||| || ||||||||
SEQ ID NO: 129  1229  GCTACTGGAACAGATTTAGAGCTTATTCAAATATTTAAAATTTCAAATTTAAAAGATCATTACAACATTTCTTTA  1288

SEQ ID NO: 1    2099  GATAATCCCTCTAGAAAAACCCATCTTCTTTGTTTGACTTAGTGGCTCGTATTAAAGTAAC  2158
                      |||||||| |||||||||| ||||||| || |||||||||||| ||||||||||| ||||
SEQ ID NO: 130  2591  GATAATCCCCTAGAAAAACCCATCCTCTCCCTGTTGACTTAGTTGCTCGTATTAAAATAAC  2650

SEQ ID NO: 131  2390  GATAATCCCTTAGAAAAACCCATCCTCTTGTTTGACTTAGTTGCTCGTATTAAAAGTAAT  2449
                      |||||||||| |||||||||||| ||||||  |||||||||| |||||||||||||| |
SEQ ID NO: 132  2483  GATAATCCCTTTAGAGAACCCCTCTTCCCTTGACTTAGTTGCTCGCATTAAAAGTAAT  2542

SEQ ID NO: 133  2478  GATAATCCTTTAGAGAACCCCTCTTCCTTATTTGACTTAGTTGCTCGCATTAAAAGTAAT  2537
                      ||||||||  |||||||||| | ||||||||  || |||||| |||||||||||||| |
SEQ ID NO: 128  1299  GATAATCCCCCTAGAAAAACCCATCCTCGTTTGACTTAGTTGCTCGTATTAAAATAAC  1358

SEQ ID NO: 129  1289  GACAATCCCTTTAGAGAAACCCTCTCTTATTTGACTTAGTTGCTCGCATTAAAAGCAAT  1348
```

```
SEQ ID NO: 1    2339 TATGTTGGGCCTGGCAATGAGCTACAAGCTGGGCCCCCAGAGTGCTGTGGACAGTGCT 2398
                    |||||||||||||||||||||||||||||||||||||||||||||||||||||||||
SEQ ID NO: 130  2831 TATGTTGGGCCTGGCAATGAGCTACAAGCTGGGCCCCCGCAAAGTGCTGTTGACAGTGCT 2890
                    ||| ||||||||||||||||||||||||||||||||| ||||||||||| ||||||||
SEQ ID NO: 131  2630 TATATTGGGCCTGGCAATGAGCTACAAGCTGGGCCCCCGCAAAGTGCTGTGTGGATAGTGCT 2689
                    |||||||||||||||||||||||||||||||||||||||||||||||||| ||||||||
SEQ ID NO: 132  2723 TATGTTGGGCCTGGCAATGAGCTACAAGCTGGGCCCTCCGCAAAGTGCTGTGGACAGTGCT 2782
                    ||||||||||||||||||||||||||||||||||| |||||||||||||||||||||||
SEQ ID NO: 133  2718 TATGTTGGGCCTGGCAATGAGTTACAAGCTGGGCCCTCCGCAGAATGCTGTGGACAGTGCT 2777
                    ||||||||||||||||||||| |||||||||||||| |||| ||||||||||||||||||
SEQ ID NO: 128  1539 TATGTTGGGCCTGGCAATGAGCTACAAGCTGGGCCCCCGCAAAGTGCTGTTGACAGTGCT 1598
                    ||||||||||||||||||||||||||||||||||||| |||||||||| ||||||||||
SEQ ID NO: 129  1529 TATGTTGGGCCTGGCAATGAGCTACAAGCTGGGCCTCCGCAGAATGCTGTGGA        1581
                    ||| ||||||||||||||||||||||||||||||||| |||| ||||||||

SEQ ID NO: 1    2399 GCAAGGATTCATGACTTTAGGTATAGCCAACTGGCTAAGCTGGGAATAAATCCATATACT 2458
                    ||||||||||||||||||||||||||||||||||||||||||||||||||||||||||
SEQ ID NO: 130  2891 GCAAGGATTCATGACTTTAGGTATAGCCAACTGGCTAAGCTGGGAATAAATCCATATACT 2950
                    ||||||||||||||||||||||||||||||||||| |||||||||||||||||||||||
SEQ ID NO: 131  2690 GCAAGGATTCATGACTTTAGGTATAGCCAATTGGCTAAGCTGGGAATAAATCCATATACT 2749
                    |||||||||||||||||||||||||||||| |||||||||||||||||||||||||||
SEQ ID NO: 132  2783 GCAAGGATTCATGACTTTAGGTATAGCCAATTGGCTAAGTTGGGAATAAATCCCTTATACA 2842
                    |||||||||||||||||||||||||||||| ||||||| |||||||||| || ||||| 
SEQ ID NO: 133  2778 GCAAGGATTCATGACTTTAGGTATAGCCAATTGGCTAAGTTGGGAATAAAACCCTTATACT 2837
                    |||||||||||||||||||||||||||||| ||||||| ||||||||||  ||||||||
SEQ ID NO: 128  1598 -                                                               1599
                    - 
                    G                                                               1599

SEQ ID NO: 1    2459 CATTGGACTGTAGCAGAGATGAGGAGCTGTTAAAAAATATAAAAAATGAAACTGGGTTTCAA 2518
                    |||||||||||||||||||||||||| |||||||||||||||||||||||||||||||
SEQ ID NO: 130  2951 CATTGGACTGTAGCAGAGATGAAGAGCTTTTAAAAAATATAAAAAATGAAACTGGGTTTCAA 3010
                    |||||||||||||||||||| ||||||  |||||||||||||||||||||||||||||
SEQ ID NO: 131  2750 CATTGGACTGTAGCAGAGATGAAGAACTGTTAAAAAATATAAAAAATGAAACTGGGTTTCAA 2809
                    |||||||||||||||||||| ||| |||||||||||||||||||||||||||||||||
SEQ ID NO: 132  2843 CATTGGACGGTAGCAGAGATGAAGAATTGTTAAAAAATATAAAAAATGAAACAGGGTTTCAA 2902
                    ||||||| |||||||||||| ||||  ||||||||||||||||||||||||| ||||||
SEQ ID NO: 132  2838 CACTGGACGGTAGCAGAGACGAAGAGTTGTTAAAAAATATAAAAAATGAAACAGGGTTTCAA 2897
                    || |||| |||||||||| |||||  ||||||||||||||||||||||||| ||||||
```

FIG. 4M

```
SEQ ID NO:   1   2519  GCTCAAGTAGTAAAAGACTACTTTACTTTAAAAGGTGCAGCTGCCCCTGTGGCCCATTTT  2578
SEQ ID NO: 130   3011  GCACAAGTAGTAAAAGACTACTTTACTTTAAAAGGTGCAGCTGCCCCTGTGGCCCATTTT  3070
SEQ ID NO: 131   2810  GCACAAGCAGTAAAAGATTACTTTACTTTAAAAGGTGCAGCTGCCCCTGTGGCCCATTTT  2869
SEQ ID NO: 132   2903  GCACAAGCAGTAAAAGATTACTTTACTTTAAAAGGTGCAGCTGCCCCTGTGGCCCATTTT  2962
SEQ ID NO: 133   2898  GCACAAGCAGTAAAAGATTACTTTACTTTAAAAGGTGCAGCTGCCCCTGTGGCCCATTTT  2957

SEQ ID NO:   1   2579  CAAGGAAGTTTGCCGGAAGTTCCCGCTTACAACGCCTCAGAAAAATACCCAAGCATGACT  2638
SEQ ID NO: 130   3071  CAAGGAAGTTTGCCGGAAGTTCCCGCTTACAACGCCTCAGAAAAATACCCAAGCATGACT  3130
SEQ ID NO: 131   2870  CAAGGAAGTTTGCCGGAAGTTCCCGCATACAACGCCTCAGAAAAATACCCAAGCATGACT  2929
SEQ ID NO: 132   2963  CAAGGAAGTTTACCGGAAGTGCCCGCGTACAACGCCTCAGAAAAATACCCAGCATGACT   3022
SEQ ID NO: 133   2958  CAAGGAAGTTTACCGGAAGTGCCCGCGTACAACGCCTCAGAAAAATACCCAGCATGACT   3017

SEQ ID NO:   1   2639  TCAGTTAATTCTGCAGAAGCCAGCACTGGTGCAGGAGGGGGGCAGTAATCCTACTAAA    2698
SEQ ID NO: 130   3131  TCAGTTAATTCTGCAGAAGCCAGCACTGGTGCAGGAGGGGGCAGTAATTCTGTCAAA     3190
SEQ ID NO: 131   2930  TCAGTTAATTCTGCAGAAGCCAGCACTGGTGCAGGAGGGCAGTAATCCTGTCAAA       2989
SEQ ID NO: 132   3023  TCAGTTAACTCTGCAGAAGCCAGCACTGGTGCAGGCGGGAGTAGCAACCCTACAAAA     3082
SEQ ID NO: 133   3018  TCAGTTAACTCTGCAGAAGCCAGCACTGGTGCAGGCGGGGAGGAGCAACCTACAAAA     3077

SEQ ID NO:   1   2699  AGCATGTGGAGTGAGGGGCTACTTTTACTGCCAACTCTGTAACTTGTACATTTCCAGA   2758
SEQ ID NO: 130   3191  AGCATGTGGAGTGAGGGGCCACTTTTAGTGCTAACTCTGTAACTTGTACATTTCCAGA   3250
SEQ ID NO: 131   2990  AGCATGTGGAGTGAGGGGCCGCCACTTTTACTGCCAACTCTGTAACTTGTACATTTCCAGA  3049
SEQ ID NO: 132   3083  AGCATGTGGAGTGAAGGGCTACATTACTGCTAATTCTGTAACGTGTACATTCTCTAGG  3142
SEQ ID NO: 133   3078  AGCATGTGGAGTGAAGGGCTACATTTACTGCTAATTCTGTAACATGCACATTCTCTAGG  3137
```

```
SEQ ID NO:   1   2999  ATATCAGAAATTGCCATTAAAGATGTTACAGACAAAACTGGAGGAGGGTACAGGTTACT  3058
                       |||||||||||||||||||||||||||||||||||||||||||||||||||||||||||
SEQ ID NO: 130   3491  ATATCAGAAATTGCTGTTAAGGATGTTACAGACAAAACTGGAGGGGGGTACAGGTTACT  3550
                       ||||||||||||| |||||| ||||||||||||||||||||||| || ||||||||||
SEQ ID NO: 131   3290  ATATCAGAAATTGCTGTGTAAAAGATGTTACAGACAAAACTGGAGGAGGGTGCAGGTTACT  3349
                       ||||||||||||| || |||||||||||||||||||||||||||| || ||||||||
SEQ ID NO: 132   3383  ATTTCAGAAATTGCTGTGTAAAAGATGTCACAGACAAAACAGGAGGAGAGTGTGCAAGTTACT  3442
                       || ||||||||||| ||||||||||| ||||||||||| |||||||||||| |||||||
SEQ ID NO: 133   3378  ATTTCAGAAATTGCTGTGTTAAAAGATGTTACAGACAAAACAGGAGGAGAGTGTGCAAGTAACT  3437

SEQ ID NO:   1   3059  GACAGTACTACAGGGCGTTTATGCATGTTAGTAGACCATGAATACAAGTACCCATATGTA  3118
                       |||||||||||||||||||||||||||||||||||||||||||||||||||||||||||
SEQ ID NO: 130   3551  GACAGCACTACAGGGCGCCTATGCATGTTAGTAGACCATGAATACAAGTACCCATATGTG  3610
                       ||||| ||||||||||| | |||||||||||||||||||||||||||||||||||||| 
SEQ ID NO: 131   3350  GACAGTACTACAGGGCGTTTATGCATGTTAGTAGATCATGAGTACAAGTATCCATATGTG  3409
                       |||||||||||||||||||||||||||||||||| |||||| |||||||| ||||||| 
SEQ ID NO: 132   3443  GACAGCACCACAGGACGTTTGTATGTTAGTGGATCATGAGTATAAATACCCATATGTG  3502
                       ||||| || |||||| ||||| |||||||| || ||||| || |||| |||||||| 
SEQ ID NO: 133   3438  GACAGCACCACAGGACGTTTGTATGTTAGTGGACCATGAATATAAGTACCCATATGTG  3497

SEQ ID NO:   1   3119  TTAGGTCAAGGACAAGATACCTTAGCCCCAGAGCTTCCAATTTGGGTGTACTTTCCACCT  3178
                       |||||||||||||||||||||||||||||||||||||||||||||||||||||||||||
SEQ ID NO: 130   3611  TTAGGGCAAGGTCAGGATACTTTAGCCCCAGAACTTCCTATTTGGGTATACTTTCCCCCT  3670
                       ||||| |||||  ||||||| |||||||||||| ||||| |||||||| |||||| |||
SEQ ID NO: 131   3410  TTAGGTCAGGGACAGGATACCTTAGCCCCAGAACTTGCCTATTTGCCTATTTGGGTGTACTTTCCCCCT  3469
                       ||||||||  || |||||||||||||||||||| ||| | ||||| || ||||||||||| ||
SEQ ID NO: 132   3503  CTAGGTCAGGGACAAGACACACTAGCTCCAGAACTGCCCATTTGGGTTACTTTCCCCCC  3562
                       |||||||| ||| ||||  ||| |||| ||||| ||| ||||||| ||||| |||| 
SEQ ID NO: 133   3498  CTGGGTCAGGGACAAGACACACTAGCTCCAGAACTGCCTATTTGGGTACTTTCCTCCC  3557

SEQ ID NO:   1   3179  CAATATGCTTACTTAACAGTAGGAGATGTAAACACGCAGGAATTTCTGGGACAGTAAA  3238
                       |||||||||||||||||||||||||||||||||||||||||||||||||||||||||
SEQ ID NO: 130   3671  CAATATGCTTACTTAACAGTAGGAGATGTTAACACAAGGAATTTCTGGAGACAGCAAA  3730
                       ||||||||||||||||||||||||||||| |||||  ||||||||||| |||| |||
SEQ ID NO: 131   3470  CAATATGCTTATTTAACCGTGGGAGATGTAAACACACAGGAATTTCAGGGACAGTAAA  3529
                       ||||||||||| ||||| ||| |||||||||||||| ||||||||| ||||||||||
SEQ ID NO: 132   3563  CAGTATGCTTACTTAACAGTAGGTGAAGTAAACAAGAAGAGTTTCAGGAGACAGCAAA  3622
                       || |||||||| ||||||||| || || ||||||   ||| ||||  ||||| ||||
SEQ ID NO: 133   3558  CAGTATGCTTACTTAACAGTAGGTGAACTAAACACAAGAGAGTTTCAGGAGACAGCAAA  3617
```

FIG. 4P

```
SEQ ID NO: 1     3239 AAAATTAGCTAGTGAAGAATCAGCGTTTATGTCCTGGAACACAGCTCTTTTGAACTTTTA 3298
                      |||||||||||||||||||||||| |||||||||||||||||||||||||| ||||||||
SEQ ID NO: 130   3731 AAAATTAGCAAGTGAAGAATCAGCATTTATGTTTTGGAACACAGTTCTTTTCAGCTTTTA 3790
                      ||    |||| |||||||||||||  |||||| |||||||||||| ||||| ||||| |
SEQ ID NO: 131   3530 AAGCTAGCAAGTGAAGAATCAGCATTTTATGTTTTGGAACACAGTTCATTTGAACTGTTA 3589
                      || ||  ||| ||||||||||||| ||||||| | ||||| ||||| ||||||||| ||
SEQ ID NO: 132   3623 AAATTGGCTAGTGAAGAATCAGCTTTTTTATGTGTTAGAGCACAGTTCATTTGAACTTTG 3682
                      |||||  ||||||||||||||||  ||||||||  |||| |||||| ||||||||||
SEQ ID NO: 133   3618 AAATTGGCTAGTGAAGAATCAGCTTTTTATGTTTTGGAACACAGCTCCTTTCAACTTTTA 3677

SEQ ID NO: 1     3299 GGTACAGGGGGCTCTGCTACTATGTCTTATAAGTTCCCTCCAGTGCCCCCAGAGAATTTA 3358
                      |||||||| |||||||| |||||||||||| ||| | |||||||||||||||| |||||
SEQ ID NO: 130   3791 GGTACAGGAGGAGTACAGCATCTATGTCTTATAAGTTCCTCCAGTGCCCCAGAAAATTTA 3850
                      |||||||| || ||| ||  |||||||||||||||| | ||||||||||||| |||||
SEQ ID NO: 131   3590 GGTACAGGGTGTGGCTCTCTGCCACTATGTCCTATAAATTCCACCAGTGCCCCCAGAAAAACTTG 3649
                      |||||||| || | |||| ||||  |||||| ||||| |||  |||||||||||| ||||| |
SEQ ID NO: 132   3683 GGTACAGGGGGATCTGCCAACATGTCCTACACAATGTCCTATAAATTTCCAGCTGTGCCCCCAGAAAACCTA 3742
                      ||||||||  | |||| ||| |||| || ||||||||| |||| ||||||| ||||||||||  |||| |
SEQ ID NO: 133   3678 GGTACAGGTGGCTCTGCTACTATGTCCTACAATGTCCTATAAATTTCCAGCCCGTGCCCCCAGAAAACTTA 3737

SEQ ID NO: 1     3359 GAAGGCTGTAGTCAACACTTTATGAAATGTACAACCCGTTATATGGATCCCGTTTAGGA 3418
                      ||  |||| ||||| | ||||||||||||||| ||| |||| | | ||| ||| ||||
SEQ ID NO: 130   3851 GAGGGCTGCAGTGAACACTTTTATGAAATGTACAATCCCTTATACGGATCCCGCTTAGGG 3910
                      ||  ||||  || ||  ||||||||||||| |||| ||| ||| |||| | ||||||||
SEQ ID NO: 131   3650 GAGGGTTGTAGCCAACACTTTTATGAAATGTACAACCCCCTGTATGGGTCTCGTTTAGGG 3709
                      ||| | ||  | || ||||||||||||||| ||| ||||  ||  | |||  |||||||
SEQ ID NO: 132   3743 GAAGGCTGCAGCCAACATTTTTATGAAATGTACAACCCTTTGTACGGTTCTCGTTTAGGG 3802
                      ||||| ||||| || | ||  |||||||||||| |||| || | ||| | |||||||||
SEQ ID NO: 133   3738 GAGGGCTGCAGCCATTTTTATGAAATGTACAACCCCCTGTATGGTTCTCGTTTAGGA 3797

SEQ ID NO: 1     3419 GTCCCTGATACATTAGGAGGGGACCCCAAATTTAGATCTTTAACACATGAAGACCACGCA 3478
                      || ||||||||| ||||||| ||||| ||||||||||| |||||||| ||||| || ||
SEQ ID NO: 130   3911 GTTCCTGACACATTAGGAGAGTGACCCAAAATTTAGATCTTTAACACATGAAGACCATGCA 3970
                      || |||||||| ||||||  ||||||||||||||||||||||||| | | |||||||||
SEQ ID NO: 131   3710 GTACCTGACACACTAGGGGGGACCCTAAATTTAGATCATTAACTCACGAAGATCATGCA 3769
                      |  |||||||| ||||| | |||||||||||||||| ||||| || ||||| |||||
SEQ ID NO: 132   3803 GTGCCTGACACATTAGGAGGGGACCCTAAATTTAGATCATTGACACACGAAGACCACGCA 3862
                      || |||||||| ||||| | ||||| ||||||||| | ||| || || |||| || |||
SEQ ID NO: 133   3798 GTGCCTGACACATTAGGAGGGGACCCTAAATTTAGATCATTAACACACGAGACCACGCA 3857
```

```
SEQ ID NO: 1     3719  GAAGACAAAGAGTATCAACAGGGCGTGGGTAGGTTTCCCAATGAAAAGAACTAAAA      3778
                       ||||||||||||||||||||||||||||||||||||||||||||||||||||||||
SEQ ID NO: 130   4211  GAAGACAAAGAGTATCAGCAAGGAGTGGGTAGATTTCCAAATGAAAAAGAACAGCTAAAA  4270
                       |||||||||||||||||  |||| ||||||||| |||||||||||| ||||| ||||||
SEQ ID NO: 131   4010  GAAGACAAAGAGTATCAGCAAGCAAGGGGTAGGAAGATTCCAAATGAAAAAGAGCAACTTAAA  4069
                       |||||||||||||||||  || || ||||||| || || ||||||||||| || || |||
SEQ ID NO: 132   4103  GAGGACAAAGAGTATCAGCAAGCAAGGGGTAGGAAGATTCCAAATGAAAAAGAAGAACAGCTTAAG  4162
                       || |||||||||||||||  || || ||||||| || || ||||||||||| ||||| || |||
SEQ ID NO: 133   4098  GAAGACAAAGAGTATCAGCAAGCAAGGGGTAGGAAGGTTTCCAAATGAAAAAGAAAAAGAACAACTTAAG  4157
                       |||||||||||||||||  || || ||||||| || ||||||||||||||| |||||||||| |||

SEQ ID NO: 1     3779  CAGTTACAGGGTTTAAATATACACACATATTTCCCAATAAAGGTACCCAGCAATATACA  3838
                       ||||||||||||||||||||||||||||||||||||||||||||||||||||||||||
SEQ ID NO: 130   4271  CAGTTACAGGGTTTAAACATGCACACCTACTTTCCAATAAAGAACCCAGCAATATACA  4330
                       ||||||||||||||||| || |||||  | |||||||||||| ||||||||||||||
SEQ ID NO: 131   4070  CAGTTACAAGGCCTAAACATTCACACATACTTTCCAAACAAAGGAACAATACACA  4129
                       |||||||| ||  ||||||| ||||| | ||||||| |||||  |||| |||||
SEQ ID NO: 132   4163  CAGTTACAAGGTCTTAACATGCACACATACTTCCCTAATAAAAGGAACCAACAATACACA  4222
                       |||||||| || ||||||| ||||| | ||| ||  ||||||  |||||||||||||
SEQ ID NO: 133   4158  CAGTTACAAGGGCTAAACATGCACACATACTTTCCTAATAAAAGGTACCAACAATACACA  4217
                       |||||||| ||  ||||||| |||| | ||||||  |||||||| ||||||||||||

SEQ ID NO: 1     3839  GATCAAATTGAGCGCCCCCTAATGGTAGGCTCTGTATGGAACAGAAGAGCCCTTCACTAT  3898
                       ||||||||||||||||||||||||||||||||||||||||||||||||||||||||||
SEQ ID NO: 130   4331  GATCAAATTGAGCGCCCCCCTAATGTGGTTCTGTATGGAACAGAAGAGCCCTTCACTAT  4390
                       |||||||||||||||||| ||||||  || ||||||||||||||||||||||||||||
SEQ ID NO: 131   4130  GATCAAATTGAACGCCCCCTAATGTAATGGTAGGGTCTGTGTGGAACAGAGCTCTTCATTAT  4189
                       ||||||||||| ||||||||||||  ||| ||| ||||| |||||||||| ||||| |||
SEQ ID NO: 132   4223  GACCAAATTGAACGCCCCTCTTATGTGGCTCTGTGTGGAACAGAGAGCTCTTCACTAT  4282
                       || ||||||||| ||||| | |||| ||| |||| |||||||| ||| ||||| |||
SEQ ID NO: 133   4218  GATCAAATTGAAAGACCTTTAATGTGGGCTCTGTGTGGAACAGAGAGCTCTTCACTAT  4277
                       ||||||||||| || ||| ||||| || ||||| |||||||||| ||| ||||| |||

SEQ ID NO: 1     3899  GAAAGCCAGCTGTGGAGTAAAATACCAAATTTAGATGACAGCTTAAAACTCAGTTGCA  3958
                       |||||||||||||||||||||||||||||||||||||||||||||||||||||||||
SEQ ID NO: 130   4391  GAAAGCCAGCTGTGGAGTAAAATTCCAAATTTTAAAACTTCAGTTTGCA  4450
                       ||||||||||||||||||||||| |||||||| || |||||||| | |
SEQ ID NO: 131   4190  GAGAGTCAGCTGTGGAGTAAAATCCCCAACTTAGATGACAGTTTTAAAACCCAATTTGCA  4249
                       || || ||||||||||||||||| ||  || |||||||||| ||||||| ||||||||
SEQ ID NO: 132   4283  GAAAGTCAGCTGTGGAGTAAATCCCTAACTTAGATGACAGTTTTAAAACTCAATTTGCA  4342
                       || || |||||||||||||| ||| |||||||||||||| |||||||| |||||||
SEQ ID NO: 133   4278  GAAAGTCAGTTATGGAGTAAAATCCCTAACTTAGATGATAGTTTTAAAAACTCAATTTGCA  4337
                       || ||||| | ||||||||||| ||| ||||||||| || |||||||  |||||||||
```

FIG. 4S

```
SEQ ID NO: 1     3959  GCTTTAGGAGGTTGGGACTACATCAGCCACCACCCCCTCAAATATTTTTAAAAATATTACCA  4018
                       || ||||||||||||||||||||||||||| ||||||||||||||||| ||||||||||||
SEQ ID NO: 130   4451  GCCTTAGGAGGATGGGGTTTGCATCAGCAGCCACCTCCTCAAATATTTTTAAAAATATTACCA  4510

SEQ ID NO: 131   4250  GCCCTGGGCGGGCTGGGGTTTACATCAACCACCACCCCCTCAAATATTTTTAAAAATACTGCCA  4309
SEQ ID NO: 132   4343  GCCCTAGGCGGGTGGGGTTTGCATCAACCACCACCCCCTCAAATATTTTTAAAAATACTACCA  4402
SEQ ID NO: 133   4338  GCGTTAGGCGGGTGGGATTGCACCAACCACCCCCTCAAATATTTTTAAAAATACTACCG  4397

SEQ ID NO: 1     4019  CAAAGTGGGCCAATTGGGCGTATTAAGTCAATGGAATAACACATTAGTTCAATATGCT  4078
SEQ ID NO: 130   4511  CAAAGTGGGCCAATTGGAGGTTATTAAATCAATGGAATTACTACCTTAGTTCAGTATGCC  4570

SEQ ID NO: 131   4310  CAAAGTGGACCAATTGGGGTATTAAATCCATGGAATCACTACCCTAGTTCAATATGCA  4369
SEQ ID NO: 132   4403  CAAAGTGGGCCAATTGGGGTATTAAATCCATGGAATTACTACTTAGTTCAATATGCT  4462
SEQ ID NO: 133   4398  CAAAGTGGGCCCATTGGAGGTATTAAATCCATGGAATTACTACTTAGTTCCAGTATGCT  4457

SEQ ID NO: 1     4079  GTGGGTATTATGACAGTAACTACTATGACATTAAATTAGGGCCTCGCAAAGCTACAGGACGG  4138
SEQ ID NO: 130   4571  GTGGGAATTATGACAGTAACTAACTATGACATTAAATTGGGGCCCCGTAAAGCTACGGGACGG  4630

SEQ ID NO: 131   4370  GTGGGAATTATGACAGTAACTACTACTATGACATTAAATTTAAATTGGGACCTGTAAGGCTACTGGTAGG  4429
SEQ ID NO: 132   4430  GTGGGAATTATGACAGTAACTACTACCATGACCTTTAAATTGGGACCTCGAAAGGCTACTGGAAGG  4522
SEQ ID NO: 133   4458  GTAGGAATTATGACAGTCACTATGACATTAAATTGGGACCTCGAAAAGCCACTGGAAGG  4517

SEQ ID NO: 1     4139  TGGAATCCTCAACCTGGAGTGTACCCTCCTCACGCAGCAGGCCATTTACCATATGTACTA  4198
SEQ ID NO: 130   4631  TGGAATCCTCAACCTGGAGTATATCCCCCGCACGCAGCAGTCATTTACCATATGTACTA  4690

SEQ ID NO: 131   4430  TGGAATCCACAGCCTGGAGTGTATCCTCCTCATGCAGCTGGTCAGCTCATTTACCATATGTACTG  4489
SEQ ID NO: 132   4523  TGGAATCCCCAGCCTGGCGTTTATCCTCCTCATGCAGCTGGTCAGCTCATTTACCATATGTACTG  4582
SEQ ID NO: 133   4518  TGGAATCCTCAACCTGGAGTTTACCCTCCTCATGCAGCTGGTCAGCTCATTTACCATATGTACTG  4577
```

FIG. 4T

| | | | | |
|---|---|---|---|---|
| SEQ ID NO: 1 | 4199 | TATGACCCCACAGCTACAGATGCAAAGCAACACCACAGACACATGGATATGAAAAGCCTGAA | 4258 |
| SEQ ID NO: 130 | 4691 | TATGACCCCACAGCTACAGATGCAAAGCAAAACAACACCACAGACACATGGATATGAAAAGCCTGAA | 4750 |
| SEQ ID NO: 131 | 4490 | TATGACCCTACAGCTACAGATGCAAAGCAAACCAACACCACAGACACGGATATGAAAAGCCTGAA | 4549 |
| SEQ ID NO: 132 | 4583 | TATGACCCCACAGCTACAGATGCAAAGCAACACCACAGACAACGGATATGAAAAGCCTGAA | 4642 |
| SEQ ID NO: 133 | 4578 | TATGACCCCACAGCTACAGATGCAAAGCAACAACACCACAGACACGGATATGAAAAGCCTGAA | 4637 |
| SEQ ID NO: 1 | 4259 | GAATTGTGGAC | 4269 |
| SEQ ID NO: 130 | 4751 | GAATTGTGGACA | 4762 |
| SEQ ID NO: 131 | 4550 | GAATTGTGGAC | 4560 |
| SEQ ID NO: 132 | 4643 | GAATTGTGGACT | 4654 |
| SEQ ID NO: 133 | 4638 | GAATTGTGGACT | 4649 |

FIG. 4U

```
PVBAUA       (1)    GAATTCCGCCAAATCAGATGCCGCCGGTTGCCGCGGTGTAGGGGGACTTCCGGTACAAGATGGGCGGACAATTACGTCATTTCCTGTGACG
Consensus  (181)    -------------------------------------C--------------------------------------------------

PVBAUA      (91)    TCATTTCCTGTGACGTCACAGGAAATGACGTAATTGTCCGCCATCTGTACCGGAAGTCCCGCCTACCGGGGCGACCGGCGGCATCTGA
Consensus  (271)    ----------------------------------------------------------------------------------------

PVBAUA     (181)    TTTGGTGTCTTCTTTAAATTTAGCGGGCTTTTTTCCCGCCTATGCAAATGGGCAGCCATTTAAGTGTTTACTATAATTTATTGG
Consensus  (361)    ----------------------------TTT-------------T--------TT---T---T--T-T---

PVBAUA     (271)    TTAGTTTGTAACGGTTAAAATGGGGCGGTAGGCGGAGCGTAGGCGGGGACTACAGTATATATAGCACGTACTGCCGCAGCTCTTTCTTTCTGGCT
Consensus  (451)    ---TT---A------AA--G----A--G--GG-G------GTATATA----------T-

```
PVBAUA    (991) AATGATACTAGTAGTGATGCTGGGGAGTCTAGCGGCACAGGGCAGAGTTGTGCCATTTAATGGGAAGGAACTAAGGCTAGCATAAAG
Consensus(1171) -A------TA-TGA---GG-GA-TC-AGC-G---AGGGG-AGA-GT-GT-CCATT---GG-AA-GG-AC-AA-GC--G---TAAAG PVBAUA   (1081) TTTCAAACTATGGTAAACTGGTTGTGTGAAAACAGAGTGTTTACAGAGATAAGTGAAAACTAGTGACTTTAACCAGTACACTTTACTA
Consensus(1261) TTTCA-AC-ATGGTAAA-TGG-T-TGTGAAAA-AGAGT-TTTAC-GA-GA-AA-TGGAA---AGT-GA-TT-AA-CA-TA-AC-TTA-TA PVBAUA   (1171) AGCAGTAGTCACAGTGGAAGTTTCAAATTCAAAGTGCACTAAAACTAGCAATTTATAAAGCAACTAATTTAGTGCCTACTAGCACATTT
Consensus(1351) AG-AG-AGTCA-AGTGG-AG-TTTCAAAT-CAAAGTGC--TAAA--T-GC-AT-TA-AA-GC-AC-AA-TT-GT-CC-AC-AG-AC-TT- PVBAUA   (1261) TTATTGCATACAGACTTTGAGCAGGTTATGTGTATTAAAGACAATAAAATTGTTAAAATTGTTACTTTGTCAAAACTATGACCCCTATTG
Consensus(1441) TT--T-CAT-CAGACTTTGAGCAGGTTA--TG-ATTAAGA-AATAAAAT-GT-AAAA-T-TTA-T-TG-CA-AA-TATGA-CC-CT--T-

PVBAUA   (1351) GTGGGGCAGCATGTGTTAAAGTGGATTGATAAAAATGTGTAAGAAAAATACACTGTGGTTTTATGGCCGCCAAGTACAGGAAAAACA
Consensus(1531) GT-GG-CA-CATGT-TTAA-GTGGATTGA-AAAAATGTGG--AA-AAAA-AC--T-TGGTTTTA-GGGCC-CC-AG-AC-GGAAAAACA PVBAUA   (1441) AACTTGGCAATGGCCATTGCTAAAAGTGTTCCAGTATATGGCATGTGTTAACTGGAATAATGAAAACTTTCCATTTAATGATGTAGCAGGA
Consensus(1621) AA-TT-GC-ATGGC-ATTGC-AAAA-TGT-CC-GT-TATGG-ATGGT-AA-TGGAA-AATGAAAA-TTTCCATTTAATGATGT-GC-GG- PVBAUA   (1531) AAAAGCTTGGTGTGGTCTCTGGGATGAAGGTATTATTAAGTCTACAATTGTGTAGAAGCTGCAAAAGCCATTTTAGGCGGCAACCCACCAGGGTA
Consensus(1711) AAAAG-TTGGTGGTCTCTGGGATGAAGG-AT-ATTAAGTC-AC-ATTGT-GAAGCTGCAAAAGC-ATT-TAGG-GG-CA-CC--ACCAGGGTA PVBAUA   (1621) GATCAAAAAAATGCGTAGCACTGG-AGTGT-GC-GTGCC-GG-GT-CC-GTGGT-ATAA-CCAGCAA-GGTGACATTAC-TTTGTTGT-AG-GG-AA
Consensus(1801) GATCA--AAAATGCGTG-AGTGT-GC-GTGCC-GG-GT-CC-GTGGT-ATAA-CCAGCAA-GGTGACATTAC-TTTGTTGT-AG-GG-AA PVBAUA   (1710) CACTACAACAACTGTACATGCTAAAGCCTAAAAGCCTAAAAGAGCGCATGGTAAAGTTAAACTTTACTGTA  AGATGCAGCCCTGACATGGGGTTA
Consensus(1891) -AC-AC-ACAACTGT-CATGCTAAAGC-CATGCTAAAAGCCTAAA-GA--G-ATGGTAAAG-TAAA-TTTAC--TA--AG-TG-AGCCCTGACATGGG-TTA PVBAUA   (1798) CTAACAGAGGCTGATGTACAACAGTGCTTACATGGTGTAATGCACAAAGCTGGGACCACTATGAAAACTGGGCAATAAAACTACACTTTT
Consensus(1981) CT-ACAGAGGCTGATGT-CA-CA-TGGCT-AC-TG----A--AAGCTGG---CCACTAATGAAA-CTGGGCAATAATAAACTACAC-TTT PVBAUA   (1888) GATTTCCCTGGAATTAATGCAGATGCAGATGCCCTCCACCCAGACCTCCAAACCACCCCCAATTGTCACAGACACCCAGTATCAGCAGCAGTGGTGGT
Consensus(2071) GATTTCCCTG-GAAT-AATGCAGATGCCCTGCACCTCCACCAGA-CTCCAAACC--CCC-ATTGTC-CAGACACCAGT-TCAGCAGCAGTGGTGGT PVBAUA   (1978) GAAAGCTCTGAAGAACTCAGTGAAAGCAGCTTTTTTTAACCTCATCACCCCAGGCGCCTGAACACTGAAACCCGCGCTCTAGTACGCCC
Consensus(2161) GAAAGCTCTGAAGAACTCAGTGAAAGCAGCTTT-T-AACCTCATCAC-CCAGGCGCCTGAACA-TGAAACCCGCGCTCTAGTAC-CCC
```

FIG. 5B

```
PVBAUA     (2068)  ATCCCCGGGACCAGTTCAGGAGAATCATTTGTCGGAAGCCCAGTTCCTCCGAAGTTGTAGCTGCATCGTGGGAAGAAGCCTTCTACACA
Consensus  (2251)  -TCCCCGGGACCAGTTCAGGAGAATCAT-TGTCGGAAGC-CAGTTCCTCCGAAG--GTAGC-GC-TCGTGGGA-GAAGC-TT-TACAC- PVBAUA     (2158)  CCTTTGGCCAGAGACCAGTTTCGTGAACTGTTAGTTGGGGTTGATTATGTGTGGGACGGTGTAAGGGGTTTACCTGTGTGTTGTGCAACAT
Consensus  (2341)  CC--T-GCAGA-CAGTTTCGTGAACTGTTAGT-GGGTTGA-T-TGT-TGGGA-GGTGT-AGGGG-TT-CCTGT-TG-TGTGT--A-CAT PVBAUA     (2248)  ATTAACAATAGTGGGGGAGGGTTGGGACTTTGTCCCCATTGCATTAATGTAGGGCTTGGTATAATGGATGGAAATTTCGAGAATTTACC
Consensus  (2431)  AT-AA-AA-AGTGGGGGAGG-TT-GG-CTTTG--CC--A-TG-ATTAATGT-GG-GCTTGGTATAATGGATGGAA-TTT-GAGA-TTTAC- PVBAUA     (2338)  CCAGATTTGGTGCGATGTAGCTGCCATGTGGGAGCTTCTAATCCCTTTTCTGTGCTAACCTGCAAAAAATGTGCTTACCTGTCTGATTG
Consensus  (2521)  CCAGA-TT-GT--CG-TG-AG-TG-CATGT-GGAGC-TCTAA--CC-TTTTCTGTG-T-AC-TG-AA-AAATGTGCTTAC-TGTCTGGATT- PVBAUA     (2428)  CAAAGCTTTGTAGATTATGAGTAAAAAAGTGGCAAATGTGGGAAAGTAGTGATGATAAATTTGCTAAAGCTGTGTATCAGCAATTTGTGGA
Consensus  (2611)  CAAAG-TTTGT-GATTATGAGTAA----A-T---A-ATGGTGGGAAAGT--TGA-A-ATTTGC--A-G--GTGTAT-AGCA-TTTGT--A PVBAUA     (2518)  ATTTTATGAAAAGGTTACTGGAACAGACTTAGAGCTTATTCAAATATTAAAAGATCATTATATATTTCTTTAGATAATCCCCTAGAAAA
Consensus  (2791)  CCC-TC--TC--T-TTTGACTTAGTTGCTCG-ATTAAAA--AA-CTTAAA-A

| PVBAUA | (3226) | CTCTGTAACTTGTACATTTCCAGACAGTTTTTAATTCCATATGACCCAGAGCACCATTATAAGTGTTTTCTCCCGCAGCGAGTAGCTG |
|---|---|---|
| Consensus | (3421) | -TCTGTAAC-TG-ACATT-TC-AG-CA-TTTTAAT-CC-TATGA-CCAGAGCA-CATTATAA-GT-TT-TCTCC-GCAGC-AG-AG-TG |
| PVBAUA | (3316) | CCACAATGCCAGTGGAAAGGAGGCAAAGTTTGCACCATCAGTCCCATAATGGATACTCAACCCCATGGAGATATTTAGATTTTAATG |
| Consensus | (3511) | CCA-AATGC-AGTGG-AA-GAGGCAAA-GT-TGCAC-ATTAG-CC-AT-ATGGG-TACTC-AC-CC-TGG-GATA-TTAG

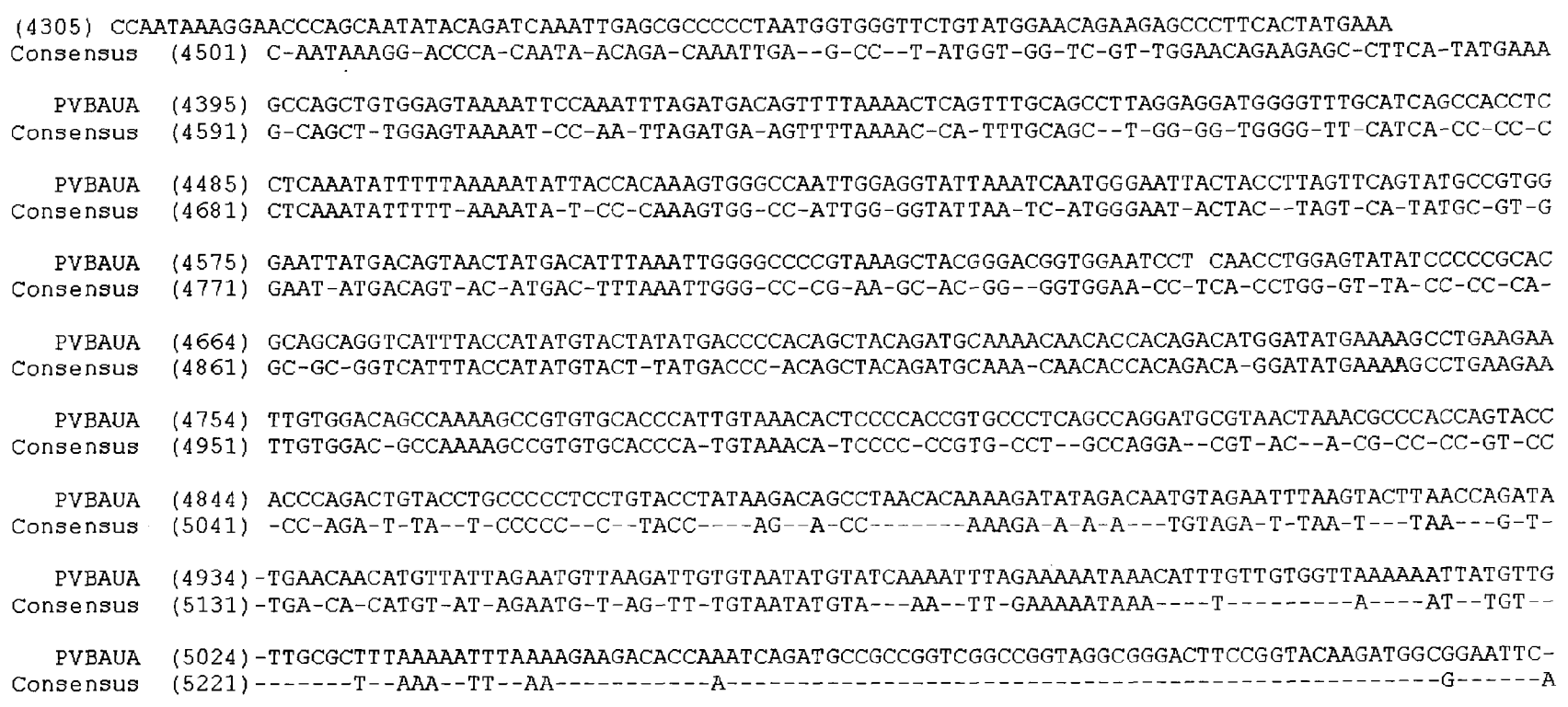

```
(4305) CCAATAAAGGAACCCAGCAATATACAGATCAAATTGAGCGCGCCCCCTAATGGTGGGTTCTGTATGGAACAGAAGAGCCCTTCACTATGAAA
Consensus

PVBAUA    (4395

FIG. 6

```
PVBAUA     (3704) ACACAAGGAATTCTGGAGACAGCAAAAAATTAGCAAGTGAAGAATCAGCATTTTATGTTTGGAACACAGTCTTTTCAGCTTTTAGGTACAGGAGGTA
Consensus  (3900) ACACA GG   T TC GG GACAGG AAAAAA T GC AGTGAAGAATCAGC TTTTATGT    T GA CACAG TC TTT A CT  T GG ACAGG GG PVBAUA     (3804) CAGCATCTATGTCTTATAAGTTTCCTCCAGTGCCCCCAGAAAAATTTAGAGGGCTGCAGTGACAGTCAACACTTTTATGAATGTACAATCCCTTATACGGATCCCG
Consensus  (4000) C GC A  ATGTC TA AA TTTCC  C GT CC CCAGAAA  T GA GG TG AG CA CA TTTTATGA ATGTACAA CC    T TA GG TC CG PVBAUA     (3904) CTTAGGGGTTCCTGACACATTAGGAGGTGACCCAAATTAGATCTTTAACACATGAAGACCATGCAATTCAGCCCAAAACTTCATGCCAGGGCCACTA
Consensus  (4100) TTAGG GT CCTGACACA TAGG GG GACCCC AAATT AGATC   T AC CA GA GA CA GCAATTCAGCC CA AA TT ATGCC GG CCACT PVBAUA     (4004) GTAAACTCAGTGTCTACAAAGGAGGAGACAGCTCTAATACTGGAGCTGGAAAAGCCTTAACAGGCCTAGCACAGTACCTCTCAAAAACACTAGAATAT
Consensus  (4200) T AA TCAGT TC AC AA GA GGAGA A  TC A TAC GG GC GG AAAGCC T AC GG CTTAG AC GG AC       CAAA  AC AGAAT T PVBAUA     (4104) CCTTACGCCCTGGGCAGTGTCTCAGCCATACCACCACGAGTGGTAGATTTCCAAATGAAAAGAACAGCTAAAACAGTTACAGGGTTTAAACATGCACACCTACTTT
Consensus  (4300) CC T CGCCC GG CCAGT TC CGCCC TA CA CACTGGGCAC GATAA TATGT ACAGGAATAAA GC ATTTC C

FIG. 9

| Target Region | Function | Name | SEQ ID NO: | Sequence | Tm |
|---|---|---|---|---|---|
| 1 | Forward primer | B19_2043F | 136 | TGAAACCCGCGCTCTA | 59.6 |
| 1 | Reverse primer | B19_2171R | 137 | AACTAACAGTTCACGAAACTG | 56.7 |
| 1 | Detection probe | B19_2069F_FAM | 138 | TCCCCGGGACCAGTTCAGGAGAA | 68.1 |
| | Forward primer | B19_1962F | 139 | TCAGCAGCAGTGGTGGT | 59.6 |
| | Reverse primer | B19_2043R | 140 | TAGAGCGCGGGGTTTCA | 59.6 |
| 2 | Detection probe | B19_1979F-FAM | 141 | TGAAAGCTCTGAAGAACTCAGTGAAAGCAGCTTT | 67.0 |
| 2 | Forward primer | B19_1903F | 142 | AATGCAGATGCCCTCCAC | 59.9 |
| | Detection probe | B19_1962F-FAM | 143 | TCAGCAGCAGTGGTGGTGAAAGCTCTGAA | 68.9 |
| | Reverse primer | B19_2027R | 144 | TGTTCCAGGCGCCTG | 58.9 |
| | Forward primer | B19_4700F | 145 | CACGCTACAGATGCAAA | 55.3 |
| | Reverse primer | B19_4769R | 146 | GGTGCACACGGCTTTT | 56.7 |
| 3 | Detection probe | B19_4733R_FAM | 147 | TGTCCACAATTCTTCAGGCTTTTCATATCC | 64.6 |
| 3 | Detection probe | B19_4733F_FAM | 148 | TGGATATGAAAAGCCTGAAGTATTGTGGAC | 64.6 |
| | Forward primer | B19_4672F | 149 | GGTCATTTACCATATGTACT | 54.2 |
| | Detection probe | B19_4703F-FAM | 150 | AGCTACAGATGCAAA5NICAACACCACAGACA | 66.7 |
| 4 | Forward primer | B19_1500F | 151 | GAAAACTTTCCATTTAATGATGT | 53.8 |
| 4 | Reverse primer | B19_1631R | 152 | ATTTTTGATCTACCCTGGT | 54.2 |
| | Detection probe | B19_1537F-FAM | 153 | TTGGTGGTCTGGGATGAAGG | 62.4 |
| 5 | Forward primer | B19_1411F | 154 | GTTTTATGGGCGCCAAGTA | 60.4 |
| | Reverse primer | B19_1537R | 155 | TTCATCCCAGACCACCAAGG | 62.4 |
| | Detection probe | B19_1450F-FAM | 156 | ATGGCTATTGCTAAAACTGTTCCAGTGTA | 63.2 |
| | Detection probe | B19_1492F-FAM | 157 | TGGAATAATGAAAACTTTCCATTTAATGATGTAG | 61.0 |
| | Detection probe | B19_1448F-FAM | 158 | CAATGGCCATTGTCTAAAAGTGTTCCA | 63.0 |

FIG. 10

METHODS FOR DETECTION OF PARVOVIRUS B19

CROSS REFERENCE TO RELATED APPLICATIONS

The present application is a continuation of U.S. patent application Ser. No. 12/523,309, filed on Jul. 17, 2009, which is a National Phase Entry under §371 of International Application No. PCT/US08/51083 filed Jan. 15, 2008, which claims the benefit of priority to U.S. Application No. 60/885,074 filed Jan. 16, 2007, and U.S. Application No. 60/942,762 filed Jun. 8, 2007, each of which is herein incorporated by reference in its entirety.

FIELD OF THE INVENTION

The present invention relates to human *erythrovirus* and includes methods and compositions useful for detection of a novel variant.

BACKGROUND OF THE INVENTION

Members of the Parvoviridae family of viruses are common animal and insect pathogens, which are further classified into the subfamily Parvoviridae based at least on the ability to infect vertebrate cells. Parvovirinae belonging to the genus *Erythrovirus* are known to infect humans and include, for example, the prototypical parvovirus B19 referred to as Au (genotype 1) as well as variants such as A6 (genotype 2), and V9 and D91.1 (genotype 3). They are non-enveloped viruses that comprise a single-stranded, linear DNA genome. For example, the prototypical human *erythrovirus* known as parvovirus B19-Au (See e.g., GenBank Accession Number: M13178) has a linear DNA genome of approximately 5.6 kilobases in length.

Discovered in 1975, parvovirus B19 was subsequently linked to an aplastic crisis in a patient with sickle-cell disease. The virus has since been shown to cause or be associated with a variety of conditions and diseases including erythma infectiosum (EI) (fifth disease of childhood), spontaneous abortion, and certain forms of acute arthritis.

*Erythrovirus* are ubiquitous and contagious. In the case of parvovirus B19, an estimated 60% of adults are seropositive. Children are particularly susceptible at the age when they begin to play together regularly and attend school, the peak season for infection being in the spring and early summer.

In addition to transmission through airborne infections and close contact, human *erythrovirus* can also be transmitted vertically from a pregnant woman to her fetus. For example, among pregnant women with active cases, about 30% of the fetuses will become infected with parvovirus B19. And, it is now well documented that parvovirus B19 can cause spontaneous abortion when infection occurs within the first six weeks after conception. Infection at this early stage causes massive abnormalities that are inconsistent with life.

Transmission of human *erythrovirus* also can occur via blood or plasma products of various kinds. For example, cases of symptomatic illness have been reported to be due to blood products prepared from parvovirus B19-containing plasma pools. Parvovirus B19 DNA has been detected in single donations, in plasma pools, and in plasma derivatives (e.g., clotting factors, albumin, antithrombin III, and immunoglobulins) produced by different processes. Parvovirus B19 transmission has also been found in patients treated with clotting factors, as shown by a higher seroprevalence in treated hemophiliacs, by the presence of parvovirus B19 DNA, and by active seroconversion. Unfortunately, the risk of human *erythrovirus* transmission by blood/plasma products is enhanced by the virus's resistance to effective inactivation methods such as heat and solvent-detergent treatments.

Therefore, health risks from exposure to human *erythrovirus* continue to exist, and identification and characterization of variants of the *Erythrovirus* genus will constitute an important step towards proper diagnosis and management of infection. Immunodiagnostic methods have been used to test blood, serum, or plasma that is potentially contaminated with human *erythrovirus*. But such immunodiagnostic methods have limitations including, for example, inability to effectively detect recent or current infections and/or inability to distinguish between the different *erythrovirus* genotypes. There is still a need, therefore, for identifying and characterizing human *erythrovirus* variants and developing sensitive and effective assays for detecting them and/or distinguishing from among them.

SUMMARY OF THE INVENTION

There is now provided an isolated nucleic acid molecule comprising a nucleotide sequence as set forth in SEQ ID NO: 1, SEQ ID NO:128, SEQ ID NO:129, or a complement thereof.

In one aspect, the present invention provides nucleic acid molecules that are individually useful for detection of Parvoviridae represented by the nucleic acid sequence of SEQ ID NO:1 (i.e., partial genomic sequence of the novel variant named D11 disclosed herein), as well as those of known parvovirus B19 Au genotype 1, A6 genotype 2, V9 genotype 3, and D91.1 genotype 3. Accordingly, the invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of:

```
                                         (SEQ ID NO: 2)
5'-GATAACTGGTGGTGCTCT-3';

(SEQ ID NO: 3)
5'-ACTTCTGACTGGGA-3';

(SEQ ID NO: 4)
5'-GAATGTAACAAATTTGA-3';

(SEQ ID NO: 5)
5'-TTATTTAATAATGT-3';

(SEQ ID NO: 6)
5'-CTTGTAACTGAAA-3';

(SEQ ID NO: 7)
5'-TTTAGAGATGGAGA-3';

(SEQ ID NO: 8)
5'-TTAATGAAAAAAAT-3';

(SEQ ID NO: 9)
5'-CCTTTAAATGTTGT-3';

(SEQ ID NO: 10)
5'-CAGACTTTGAGCAGG-3';

(SEQ ID NO: 11)
5'-TGGAATAATGAAAA-3';

(SEQ ID NO: 12)
5'-TTTCCATTTAATGATGTAGC-3';
```

-continued (SEQ ID NO: 13)
5'-TTGGTGGTCTGGGATGA-3';

(SEQ ID NO: 14)
5'-GAAGCTGCAAAAGCCATTTTAGG-3';

(SEQ ID NO: 15)
5'-ACCAGGGTAGATCA-3';

(SEQ ID NO: 16)
5'-ATAACCAGCAATGGTGACATTAC-3';

(SEQ ID NO: 17)
5'-CATGCTAAAGCCTTAAA-3';

(SEQ ID NO: 18)
5'-AGCCCTGACATGGG-3';

(SEQ ID NO: 19)
5'-TGGTGTAATGCACAAAGCTGG-3';

(SEQ ID NO: 20)
5'-CCACTATGAAAACTGGGCAATAAACTACAC-3';

(SEQ ID NO: 21)
5'-TTTGATTTCCCTGGAAT-3';

(SEQ ID NO: 22)
5'-AATGCAGATGCCCTCCACCCAGA-3';

(SEQ ID NO: 23)
5'-CTCCAAACCACCCC-3';

(SEQ ID NO: 24)
5'-TCAGCAGCAGTGGTGGTGAAAGCTCTGAAGAACTC-3';

(SEQ ID NO: 25)
5'-CCAGGCGCCTGGAACA-3';

(SEQ ID NO: 26)
5'-TGAAACCCCGCGCTCTAGTACGCC-3';

(SEQ ID NO: 27)
5'-TCCCCGGGACCAGTTCAGGAGAATCATTTGTCGGAAGC-3';

(SEQ ID NO: 28)
5'-CAGTTTCGTGAACTGTTAGT-3';

(SEQ ID NO: 29)
5'-GCTTGGTATAATGGATGGAA-3';

(SEQ ID NO: 30)
5'-AAATGTGCTTACCT-3';

(SEQ ID NO: 31)
5'-TTTGTAGATTATGAGTAAA-3';

(SEQ ID NO: 32)
5'-ATTTCTTTAGATAATCC-3';

(SEQ ID NO: 33)
5'-TATATAGTCATCATTTTCA-3';

(SEQ ID NO: 34)
5'-CATGGACAGTTATCTGACCACCCCATGCCTTATCATCCAGTA-3';

(SEQ ID NO: 35)
5'-CAGAACCTAGAGGAGAAAATGCAGTATTATCTA-3';

(SEQ ID NO: 36)
5'-TGAAGACTTACACAAGCCTGGGCAAGTTAGC-3';

(SEQ ID NO: 37)
5'-TACCCGGTACTAACTATGTTGGGCCTGGCAATGAG-3';

(SEQ ID NO: 38)
5'-TACAAGCTGGGCC-3';

(SEQ ID NO: 39)
5'-GACAGTGCTGCAAGGATTCATGACTTTAGGTATAGCCAA-3';

-continued (SEQ ID NO: 40)
5'-TTAAAAAATATAAAAAATGAAAC-3';

(SEQ ID NO: 41)
5'-TACTTTACTTTAAAAGGTGCAGCTGCCCCTGTGGCCCATTTTCAAGG
AAGTTT-3';

(SEQ ID NO: 42)
5'-TACAACGCCTCAGAAAAATACCC-3';

(SEQ ID NO: 43)
5'-AGCATGACTTCAGTTAA-3';

(SEQ ID NO: 44)
5'-TCTGCAGAAGCCAGCACTGGTGCAGG-3';

(SEQ ID NO: 45)
5'-AAAAGCATGTGGAGTGA-3';

(SEQ ID NO: 46)
5'-AGTAGCTGCCACAATGC-3';

(SEQ ID NO: 47)
5'-TTAGATTTTAATGCTTT-3';

(SEQ ID NO: 48)
5'-GATGCTTTAACTGT-3';

(SEQ ID NO: 49)
5'-TATGCTTACTTAACAGTAGG-3';

(SEQ ID NO: 50)
5'-AGTGAAGAATCAGC-3';

(SEQ ID NO: 51)
5'-TTTTATGAAATGTACAA-3';

(SEQ ID NO: 52)
5'-GCTGAAGACAAAGAGTATCA-3';

(SEQ ID NO: 53)
5'-AATGAAAAGAACA-3';

(SEQ ID NO: 54)
5'-TGGAACAGAAGAGC-3';

(SEQ ID NO: 55)
5'-CTTCACTATGAAAG-3';

(SEQ ID NO: 56)
5'-CCTCAAATATTTTTAAAAATA-3';

(SEQ ID NO: 57)
5'-CCTCAAATATTTTTAAAAATA-3';

(SEQ ID NO: 58)
5'-CATTTACCATATGTACT-3';

(SEQ ID NO: 59)
5'-TATGACCCCACAGCTACAGATGCAAA-3';
and (SEQ ID NO: 60)
5'-GGATATGAAAAGCCTGAAGAATTGTGGAC-3'.

In another aspect, the present invention provides nucleic acid molecules that are individually useful for specific detection of the Parvoviridae represented by the nucleic acid sequence of SEQ ID NO:1. Accordingly, the invention includes an isolated nucleic acid molecule comprising at least 12, at least 15, or at least 20 contiguous nucleotides of a nucleotide sequence or a complement thereof. The nucleotide sequence is selected from the group consisting of (SEQ ID NO: 61)
5'-CACTTCTGACTGGGAACCATTAACTCATTCTAACAGACT-3',

```
                                              (SEQ ID NO: 62)
5'-ATGTAAAGCTTAAATTTTTACCAGGAATGACTACAAAAG-3', (SEQ ID NO: 63)
5'-AATATTTTAGAGATGGAGAACAATTTATAGAAAATTATT-3', (SEQ ID NO: 64)
5'-ATTTTAGAGATGGAGAACAATTTATAGAAAATTATTTAA-3', (SEQ ID NO: 65)
5'-TAACCAATATTGATGGGTACATAGATACCTGCATTTCTG-3', (SEQ ID NO: 66)
5'-ATGGGTACATAGATACCTGCATTTCTGCTTCTTTTAGAC-3', (SEQ ID NO: 67)
5'-TTAGACGGGGAGCCTTTCAGGCTAAAAACCCCGCATTA-3', (SEQ ID NO: 68)
5'-GAACCAGGGGAATCTAGCGCTACAGGGGGAGATGTTGTG-3', (SEQ ID NO: 69)
5'-TGCCATTTGCTGGGAAGGGGACTAAAGCTGGAATAAAAT-3', (SEQ ID NO: 70)
5'-GGACTAAAGCTGGAATAAAATTTCAAACTATGGTAAATT-3', (SEQ ID NO: 71)
5'-TAAATTGGTTGTGTGAAAATAGGGTTTTTACAGAGGATA-3', (SEQ ID NO: 72)
5'-ATTGGTTGTGTGAAAATAGGGTTTTTACAGAGGATAAGT-3', (SEQ ID NO: 73)
5'-TTAACCAGTACACTTTACTTAGCAGTAGTCACAGTGGGA-3', (SEQ ID NO: 74)
5'-TAAAACTAGCTATTTATAAGGCTACCAATTTAGTGCCTA-3', (SEQ ID NO: 75)
5'-TAGCTATTTATAAGGCTACCAATTTAGTGCCTACAAGTA-3', (SEQ ID NO: 76)
5'-CTACCAATTTAGTGCCTACAAGTACATTTTTGTTACACA-3', (SEQ ID NO: 77)
5'-CAAGTACATTTTTGTTACACACAGACTTTGAGCAGGCTA-3', (SEQ ID NO: 78)
5'-CACACAGACTTTGAGCAGGCTAACTGTATTAAAGAAAAT-3', (SEQ ID NO: 79)
5'-GTGTCAAAATTATGACCCCTTGTTGGTGGGACAGCATGT-3', (SEQ ID NO: 80)
5'-GGATTGATAAAAAATGTGGCAAAAAAAATACACTGTGGT-3', (SEQ ID NO: 81)
5'-ATACACTGTGGTTTTATGGCCCACCAAGTACAGGAAAAA-3', (SEQ ID NO: 82)
5'-GTACAGGAAAAACAAATTTAGCAATGGCTATTGCTAAAA-3', (SEQ ID NO: 83)
5'-GCTTGGTGGTCTGGGATGAGGGTATTATTAAGTCTACTA-3', (SEQ ID NO: 84)
5'-GCTTACTTACAGAGGCTGACGTGCAGCAATGGCTTACAT-3', (SEQ ID NO: 85)
5'-CCCCGCGCTCTAGTACGCCAGTCCCCGGGACCAGTTCAG-3', (SEQ ID NO: 86)
5'-AGAATCATTTGTCGGAAGCTCAATTTCCTCCGAAGCTGT-3', (SEQ ID NO: 87)
5'-ATCATTTGTCGGAAGCTCAATTTCCTCCGAAGCTGTAGC-3', (SEQ ID NO: 88)
5'-AGCTCAATTTCCTCCGAAGCTGTAGCTGCATCGTGGGAA-3', (SEQ ID NO: 89)
5'-TGACTATGTATGGGATGGTATAAGGGGTTTACCTGTTTG-3', (SEQ ID NO: 90)
5'-TTAATAACAGTGGGGGAGGCTTGGGATTTTGTCCCCATT-3', (SEQ ID NO: 91)
5'-CAGTGGGGGAGGCTTGGGATTTTGTCCCCATTGCATTAA-3', (SEQ ID NO: 92)
5'-GCAAAAAATGTGCTTACCTATCTGGCTTGCAAAGTTTTG-3', (SEQ ID NO: 93)
5'-AATGTGCTTACCTATCTGGCTTGCAAAGTTTTGTAGATT-3', (SEQ ID NO: 94)
5'-TTTGTAGATTATGAGTAAAGAAATTGGTAAATGGTGGGA-3', (SEQ ID NO: 95)
5'-TTATGAGTAAAGAAATTGGTAAATGGTGGGAAAGTGATG-3', (SEQ ID NO: 96)
5'-CTTCTTTGTTTGACTTAGTGGCTCGTATTAAAAGTAACC-3', (SEQ ID NO: 97)
5'-ATGAAACTGGGTTTCAAGCTCAAGTAGTAAAAGACTACT-3', (SEQ ID NO: 98)
5'-TCCTGATGCTTTAACTGTTGCCATATCAGAAATTGCCAT-3', (SEQ ID NO: 99)
5'-TTGCCATATCAGAAATTGCCATTAAAGATGTTACAGACA-3', (SEQ ID NO: 100)
5'-TGCCATATCAGAAATTGCCATTAAAGATGTTACAGACAA-3', (SEQ ID NO: 101)
5'-AATACAAGTACCCATATGTATTAGGTCAAGGACAAGATA-3', (SEQ ID NO: 102)
5'-AAGATACCTTAGCCCCAGAGCTTCCAATTTGGGTGTACT-3', (SEQ ID NO: 103)
5'-CAGTAGGAGATGTAAACACGCAGGGAATTTCTGGGGACA-3', (SEQ ID NO: 104)
5'-AGAATCAGCGTTTTATGTCCTGGAACACAGCTCTTTTGA-3', (SEQ ID NO: 105)
5'-CTACTATGTCTTATAAGTTCCCTCCAGTGCCCCCAGAGA-3', (SEQ ID NO: 106)
5'-TCCCTCCAGTGCCCCCAGAGAATTTAGAAGGCTGTAGTC-3', (SEQ ID NO: 107)
5'-CCCGTTTAGGAGTCCCTGATACATTAGGAGGGGACCCCA-3', (SEQ ID NO: 108)
5'-AACACATGAAGACCACGCAGTTCAGCCACAAAATTTTAT-3', (SEQ ID NO: 109)
5'-ACGCAGTTCAGCCACAAAATTTTATGCCAGGGCCACTGG-3', (SEQ ID NO: 110)
5'-GGCCACTGGTAAACTCAGTTTCCACAAAGGAGGGAGACA-3', (SEQ ID NO: 111)
5'-AGGAGGGAGACAGTTCTAACACAGGAGCGGGAAAAGCCC-3', (SEQ ID NO: 112)
5'-GTCAAAGTACTAGAATATCATTACGCCCTGGTCCAGTGT-3', (SEQ ID NO: 113)
5'-GCCCTGGTCCAGTGTCTCAACCATATCACCACTGGGACA-3', (SEQ ID NO: 114)
5'-GTCCAGTGTCTCAACCATATCACCACTGGGACACAGATA-3', (SEQ ID NO: 115)
5'-CAGATAAATATGTAACAGGGATAAATGCCATTTCTCATG-3',
```

```
                                                (SEQ ID NO: 116)
5'-CTGAAGACAAAGAGTATCAACAGGGCGTGGGTAGGTTTC-3', (SEQ ID NO: 117)
5'-AAGACAAAGAGTATCAACAGGGCGTGGGTAGGTTTCCCA-3', (SEQ ID NO: 118)
5'-AGGGCGTGGGTAGGTTTCCCAATGAAAAAGAACAACTAA-3', (SEQ ID NO: 119)
5'-AACAGTTACAGGGTTTAAATATACACACATATTTTCCCA-3', (SEQ ID NO: 120)
5'-GTTTAAATATACACACATATTTTCCCAATAAAGGTACCC-3', (SEQ ID NO: 121)
5'-TACCAAATTTAGATGACAGCTTTAAAACTCAGTTTGCAG-3', (SEQ ID NO: 122)
5'-AGCTTTAGGAGGTTGGGGACTACATCAGCCACCCCCTCA-3', (SEQ ID NO: 123)
5'-GGCCAATTGGGGGTATTAAGTCAATGGGAATAACAACAT-3', (SEQ ID NO: 124)
5'-TTAAGTCAATGGGAATAACAACATTAGTTCAATATGCTG-3', (SEQ ID NO: 125)
5'-TAGTTCAATATGCTGTGGGTATTATGACAGTAACATGA-3', (SEQ ID NO: 126)
5'-TAACTATGACATTTAAATTAGGGCCTCGCAAAGCTACAG-3',
and (SEQ ID NO: 127)
5'-ACCCTCCTCACGCAGCAGGCCATTTACCATATGTACTAT-3'.
```

In other aspects, the present invention provides an isolated nucleic acid molecule consisting of a nucleotide sequence or a complement thereof, wherein the nucleotide sequence is selected from the group consisting of:

```
                                                (SEQ ID NO: 136)
5'-TGAAACCCCGCGCTCTA-3';

(SEQ ID NO: 137)
5'-AACTAACAGTTCACGAAACTG-3';

(SEQ ID NO: 138)
5'-TCCCCGGGACCAGTTCAGGAGAA-3';

(SEQ ID NO: 139)
5'-TCAGCAGCAGTGGTGGT-3';

(SEQ ID NO: 140)
5'-TAGAGCGCGGGGTTTCA-3';

(SEQ ID NO: 141)
5'-TGAAAGCTCTGAAGAACTCAGTGAAAGCAGCTTT-3';

(SEQ ID NO: 142)
5'-AATGCAGATGCCCTCCAC-3';

(SEQ ID NO: 143)
5'-TCAGCAGCAGTGGTGGTGAAAGCTCTGAA-3';

(SEQ ID NO: 144)
5'-TGTTCCAGGCGCCTG-3';

(SEQ ID NO: 145)
5'-CACAGCTACAGATGCAAA-3';

(SEQ ID NO: 146)
5'-GGTGCACACGGCTTTT-3';

(SEQ ID NO: 147)
5'-TGTCCACAATTCTTCAGGCTTTTCATATCC-3';

(SEQ ID NO: 148)
5'-TGGATATGAAAAGCCTGAAGTATTGTGGAC-3';

(SEQ ID NO: 149)
5'-GGTCATTTACCATATGTACT-3';

(SEQ ID NO: 150)
5'-AGCTACAGATGCAAANCAACACCACAGACA-3';

(SEQ ID NO: 151)
5'-GAAAACTTTCCATTTAATGATGT-3';

(SEQ ID NO: 152)
5'-ATTTTTTGATCTACCCTGGT-3';

(SEQ ID NO: 153)
5'-TTGGTGGTCTGGGATGAAGG-3';

(SEQ ID NO: 154)
5'-GTTTTATGGGCCGCCAAGTA-3';

(SEQ ID NO: 155)
5'-TTCATCCCAGACCACCAAGG-3';

(SEQ ID NO: 156)
5'-ATGGCTATTGCTAAAACTGTTCCAGTGTA-3';

(SEQ ID NO: 157)
5'-TGGAATAATGAAAACTTTCCATTTAATGATGTAG-3';
and (SEQ ID NO: 158)
5'-CAATGGCCATTGCTAAAAGTGTTCCA-3'.
```

In some aspects, the present invention provides an isolated nucleic acid molecule that anneals under a stringent condition to a polynucleotide comprising a nucleotide sequence as set forth in SEQ ID NO: 1, SEQ ID NO:128, SEQ ID NO:129, or a complement thereof, but does not anneal under the stringent condition to a non-parvovirus DNA or RNA molecule that may be present in a test sample (i.e., binds specifically to parvovirus B19 nucleic acid).

In one aspect, the present invention provides an isolated nucleic acid molecule that anneals under a stringent condition to a nucleotide sequence as set forth in SEQ ID NO: 1, SEQ ID NO:128, SEQ ID NO:129, or a complement thereof, wherein the isolated nucleic acid molecule also anneals under the stringent condition to a DNA or a RNA of parvovirus B19 Au, A6, V9, or D91.1.

In another aspect, the present invention provides an isolated nucleic acid molecule that anneals under a stringent condition to a nucleotide sequence or a complement thereof, wherein the nucleotide sequence is as set forth in SEQ ID NO: 1, SEQ ID NO:128, SEQ ID NO:129, SEQ ID NO:130, SEQ ID NO:131, SEQ ID NO:132, and SEQ ID NO:133.

In other aspects, the present invention provides an isolated nucleic acid molecule that anneals under a stringent condition to a nucleotide sequence as set forth in SEQ ID NO: 1, SEQ ID NO:128, SEQ ID NO:129, or a complement thereof, wherein the isolated nucleic acid molecule does not anneal under the stringent condition to a DNA or a RNA of parvovirus B19 Au, A6, V9, or D91.1.

In various other aspects, the present invention provides an isolated nucleic acid molecule comprising an open reading frame, a partial open reading frame, or a complement thereof, wherein the open reading frame is comprised in SEQ ID NO: 1, SEQ ID NO:128, SEQ ID NO:129, or a complement thereof.

In other aspects, the present invention provides an isolated human *erythrovirus* comprising a genome comprising a nucleotide sequence as set forth in SEQ ID NO: 1, SEQ ID NO:128, or SEQ ID NO:129.

In one aspect, the present invention provides a kit comprising at least one primer and at least one probe, wherein the at least one primer comprises a primer nucleic acid sequence as set forth in (SEQ ID NO: 136), (SEQ ID NO: 137), (SEQ ID NO: 139), (SEQ ID NO: 140), (SEQ ID NO: 142), (SEQ ID NO: 144), (SEQ ID NO: 145), (SEQ ID NO: 146), (SEQ ID NO: 149), (SEQ ID NO: 151), (SEQ ID NO: 152), (SEQ ID NO: 154), or (SEQ ID NO: 155), wherein the at least one probe comprises a probe nucleic acid sequence as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In another aspect, the kit comprises a forward primer, a reverse primer, and a probe, wherein the forward primer comprises a forward primer nucleic acid sequence as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO: 154), wherein the reverse primer comprises a reverse primer nucleic acid sequence as set forth in (SEQ ID NO: 137), (SEQ ID NO: 140), (SEQ ID NO: 144), (SEQ ID NO: 146), (SEQ ID NO: 152), or (SEQ ID NO: 155), wherein the probe comprises a probe nucleic acid sequence as set forth in (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), (SEQ ID NO: 158), or complements thereof.

In some aspects, the present invention provides a method for detecting a parvovirus B19 in a sample. The method comprises:

a) performing PCR with at least a portion of the sample using a forward primer having a forward primer nucleic acid sequence and a reverse primer having a reverse primer nucleic acid sequence, wherein the forward primer nucleic acid sequence is as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO: 154), wherein the reverse primer nucleic acid sequence is as set forth in (SEQ ID NO: 137), (SEQ ID NO: 140), (SEQ ID NO: 144), (SEQ ID NO: 146), (SEQ ID NO: 152), or (SEQ ID NO: 155); and b) determining the presence or absence of an amplicon, wherein the presence of the amplicon is indicative of the presence of the parvovirus B19 in the sample, wherein determining comprises annealing an oligonucleotide to the amplicon.

In further aspects, the present invention provides a method for determining parvovirus B19 in a sample. The method comprises a) amplifying parvovirus B19 nucleic acid in the sample using at least one nucleic acid molecule comprising i) a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), and (SEQ ID NO: 60); or ii) at least 12, at least 15, or at least 20 contiguous nucleotides of a nucleotide sequence or a complement thereof, wherein the nucleotide sequence is selected from the group consisting of: (SEQ ID NO: 61), (SEQ ID NO: 62), (SEQ ID NO: 63), (SEQ ID NO: 64), (SEQ ID NO: 65), (SEQ ID NO: 66), (SEQ ID NO: 67), (SEQ ID NO: 68), (SEQ ID NO: 69), (SEQ ID NO: 70), (SEQ ID NO: 71), (SEQ ID NO: 72), (SEQ ID NO: 73), (SEQ ID NO: 74), (SEQ ID NO: 75), (SEQ ID NO: 76), (SEQ ID NO: 77), (SEQ ID NO: 78), (SEQ ID NO: 79), (SEQ ID NO: 80), (SEQ ID NO: 81), (SEQ ID NO: 82), (SEQ ID NO: 83), (SEQ ID NO: 84), (SEQ ID NO: 85), (SEQ ID NO: 86), (SEQ ID NO: 87), (SEQ ID NO: 88), (SEQ ID NO: 89), (SEQ ID NO: 90), (SEQ ID NO: 91), (SEQ ID NO: 92), (SEQ ID NO: 93), (SEQ ID NO: 94), (SEQ ID NO: 95), (SEQ ID NO: 96), (SEQ ID NO: 97), (SEQ ID NO: 98), (SEQ ID NO: 99), (SEQ ID NO: 100), (SEQ ID NO: 101), (SEQ ID NO: 102), (SEQ ID NO: 103), (SEQ ID NO: 104), (SEQ ID NO: 105), (SEQ ID NO: 106), (SEQ ID NO: 107), (SEQ ID NO: 108), (SEQ ID NO: 109), (SEQ ID NO: 110), (SEQ ID NO: 111), (SEQ ID NO: 112), (SEQ ID NO: 113), (SEQ ID NO: 114), (SEQ ID NO: 115), (SEQ ID NO: 116), (SEQ ID NO: 117), (SEQ ID NO: 118), (SEQ ID NO: 119), (SEQ ID NO: 120), (SEQ ID NO: 121), (SEQ ID NO: 122), (SEQ ID NO: 123), (SEQ ID NO: 124), (SEQ ID NO: 125), (SEQ ID NO: 126), and (SEQ ID NO: 127); and b) detecting an amplicon generated in step (a), wherein detection of the amplicon indicates presence of the variant in the sample, wherein detecting optionally comprises the step of annealing at least one nucleic acid molecule of step (a)(ii) to the amplicon.

In some aspects, the present invention provides for a method for determining parvovirus B19 in a sample. The method comprises a) amplifying parvovirus B19 nucleic acid in the sample using at least one nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO:

48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), and (SEQ ID NO: 60); and b) detecting an amplicon generated in step (a), wherein detection of the amplicon indicates presence of the parvovirus B19 in the sample, wherein detecting optionally comprises the step of annealing at least one nucleic acid molecule to the amplicon.

Advantages and benefits of the present invention will be apparent to one skilled in the art from reading this specification.

BRIEF DESCRIPTION OF THE FIGURES

FIG. 1 shows a partial genomic DNA sequence corresponding to a novel parvovirus B19 variant disclosed herein (i.e., SEQ ID NO: 1 for the D11 variant). Open reading frames (ORF) for VP1 and VP2 proteins begin at nucleotide position 2105 and 2786, respectively, whereas the partial ORF for NS 1 protein is shown from nucleotide position 1 through 2109, where nucleotide position 2107-2109, namely GAG, encodes glutamic acid.

FIG. 2A-2B shows a partial genomic DNA sequence corresponding to a novel parvovirus B19 variant disclosed and referred to herein as E3 (i.e., SEQ ID NO: 128). The open reading frame (ORF) for VP1 protein begins at nucleotide position 2141, whereas nucleotide position 1 through 2145 comprises the partial ORF for NS 1 protein.

FIG. 3A-3B shows a partial genomic DNA sequence corresponding to a novel parvovirus B19 variant disclosed and referred to herein as P1 (i.e., SEQ ID NO: 129). The open reading frame (ORF) for VP1 protein begins at nucleotide position 2263, whereas nucleotide position 1 through 2267 comprises the partial ORF for NS 1 protein.

Figure 4B:
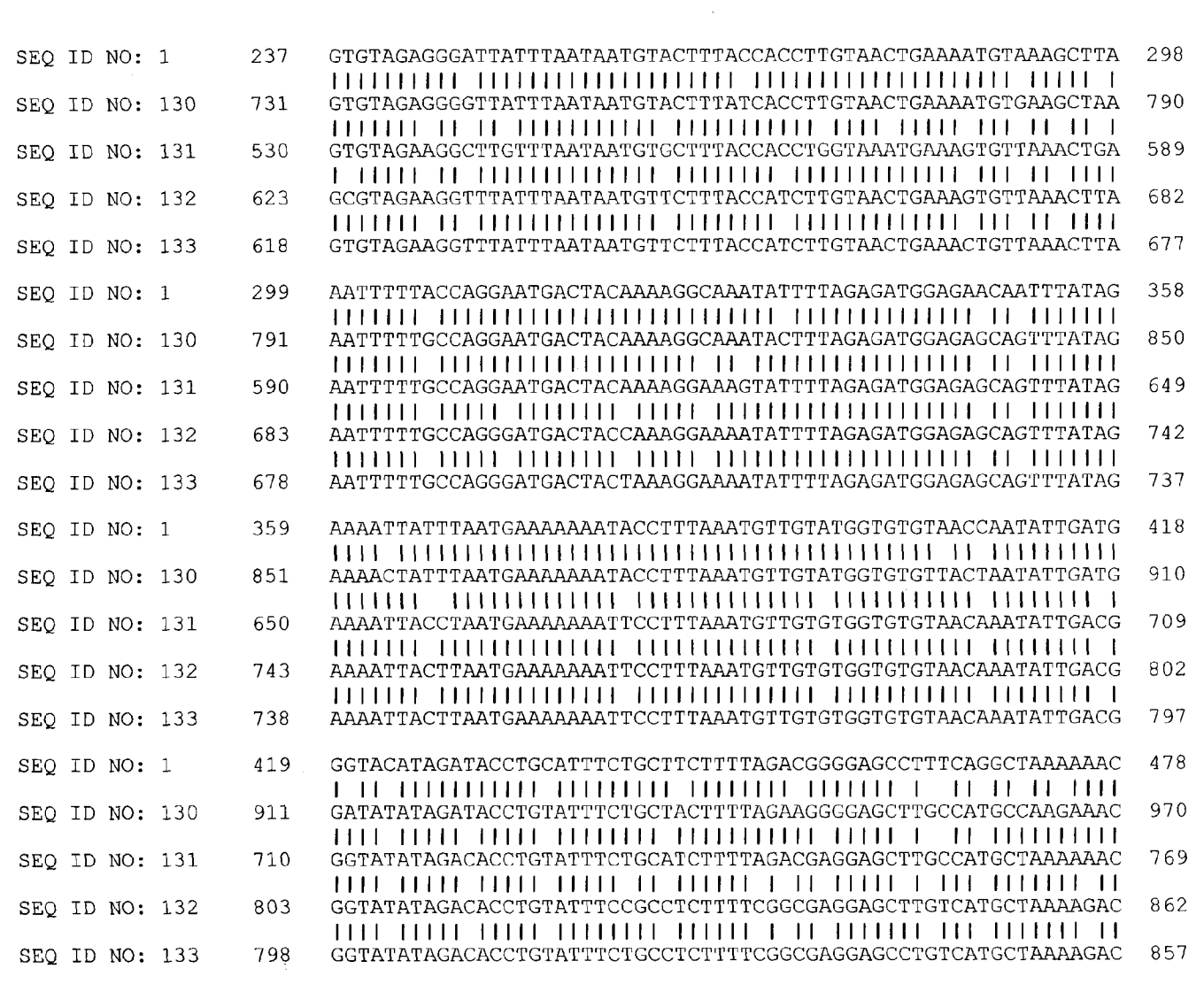
Figure 4C:
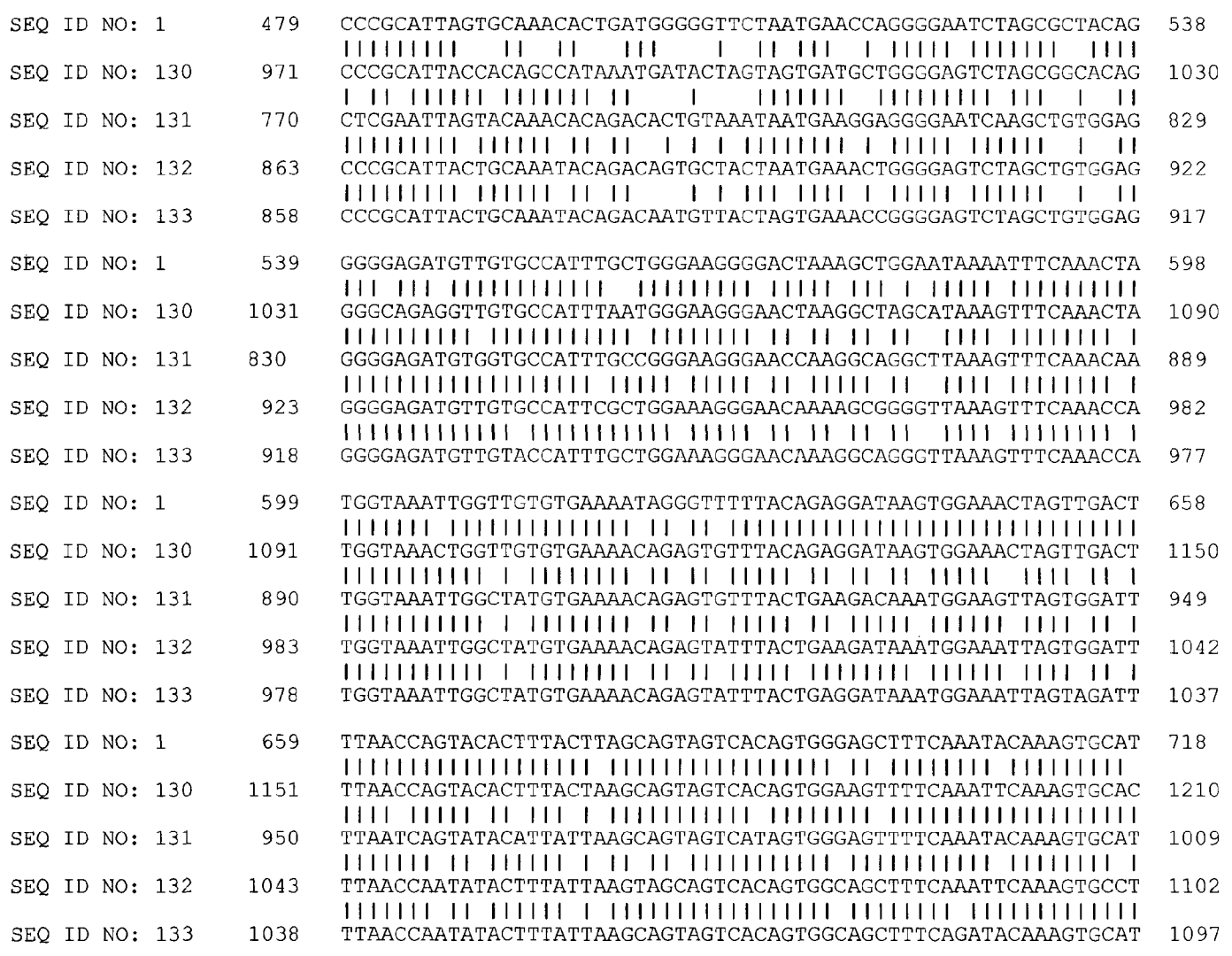
Figure 4E:
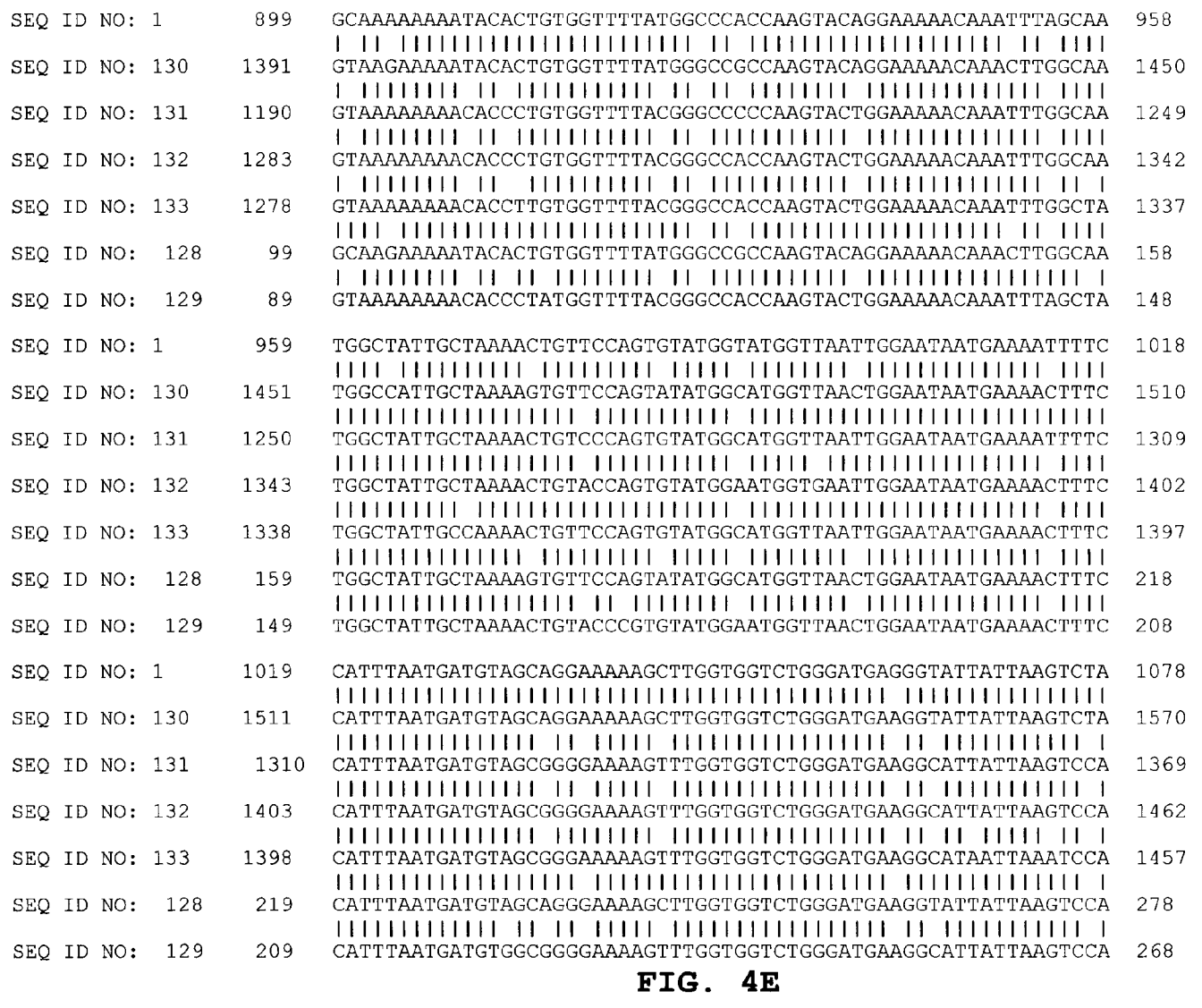
Figure 4F:
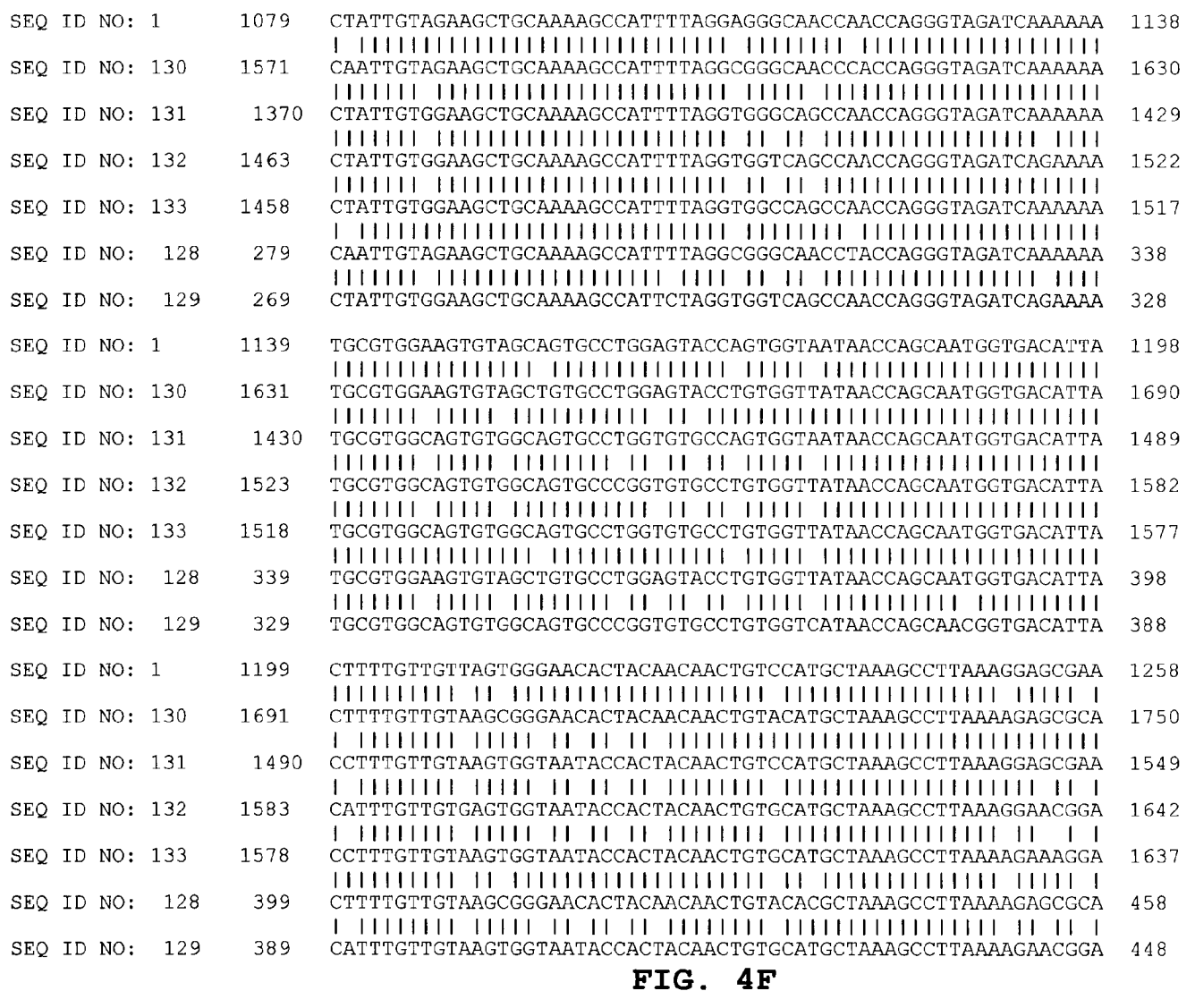
Figure 4G:
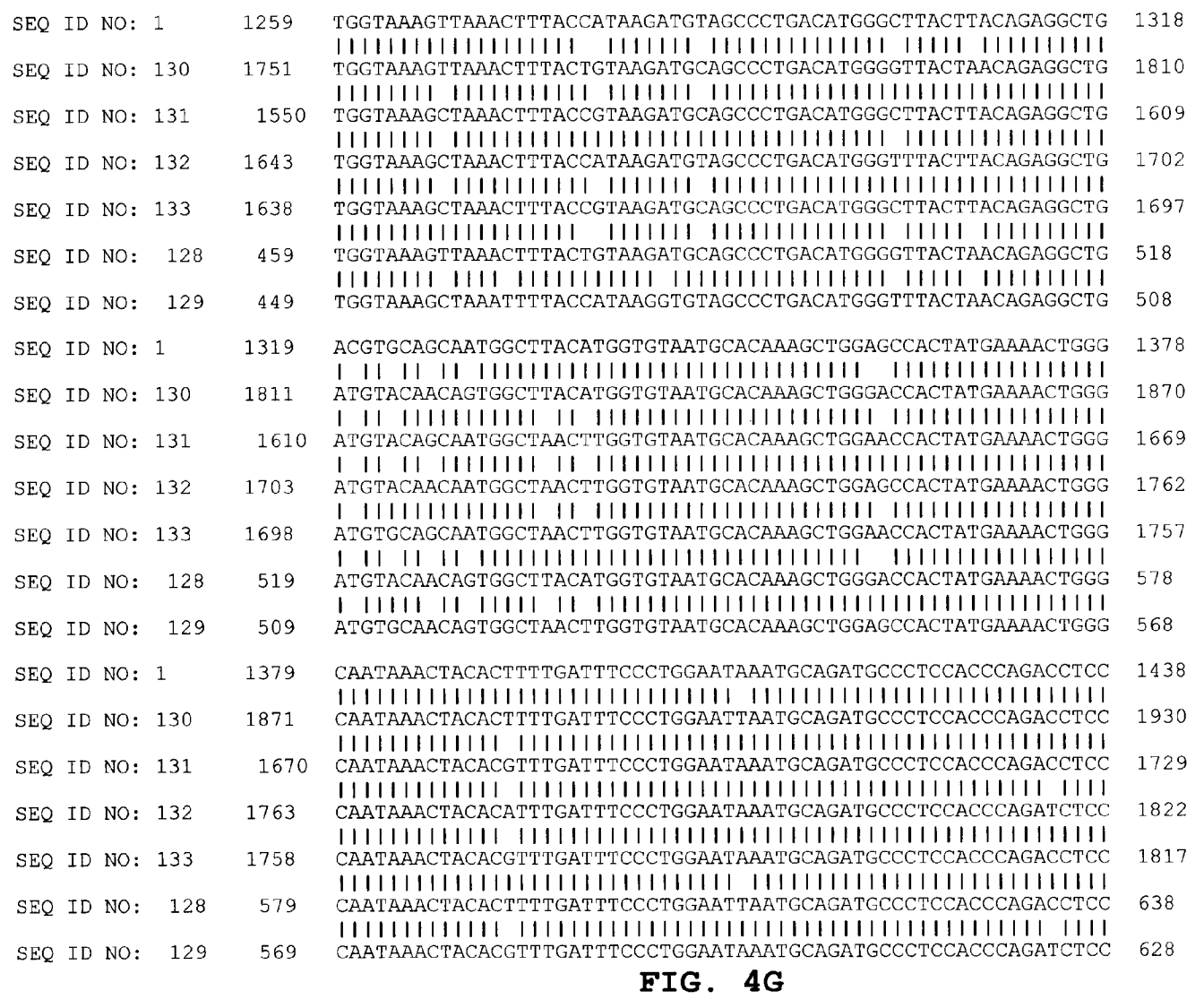
Figure 4H:
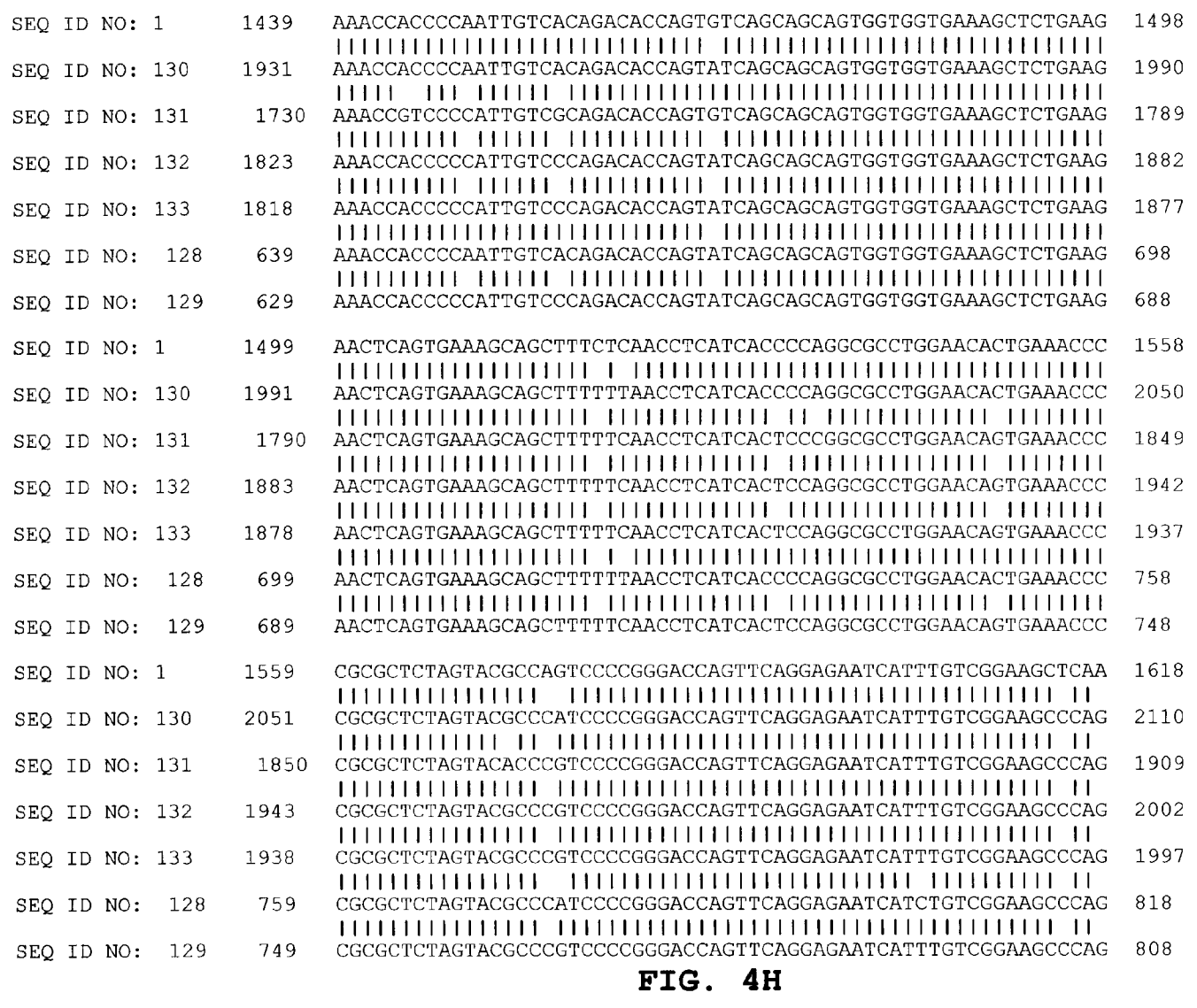
Figure 4L:
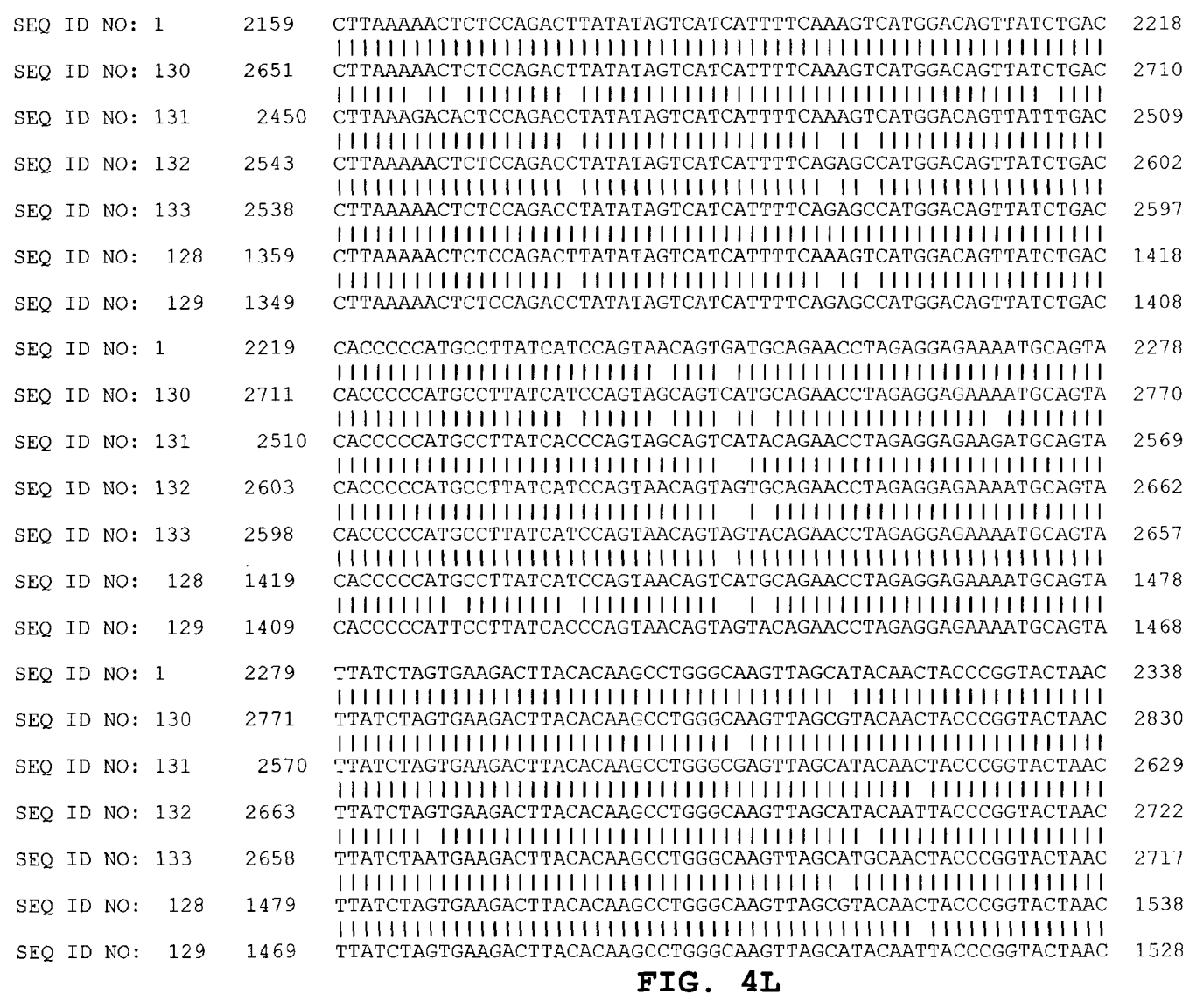
Figure 4R:
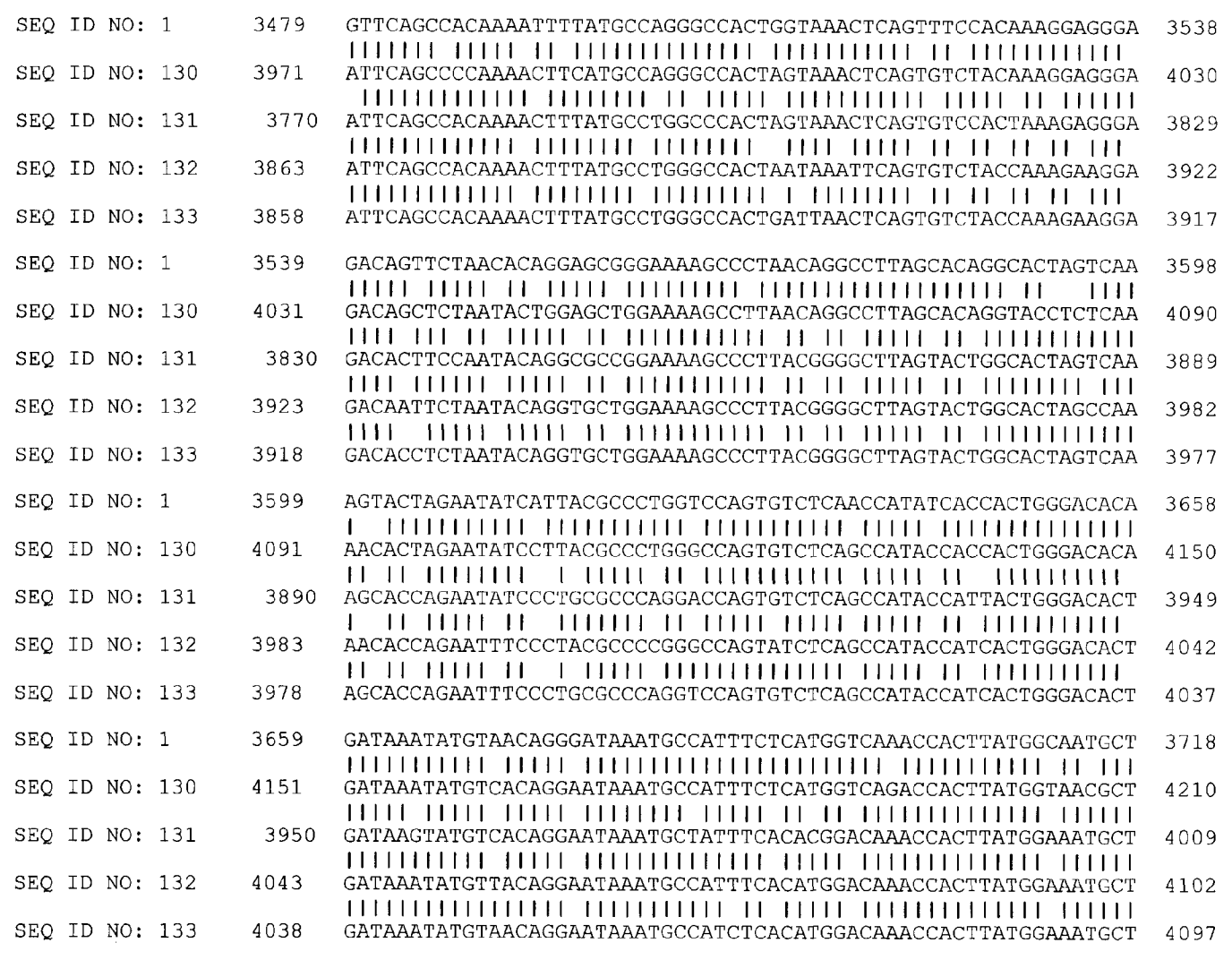

FIG. 4A-U shows an alignment of partial DNA sequences of the novel human parvovirus B19 variants of the invention (i.e., SEQ ID NO: 1 for the D11 variant, SEQ ID NO: 128 for the E3 variant, SEQ ID NO: 129 for the P1 variant); Au human parvovirus B19 DNA, genotype 1 (i.e., SEQ ID NO: 130 for Accession Number: M13178); A6 human parvovirus B19 DNA, genotype 2 (i.e., SEQ ID NO: 131 for Accession Number: AY064476); V9 human parvovirus B19 DNA, genotype 3 (i.e., SEQ ID NO: 132 for Accession Number: NC_004295); and D91.1 human parvovirus B19 DNA, genotype 3 (i.e., SEQ ID NO: 133 for Accession Number: AY083234). In the alignment, the nucleotide shown at position 1 for SEQ ID NO:1, SEQ ID NO:128, and SEQ ID NO: 129 corresponds to the nucleotide at position 154 in FIG. 1, 991 in FIG. 2, and 1122 in FIG. 3, respectively.

FIG. 5A-E shows alignment of 97% consensus sequence to parvovirus B19 Genotype 1 prototype strain Au (i.e., PVBAUA, SEQ ID NO:130).

FIG. 6 shows alignment of the parvovirus B19 Genotype 1 prototype strain Au (i.e., PVBAUA, SEQ ID NO:130) with the 97% consensus sequence showing the highly conserved region from nucleotides 1351 to 2426.

FIG. 7 shows alignment of the parvovirus B19 Genotype 1 prototype strain Au (i.e., PVBAUA SEQ ID NO:130) with the 97% consensus sequence showing the highly conserved region from nucleotides 3704 to 4804.

FIG. 9 shows alignment of the primers and probes (SEQ ID NOs:154-158) of target region 5 with the parvovirus B19 genotype 1 Au isolate (nucleotides 1406-1559 of SEQ ID NO:130 of FIG. 4E are shown), the genotype 2 A6 isolate (nucleotides 1205-1358 of SEQ ID NO:131 of FIG. 4E are shown), and the genotype 3 isolates V9 (nucleotides 1298-1451 of SEQ ID NO:132 of FIG. 4E are shown) and D91.1 (nucleotides 1293-1446 of SEQ ID NO:133 of FIG. 4E are shown).

FIG. 10 shows target region and oligonucleotide sequences derived from highly conserved regions of the parvovirus B19 genome.

DETAILED DESCRIPTION

Figure 8:
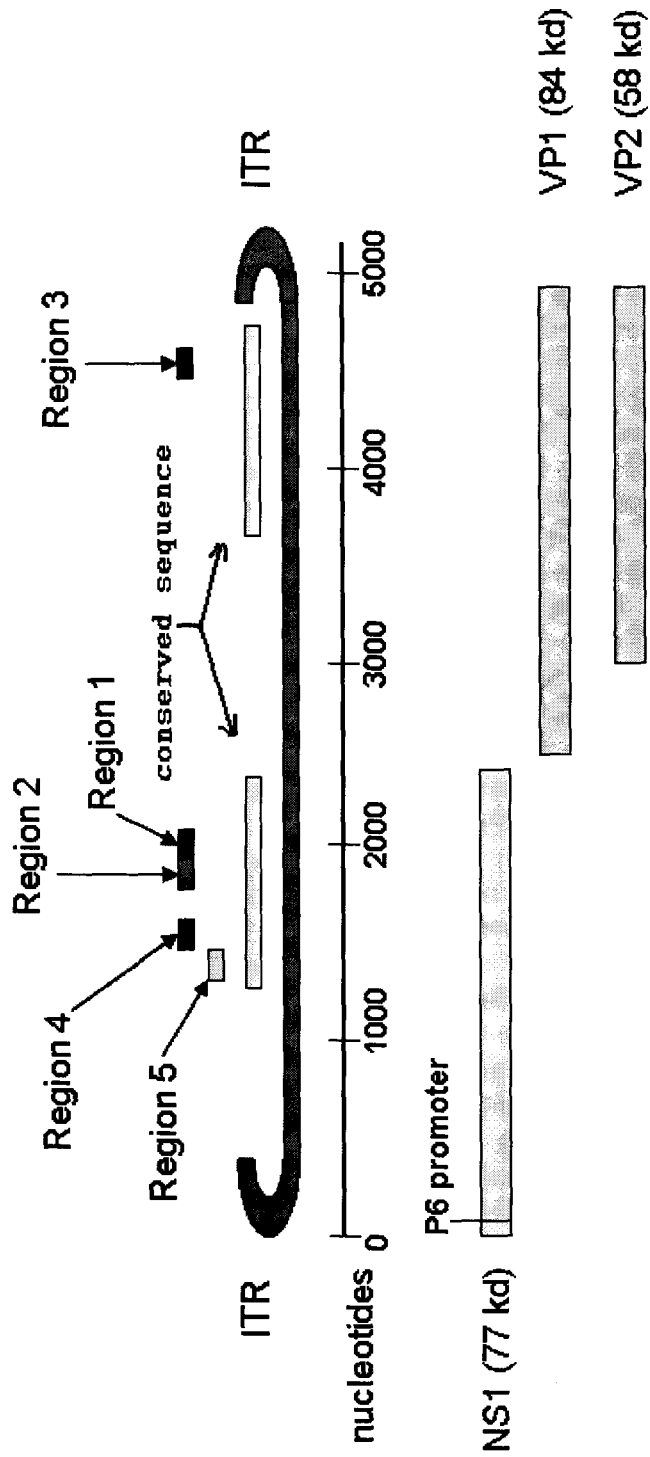
FIG. 8 shows a graphical depiction of the parvovirus B19 genome and transcription map showing conserved sequences and target regions. ITR—Inverted Terminal Repeat, NS 1 Non-Structural Protein 1, VP1—Viral Protein 1, and VP2—Viral Protein 2.

It has been found in accordance with this invention novel human *erythrovirus* variants (herein named the "D11," "P1," or "E3" variant) that contain previously unreported variations in viral DNA sequence. While the new variants described herein share some nucleic acid homology with other previously known variants of the human *erythrovirus* family, regions of the viral genome show divergence. This divergence indicates three previously unknown human *erythrovirus* variants that have eluded current detection methods, and knowledge of these variants provides for new methods for viral screening and detection.

The term "human *erythrovirus*" herein refers to viral members of the genus *Erythrovirus.*

The term "parvovirus B19" or "B19" herein refers to parvovirus B19 of the family Parvoviridae including genotypes 1, 2, and 3. For example, "parvovirus B19" at least includes parvovirus B19 genotype 1 (e.g., GenBank Accession Number: M13178) and related variants such as, for example, A6 parvovirus B19 genotype 2 (e.g., GenBank Accession Number: AY064476), V9 human parvovirus B19 genotype 3 (e.g., GenBank Accession Number: NC_004295), D91.1 parvovirus B19 genotype 3 (e.g., GenBank Accession Number: AY083234), and the parvovirus B19 variants (i.e., D11, E3, and P1) of the present invention. Fryer et al., (*Emerg. Infect. Diseases* 2006 12:151-154) discloses a phylogenetic analysis of members of the Parvoviridae subfamily including members of the *Erythrovirus* genus.

The term "universal base" herein refers to a moiety that may be substituted for any base. The "universal base" need not contribute to hybridization, but should not significantly detract from hybridization. Exemplary universal bases include, without limitation, inosine, 5-nitroindole and 4-nitrobenzimidazole.

In one embodiment, the present invention provides an isolated nucleic acid molecule comprising a nucleotide sequence as set forth in SEQ ID NO: 1, SEQ ID NO: 128, SEQ ID NO: 129, or a complement thereof. In some embodiments, the isolated nucleic acid molecule comprises single-stranded or double-stranded nucleic acid. In other embodiments, the isolated nucleic acid molecule comprises ribonucleic acid (RNA), deoxyribonucleic acid (DNA), or any combination thereof.

The term "nucleic acid" or "nucleic acid molecule" herein broadly refers to a polymer of any size comprising RNA, DNA, modified RNA or DNA, spliced messenger RNA, RNA or DNA mimetics, or combinations thereof (e.g., RNA/DNA hybrids). The term, therefore, includes polymers composed of naturally-occurring nucleotide bases, sugars and covalent internucleoside (backbone) linkages as well as nucleic acid molecules having non-naturally-occurring portions that function similarly. Further, the term "nucleic acid molecule" also includes polymers that are double-stranded, single-stranded, or any combination thereof.

In another aspect of the invention, an isolated nucleic acid molecule is provided that can anneal to DNA or RNA of the novel parvovirus B19 variant (i.e., D11) of the invention, as well as to one or more of other parvovirus sequences such as, for example, sequences of Au, A6, V9, or D91.1 parvovirus, thereby providing probes and primers useful for detection of multiple forms in a single test. Thus, according to this aspect, the invention relates to nucleic acid molecules useful for detection of parvovirus B19, including the novel variant characterized by the nucleic acid sequence of SEQ ID NO:1, and one or more variants known as Au, A6, V9, and D91.1 (see FIG. 4). Accordingly, the present invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), (SEQ ID NO: 60), (SEQ ID NO: 134), and (SEQ ID NO: 135).

In another aspect of the invention, an isolated nucleic acid molecule is provided that can anneal to DNA or RNA of the novel parvovirus B19 variants (i.e., D11, E3 and P1) of the invention, as well as to one or more other parvovirus sequences such as, for example, sequences of Au, A6, V9, or D91.1 parvovirus, thereby providing probes and primers useful for detection of multiple forms in a single test. Thus, according to this aspect, the invention relates to nucleic acid molecules useful for detection of parvovirus B19, including one or more of the novel variants characterized by the nucleic acid sequence of SEQ ID NO:1, SEQ ID NO:128, and SEQ ID NO: 129, and one or more variants known as Au, A6, V9, and D91.1. Accordingly, the present invention includes an isolated nucleic acid molecule comprising a sequence, or a complement thereof, present in an *erythrovirus* genome comprising a nucleotide sequence as set forth in SEQ ID NO:1, SEQ ID NO:128, and SEQ ID NO: 129, wherein the sequence is present in at least one other parvovirus genome. In one embodiment, the at least one other parvovirus genome is parvovirus B19 Au, A6, V9, and D91.1.

In another embodiment, the present invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 134), and (SEQ ID NO: 135).

In other embodiments, the present invention provides an isolated nucleic acid molecule consisting of a nucleotide sequence or a complement thereof, wherein the nucleotide sequence is selected from the group consisting of: (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), and (SEQ ID NO: 158).

In other aspects, the isolated nucleic acid molecules allow for discrimination between the newly discovered D11 variant of the present invention and other known parvovirus B19 such as, for example, Au, A6, V9, and D91.1. Thus, the present invention provides an isolated nucleic acid molecule comprising at least 12, at least 15, or at least 20, contiguous nucleotides of a nucleotide sequence or its complement thereof. The nucleotide sequence is based on regions within the genome of the newly discovered D11 variant of the present invention. The at least 12, at least 15, or at least 20, contiguous nucleotides can provide for specific and/or sensitive detection of a human *erythrovirus* in a sample. Accordingly, the present invention includes an isolated nucleic acid molecule comprising at least 12, at least 15, or at least 20 contiguous nucleotides of a nucleotide sequence or a complement thereof, wherein the nucleotide sequence is selected from the group consisting of: (SEQ ID NO: 61), (SEQ ID NO: 62), (SEQ ID NO: 63), (SEQ ID NO: 64), (SEQ ID NO: 65), (SEQ ID NO: 66), (SEQ ID NO: 67), (SEQ ID NO: 68), (SEQ ID NO: 69), (SEQ ID NO: 70), (SEQ ID NO: 71), (SEQ ID NO: 72), (SEQ ID NO: 73), (SEQ ID NO: 74), (SEQ ID NO: 75), (SEQ ID NO: 76), (SEQ ID NO: 77), (SEQ ID NO: 78), (SEQ ID NO: 79), (SEQ ID NO: 80), (SEQ ID NO: 81), (SEQ ID NO: 82), (SEQ ID NO: 83), (SEQ ID NO: 84), (SEQ ID NO: 85), (SEQ ID NO: 86), (SEQ ID NO: 87), (SEQ ID NO: 88), (SEQ ID NO: 89), (SEQ ID NO: 90), (SEQ ID NO: 91), (SEQ ID NO: 92), (SEQ ID NO: 93), (SEQ ID NO: 94), (SEQ ID NO: 95), (SEQ ID NO: 96), (SEQ ID NO: 97), (SEQ ID NO: 98), (SEQ ID NO: 99), (SEQ ID NO: 100), (SEQ ID NO: 101), (SEQ ID NO: 102), (SEQ ID NO: 103), (SEQ ID NO: 104), (SEQ ID NO: 105), (SEQ ID NO: 106), (SEQ ID NO: 107), (SEQ ID NO: 108), (SEQ ID NO: 109), (SEQ ID NO: 110), (SEQ ID NO: 111), (SEQ ID NO: 112), (SEQ ID NO: 113), (SEQ ID NO: 114), (SEQ ID NO: 115), (SEQ ID NO: 116), (SEQ ID NO: 117), (SEQ ID NO: 118), (SEQ ID NO: 119), (SEQ ID NO: 120), (SEQ ID NO: 121), (SEQ ID NO: 122), (SEQ ID NO: 123), (SEQ ID NO: 124), (SEQ ID NO: 125), (SEQ ID NO: 126), and (SEQ ID NO: 127).

In one embodiment, the nucleotide sequence is selected from the group consisting of (SEQ ID NO: 61), (SEQ ID NO: 64), (SEQ ID NO: 65), (SEQ ID NO: 66), (SEQ ID NO: 68), (SEQ ID NO: 70), (SEQ ID NO: 81), (SEQ ID NO: 84), (SEQ ID NO: 86), (SEQ ID NO: 87), (SEQ ID NO: 88), (SEQ ID NO: 89), (SEQ ID NO: 97), (SEQ ID NO: 102), (SEQ ID NO: 109), SEQ ID NO: 114), (SEQ ID NO: 119), (SEQ ID NO: 120), (SEQ ID NO: 121), and (SEQ ID NO: 127).

In other aspects, the isolated nucleic acid molecules allow for discrimination between the newly discovered variants of the present invention (i.e., D11, E3, and P1) and at least one other known parvovirus B19 such as, for example, Au, A6, V9, and D91.1. Thus, the present invention provides an isolated nucleic acid molecule comprising a sequence present in an *erythrovirus* genome or a complement thereof, wherein the genome comprises a nucleotide sequence as set forth in SEQ ID NO:1, SEQ ID NO:128 or SEQ ID NO: 129, wherein the sequence is not present in at least one other parvovirus genome. The nucleotide sequence is based on regions of the genome of the newly discovered D11, E3 and/or P1 variants of the present invention. The contiguous nucleotides can provide for specific and/or sensitive detection of a human *erythrovirus* in a sample.

In other aspects, the present invention provides an isolated nucleic acid molecule that anneals under a stringent condition to a polynucleotide comprising a nucleotide sequence as set forth in SEQ ID NO: 1 or a complement thereof, but does not anneal under the stringent condition to other DNA or RNA molecules that may be present in a test sample (i.e., binds specifically to parvovirus B19 nucleic acid). In one embodiment, the nucleotide sequence is as set forth in SEQ ID NO: 128 or a complement thereof. In another embodiment, the nucleotide sequence is as set forth in SEQ ID NO: 129 or a complement thereof. As used herein, a stringent condition is a highly stringent condition or a moderately stringent condition.

Stringency conditions are known to those skilled in the art and can be found, for example, in *Current Protocols in Molecular Biology* (1999. Ausubel F M, Brent R, Kingston R E, Moore D D, Seidman J G, Smith J A, Struhl K, editors. John Wiley & Sons, Inc.) or Sambrook et al., *Molecular Cloning: A Laboratory Manual*, New York: Cold Spring Harbor Press (1989). Stringency conditions relate to the set of conditions under which nucleic acid hybrids comprising double-stranded regions are formed and/or maintained. It is well known in the art that two complementary single-stranded nucleic acids (DNA or RNA) can anneal to one another so that complexes called hybrids are formed. Formation or subsequent stability of a formed hybrid can be affected by the conditions under which hybridization (i.e., annealing) occurs, by any wash conditions subsequent to hybridization, or both. Thus, through one or more nucleic acid hybridization steps, which can precede one or more wash steps, two nucleic acid sequences having a certain degree of complementary identity to one another can anneal together and form a hybrid comprising one or more contiguous regions of double-stranded nucleic acid. Further, formation of hybrids can occur in a variety of environments such as, for example, in solution, with one component immobilized on a solid support such as a nylon membrane, nitrocellulose paper, polystyrene, or in situ (e.g., in suitably prepared cells or histological sections).

It is well known in the art that a number of factors affect hybrid formation and/or stability such as, for example, temperature, duration, frequency, or salt or detergent concentration of the hybridization and/or wash conditions. Thus, for example, the stringency of a condition can be primarily due to the wash conditions, particularly if the hybridization condition used is one which allows less stable hybrids to form along with stable hybrids (e.g., wash conditions at higher stringency can remove less stable hybrids). In general, longer sequences require higher temperatures for proper annealing, while shorter sequences need lower temperatures. Hybridization generally depends on the ability of denatured nucleic acids to reanneal when complementary strands are present in a favorable environment at temperatures below their melting temperature. The higher the degree of desired homology between two sequences, the higher the relative temperature which can be used. As a result, it follows that higher relative temperatures would tend to make the reaction conditions more stringent, while lower temperatures less so.

Generally, stringency can be altered or controlled by, for example, manipulating temperature and salt concentration during hybridization and washing. For example, a combination of high temperature and low salt concentration increases stringency. The skilled artisan will recognize how to adjust the temperature, ionic strength, etc. of the stringent condition as necessary to accommodate factors such as polynucleotide length and the like.

A "highly stringent condition," as defined herein, can be identified by a condition that comprises 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a wash consisting of 0.1×SSC at 55° C.

A "moderately stringent condition," as defined herein, can be identified by washing and/or hybridization conditions less stringent than those described above for a highly stringent condition. An example of a moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing in 1×SSC at about 35-50° C.

Sometimes, nucleic acid duplex or hybrid stability is expressed as the melting temperature or $T_m$, which is the temperature at which 50% of one nucleic acid dissociates from a nucleic acid duplex. Accordingly, this melting temperature can be used to define the required stringency conditions. If sequences are related and substantially identical to each other, rather than identical, then it can be useful to first establish the lowest temperature at which only homologous annealing occurs with a particular concentration of salt (e.g., SSC or SSPE). Then, assuming 1% mismatching results in a 1° C. decrease in the $T_m$, the temperature of the final wash in the hybridization reaction is reduced accordingly (for example, if sequences having >95% identity with each other are sought, the final wash temperature is decreased by 5° C.). In practice, the change in $T_m$ can be between 0.5° C. and 1.5° C. per 1% mismatch.

In other aspects, the present invention provides an isolated nucleic acid molecule that anneals under a highly stringent condition to a polynucleotide comprising a nucleotide sequence as set forth in SEQ ID NO: 1 or a complement thereof, wherein the isolated nucleic acid molecule does not anneal under the highly stringent condition to a DNA or a RNA of parvovirus B19 Au, A6, V9, or D91.1 variant. In one embodiment, the polynucleotide comprises the nucleotide sequence as set forth in SEQ ID NO: 128 or a complement thereof. In another embodiment, the polynucleotide comprises the nucleotide sequence as set forth in SEQ ID NO: 129 or a complement thereof. Stringency conditions are as described above.

The annealing portion of a hybridizing nucleic acid molecule can vary in length but is typically at least about 6, illustratively, at least about 10, 12, 15, 20, 25, 30, 50, 60, 70, 80, 90, 100, 150, 200, 250, 300, 400, 500, 600, 700, 800, 900, or 1000 nucleotides in length. However, binding enhancers such as minor groove binding nucleic acids can allow annealing to shorter nucleic acid targets with increased sequence-specificity compared to ordinary length nucleic acids (Kutyavin I V, et al., *Nucleic Acid Research* 2000 28:655-661). The annealing portion of the annealing nucleic acid is at least 60%, e.g., at least 70%, 80%, 95% or at least 98% identical to the sequence of a portion or all of a nucleic acid expressly described herein, or its complement. Annealing nucleic acids of the type described herein can be used, for example, as cloning probes, primers (e.g., a PCR primer), or diagnostic probes.

As described above, oligonucleotide primers and probes can be derived from the nucleic acid sequences disclosed herein. In various embodiments, primers and probes are used in combination with each other. The present invention finds use in a variety of different applications including, but not limited to, research, medical, and diagnostic applications.

In some embodiments, primers and probes can be designed from regions of SEQ ID NO: 1, SEQ ID NO: 128, or SEQ ID NO:129, wherein the primers and probes each comprise one or more conserved nucleotides also present in a corresponding region of the genome of another human erythroviruses such as parvovirus B19 Au, A6, V9, and D91.1. For example, a nucleotide sequence alignment can be performed with at least two parvovirus sequences using, e.g., a computer algorithm to determine identical contiguous nucleotide sequences common to the at least two parvovirus. Accordingly, the primers and probes can provide for reagents for use in, for example, a parvovirus detection assay or kit thereby expanding the repertoire of parvovirus variants that can be detected by the assay or kit.

In another embodiment, the present invention provides a kit comprising at least one primer and at least one probe, wherein the at least one primer comprises a primer nucleic acid sequence as set forth in (SEQ ID NO: 136), (SEQ ID NO: 137), (SEQ ID NO: 139), (SEQ ID NO: 140), (SEQ ID NO: 142), (SEQ ID NO: 144), (SEQ ID NO: 145), (SEQ ID NO: 146), (SEQ ID NO: 149), (SEQ ID NO: 151), (SEQ ID NO: 152), (SEQ ID NO: 154), or (SEQ ID NO: 155), wherein the at least one probe comprises a probe sequence consisting of: (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In another embodiment, the kit comprises a forward primer, a reverse primer, and a probe, wherein the forward primer comprises a forward primer nucleic acid sequence as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO:154, wherein the reverse primer comprises a reverse primer nucleic acid sequence as set forth in (SEQ ID NO: 137), (SEQ ID NO: 140), (SEQ ID NO: 144), (SEQ ID NO: 146), (SEQ ID NO: 152), or (SEQ ID NO:155, wherein the probe comprises a probe nucleic acid sequence as set forth in (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), (SEQ ID NO: 158), or comple-ments thereof. In some embodiments, the probe nucleic acid sequence is as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In some aspects, the present invention provides a method for detecting a parvovirus B19 in a sample. The method comprises:

a) performing PCR with at least a portion of the sample using a forward primer having a forward primer nucleic acid sequence and a reverse primer having a reverse primer nucleic acid sequence, wherein the forward primer nucleic acid sequence is as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO:154, wherein the reverse primer nucleic acid sequence is as set forth in (SEQ ID NO: 137), (SEQ ID NO: 140), (SEQ ID NO: 144), (SEQ ID NO: 146), (SEQ ID NO: 152), or (SEQ ID NO:155); and b) determining the presence or absence of an amplicon, wherein the presence of the amplicon is indicative of the presence of the parvovirus B19 in the sample. In one embodiment, determining comprises annealing an oligonucleotide to the amplicon, wherein the oligonucleotide comprises a sequence as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153); (SEQ ID NO: 156), (SEQ ID NO: 157), (SEQ ID NO: 158), or complements thereof. In one embodiment, the oligonucleotide further comprises a detectable label. In another embodiment, the PCR is a real-time PCR.

In some embodiments, primers and probes can be designed from regions of SEQ ID NO: 1, SEQ ID NO: 128, or SEQ ID NO:129 that comprise one or more unique nucleotides as compared to the corresponding region of the genome of other human erythroviruses such as parvovirus B19 Au, A6, V9, and D91.1. Accordingly, the primers and probes can provide for assays that facilitate detection of a parvovirus B19 as well as provide for assays that distinguish between one or more of the new variants disclosed herein or other previously known human erythroviruses such as parvovirus B19 Au, A6, V9, and D91.1. Accordingly, the primers and probes can provide for a more specific parvovirus detection assay that can discriminate from among the parvovirus variants.

Another example of a hybridization assay probe is a structure referred to as a "molecular beacon," which is described, for example, in U.S. Pat. No. 5,925,517. Molecular beacons are oligonucleotide hybridization probes that comprise a label pair and form a stem-and-loop structure. The loop component comprises a probe sequence that is complementary to a target sequence. The stem comprises an affinity pair (or nucleic acid arms) that hold the probe in a closed conformation in the absence of a target nucleic acid sequence. The stem is formed by the annealing of complementary arm sequences that are located on either side of the probe sequence. Hybridization of the target nucleic acid and the target complement sequence separates the members of the affinity pair, thereby shifting the probe to an open conformation. The shift to the open confirmation is detectable due to reduced interaction of the label pair, which may be, for example, a fluorophore and a quencher (e.g., DABCYL and EDANS).

The simultaneous use of two or more probes using donor-acceptor energy transfer is known in the art. Accordingly, molecular beacons can be synthesized that possess differently colored fluorophores, enabling assays to be carried out that simultaneously detect different targets in the same reaction. For example, multiplex assays can contain a number of different primer sets, each set enabling the amplification of a unique gene sequence from a different pathogenic agent, and a corresponding number of molecular beacons can be present, each containing a probe sequence specific for one of the amplicons, and each labeled with a fluorophore of a different color. The color of the resulting fluorescence, if any, identifies the pathogenic agent in the sample, and the number of amplification cycles required to generate detectable fluorescence provides a quantitative measure of the number of target organisms present. If more than one type of pathogen is present in the sample, the fluorescent colors that occur identify which are present. Moreover, due to the inherent design of gene amplification assays, the use of molecular beacons enables the abundance of a rare pathogen to be determined in the presence of a much more abundant pathogen.

In general, primers can provide for specific amplification (e.g., by PCR) of a target nucleic acid to produce an amplification product (also referred to as an "amplicon"). In one embodiment, the target nucleic acid is DNA or RNA of the novel human *erythrovirus* disclosed herein. In some embodiments, the target nucleic acid comprises a genome comprising a nucleotide sequence as set forth in SEQ ID NO: 1. In other embodiments, the target nucleic acid comprises an RNA molecule transcribed from a genome comprising a nucleotide sequence as set forth in SEQ ID NO: 1. In one embodiment, the genome comprises the nucleotide sequence as set forth in SEQ ID NO: 128 or SEQ ID NO: 129.

In some embodiments, a primer sequence can be at least about 10 nucleotides in length, illustratively about 10 to about 100, about 12 to about 75, about 14 to about 65, about 16 to about 60, about 20 to about 55, about 25 to about 50, or about 30 to about 45, and the like. In one embodiment, a primer sequence is about 15 to about 20 nucleotides in length.

Probes are generally designed so as to have a nucleotide sequence complementary to one or more variant nucleotides within a target region sequence. Probes suitable for use in amplification-based detection methods can be designed from any sequence positioned within the sequence of an amplification product that would be produced using two selected primers. In various embodiments, a probe sequence can be at least about 10 nucleotides in length, illustratively about 10 to about 100, about 12 to about 75, about 14 to about 65, about 16 to about 60, about 20 to about 55, about 25 to about 50, or about 30 to about 45, and the like. In one embodiment, a probe sequence is about 15 to about 20 nucleotides in length.

Depending on the number of nucleotide residues, a nucleic acid molecule also can be referred to as an "oligonucleotide" or "oligomer." The term "oligonucleotide" or "oligomer" typically refers to a nucleic acid molecule having a relatively short sequence of nucleotides. For example, an oligonucleotide can be about 5 to about 500 nucleotide residues in length. Oligonucleotides, which can be double-stranded or single-stranded, may be used as single-stranded probes for detecting complementary DNA or RNA because they can bind readily to their complements. Non-limiting examples of procedures that use oligonucleotides are nucleic acid testing (NAT), DNA microarrays, amplified fragment-length polymorphism (AFLP) analysis, fragment analysis, Southern blots, and fluorescent in situ hybridization (FISH). Oligonucleotides composed of DNA are often used in the polymerase chain reaction (PCR), a procedure well-known to those skilled in the art. In this regard, the oligonucleotide also can be referred to as a "primer," which is a short piece of DNA that binds to its complementary target sequence. This generates a place for a polymerase to bind and extend the primer by the addition of nucleotides to make a complementary copy of the target sequence. An oligonucleotide can also be referred to as a "probe" which is a short piece of DNA or RNA that can be used to detect and identify specific DNA or RNA molecules bearing the complementary sequence. Probe detection is achieved through fluorescence, colorimetry, radioactivity, antigen binding, or enzymatic activity.

In some embodiments, the isolated nucleic acid molecule is an oligonucleotide having at least about 5 nucleotide residues in length, illustratively about 5 to about 500, about 8 to about 400, about 10 to about 300, about 12 to about 200, about 14 to about 100, about 16 to about 90, about 18 to about 80, about 20 to about 70, about 25 to about 60, or about 30 to about 50.

One skilled in the art will appreciate that the isolated nucleic acid molecules of the present invention can be obtained by standard molecular biology techniques such as PCR and others described in *Current Protocols in Molecular Biology* (1999. Ausubel F M, Brent R, Kingston R E, Moore D D, Seidman J G, Smith J A, Struhl K, editors. John Wiley & Sons, Inc.) or by chemical synthesis or by nucleic acid analogs.

Methods involving chemical synthesis may be automated and commercially available and can include, for example, phosphodiester, phosphotriester, or phosphoramidite methods. U.S. Pat. Nos. 4,458,066; 4,415,732; and *Meth. Enzymol.* 1979 68:90 and 109, which are incorporated herein by reference, disclose examples of chemical synthesis methods. Chemical nucleic acid synthesis allows for the incorporation of unnatural or modified bases, as well as a variety of labeling moieties, into a nucleic acid molecule. Further, modified backbone chemistries such as, for example, peptide linkages, phosphorothioates, phosphoroamidates, phosphotriesters, 2'-O-Methyl RNA, 2'-O-Mt RNA, P-Ethoxy DNA, and P-Ethoxy 2'-O-Mt RNA are also readily available and known in the art. Furthermore, the uses of cross-linkable probes in nucleic acid hybridization assays to cross-link to target sequences are known in the art. For example, compounds based on furocoumarin or psoralen attached to nucleic acid molecules through adduct formation are described in U.S. Pat. No. 4,826,967 and U.S. Pat. No. 5,082,934, both incorporated herein by reference, describes a photoactivatable nucleoside analogue comprising a coumarin moiety linked through its phenyl ring to the 1-position of a ribose or deoxyribose sugar moiety in the absence of an intervening base moiety.

Nucleic acid analogs and mimics have similar chemical structures as native nucleic acid molecules but with unique modifications. Nucleic acid analogs, such as locked nucleic acids (LNAs), peptide nucleic acids (PNAs), and morpholinos, improve the capabilities of traditional nucleic acid molecules beyond the limitations associated with standard nucleic acids chemistry (Karkare S and Bhatnagar D. *Appl. Microbiol. Biotechnol.* 2006 71:575-586.) Such nucleic acid analogs greatly expand and improve the capabilities to detect and identify related nucleic acid sequences.

In some aspects, an isolated nucleic acid molecule of the present invention further comprises one or more heterologous nucleotides. The term "heterologous nucleotides" herein refers to a nucleotide or nucleotides that are not a natural part of the isolated nucleic acid molecule but which are naturally or artificially joined to the isolated nucleic acid molecule. Examples of a heterologous nucleic acid sequence include, but is not limited to, a vector sequence, a sequence that is complementary to a base sequence of a purification probe, a control sequence such as, for example, an enhancer or a promoter sequence (i.e., a sequence that is recognized by an RNA polymerase that binds to that sequence and initiates transcription to produce RNA transcripts), and a sequence comprising one or more restriction enzyme sites.

The term "control sequence" herein refers to sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, messenger RNA splicing signals, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

In one embodiment, the one or more heterologous nucleotides comprise a sequence that is complementary to a base sequence of a purification probe. The purification probe can be joined to solid supports such as, for example, a matrix or particles free in solution. Non-limiting examples of a solid support include nitrocellulose, nylon, glass, polyacrylate, mixed polymers, polystyrene, silane polypropylene, and magnetically-attractable particles. For example, the purification probe, which may comprise a DNA or RNA sequence, can be labeled with amine or biotin tags via a cross-linker. These biotin or amine labeled purification probes are then amenable to immobilization and detection strategies that allow in vitro nucleic acid:nucleic acid or protein:nucleic acid interactions. Thus, annealing of the heterologous segment of the isolated nucleic acid molecule with its complementary base sequence of the purification probe can facilitate sample purification of molecules that anneal to the virus-specific sequence segment of the isolated nucleic acid molecule. U.S. Pat. No. 6,534,273, incorporated herein by reference, describes a method for capturing a target nucleic acid molecule in a sample onto a solid support.

In one embodiment, the isolated nucleic acid molecules of the present invention are joined to a solid support such as those described above.

In some embodiments, the one or more heterologous nucleotides comprise one or more repeating base sequences, for example, one or more repeating base sequences that are complementary to one or more repeating base sequences of the purification probe. A repeating base sequences can be a regularly repeating base sequence, such as those formed, for example, by nucleic acid homopolymers of poly-adenine ($A_n$), poly-thymine ($T_n$), poly-cytosine ($C_n$), poly-guanine ($G_n$), and poly-uridine ($U_n$). Repeating sequences also can include mixed polymers, such as AT repeats ($[AT]_n$), and the like.

The number of bases of the repeating base sequence of the one or more heterologous nucleotides of the isolated nucleic acid molecule can be equal to, greater than, or less than the number of bases of the repeating base sequence of the purification probe. The lengths of the complementary repeating sequences can determine the melting temperature ($T_m$) of the heterologous segment:purification probe complex. In one embodiment, the repeating base sequence of the heterologous segment is longer than the complementary repeating base sequence of the purification probe. In another embodiment, the repeating base sequence of the heterologous segment or the purification probe can be at least about 5 bases in length, illustratively about 5 to about 40, about 10 to about 30, or about 15 to about 20, and the like.

In other embodiments, the one or more heterologous nucleotides comprise an operably linked control sequence. In one embodiment, the control sequence is an enhancer or a promoter sequence that is specifically recognized by an RNA polymerase that binds to that sequence and initiates transcription to produce RNA transcripts. Non-limiting examples of promoters recognized by an RNA polymerase include promoters such as T3, T7, or SP6. Thus, an isolated nucleic acid molecule can be used in a variety of nucleic acid based assays including assays that use an RNA polymerase to produce multiple RNA transcripts such as, for example, transcription-mediated amplification (TMA) assay as described in Nature 350:91-92 (1991); and U.S. Pat. No. 5,399,491, both incorporated herein by reference.

Optionally, the isolated nucleic acid molecules of the present invention can be coupled to a label that can be detected. The label can be joined directly or indirectly to the isolated nucleic acid molecule. The labeling of a nucleic acid can be performed by covalently attaching a detectable group (label) to either an internal or terminal position, for example. One skilled in the art knows that there are a variety of ways for derivatizing oligonucleotides with reactive functionalities that permit the addition of a label. A number of approaches are available for directly attaching labels to nucleic acid molecules and for biotinylating probes so that radioactive, fluorescent, chemiluminescent, enzymatic, or electron dense labels can be attached via avidin. Non-limiting examples of references describing labels and methods for labeling nucleic acids include U.S. Pat. No. 4,605,735; U.S. Pat. No. 4,757,141; U.S. Pat. No. 6,965,020; Nucl. Acids Res. 5:363 (1978); Nucl. Acids Res. 13:1529 (1985); Nucl. Acids Res. 15:3131 (1987); Nucl. Acids Res. 15:6455 (1987); Nucl. Acids Res. 13:4485 (1985); Nucl. Acids Res. 15:4837 (1987); and Anal. Biochem. 169:1-25 (1988), which are incorporated herein by reference for their disclosure relating to labeling of nucleic acids.

The isolated nucleic acid molecules of the present invention may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Further, a viral protein encoded by an isolated nucleic acid molecule comprising an open reading frame or a complement thereof, wherein the open reading frame is comprised in SEQ ID NO: 1, SEQ ID NO 128, or SEQ ID NO: 129 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the protein-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, a factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179), or the signal described in WO/90/13646. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells is those that enable the identification of cells competent to take up the viral protein-encoding nucleic acid, such as DHFR or thymidine kinase. An appropriate host cell when wild-type DHFR is employed is the CHO cell line deficient in DHFR activity, prepared and propagated as described by *Proc. Natl. Acad. Sci. USA* 77:4216 (1980). A suitable selection gene for use in yeast is the trp1 gene present in the yeast plasmid YRp7 as described by *Nature* 282:39 (1979); *Gene* 7:141 (1979); and *Gene* 10:157 (1980). The trp1 gene provides a selection marker for a mutant strain of yeast lacking the ability to grow in tryptophan, for example, ATCC No. 44076 or PEP4-1 as described by *Genetics* 85:12 (1977).

Expression and cloning vectors usually contain a promoter operably linked to the viral-protein-encoding nucleic acid sequence to direct mRNA synthesis. Promoters recognized by a variety of potential host cells are well known. Promoters suitable for use with prokaryotic hosts include the β-lactamase and lactose promoter systems as described by *Nature* 275:615 (1978) and *Nature* 281:544 (1979), alkaline phosphatase, a tryptophan (trp) promoter system as described by *Nucl. Acids Res.* 8:4057 (1980) and EP 36,776, and hybrid promoters such as the tac promoter as described in *Proc. Natl. Acad. Sci. USA* 80:21 25 (1983). Promoters for use in bacterial systems also will contain a Shine-Dalgarno (S.D.) sequence operably linked to the DNA encoding the viral protein.

Examples of suitable promoting sequences for use with yeast hosts include the promoters for 3-phosphoglycerate kinase described in *J. Biol. Chem.* 255:2073 (1980) or other glycolytic enzymes described in *J. Adv. Enzyme Reg.* 7:149 (1968) and *Biochemistry* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Viral protein transcription from vectors in mammalian host cells is controlled, for example, by promoters obtained from the genomes of viruses such as polyoma virus, fowlpox virus (GB 2,211,504), adenovirus (such as Adenovirus 2), bovine papilloma virus, avian sarcoma virus, cytomegalovirus (CMV), a retrovirus, hepatitis-B virus, and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the viral protein by higher eukaryotes may be increased by inserting an enhancer sequence into the vector. Enhancers are cis-acting elements of DNA, usually about 10 to about 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the CMV early promoter enhancer, the polyoma enhancer on the late side of the replication origin, and adenovirus enhancers. The enhancer may be spliced into the vector at a position 5' or 3' to the viral protein coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly upstream of the polyadenylation site in untranslated regions of eukaryotic or viral DNAs or cDNAs. These regions contain nucleotide segments transcribed as polyadenylated fragments in the untranslated portion of the mRNA encoding the viral protein.

Other methods, vectors, and host cells suitable for adaptation to the synthesis of viral proteins in recombinant vertebrate cell culture are described in *Nature* 293:620 625 (1981); *Nature* 281:4046 (1979); EP 117,060; and EP 117,058.

A host cell can be transfected or transformed with the isolated nucleic acid molecules of the present invention (or with expression or cloning vectors comprising them) and cultured in conventional nutrient media modified as appropriate for inducing viral production, inducing promoters, selecting transformants, or amplifying the genes encoding the desired sequences. In one embodiment, the host cell is an erythroid cell. In another embodiment, the erythroid cell is a human erythroid cell.

The culture conditions, such as media, temperature, pH, and the like, can be selected by the skilled artisan without undue experimentation. In general, principles, protocols, and practical techniques for maximizing the productivity of cell cultures can be found in M. Butler, Mammalian Cell Biotechnology: a Practical Approach, IRL Press (1991) and Sambrook et al., supra.

Methods of eukaryotic cell transfection and prokaryotic cell transformation are known to the ordinarily skilled artisan, for example, $CaCl_2$, $CaPO_4$, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by *Gene* 23:315 (1983) and WO 89/05859. For mammalian cells without such cell walls, the calcium phosphate precipitation method described in *Virology* 52:456 457 (1978) can be employed. General aspects of mammalian cell host system transfections are described in U.S. Pat. No. 4,399, 216. Transformations into yeast are typically carried out according to the method as described in *J. Bact.* 130:946 (1977) and *Proc. Natl. Acad. Sci.* (*USA*) 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see, for example, *Methods in Enzymology* 185:527 (1990) and *Nature* 336:348 (1988).

In various other aspects, the present invention provides an isolated nucleic acid molecule comprising an open reading frame or its complement thereof, wherein the open reading frame is comprised in SEQ ID NO: 1. In one embodiment, the open reading frame is comprised in SEQ ID NO: 128. In another embodiment, the open reading frame is comprised in SEQ ID NO: 129.

In some aspects, the present invention provides an isolated human *erythrovirus* having a genome comprising a nucleotide sequence as set forth in SEQ ID NO: 1. In one embodiment, the nucleotide sequence is as set forth in SEQ ID NO:128 or SEQ ID NO:129.

In other aspects, the present invention provides a kit. The kit can be developed using the nucleic acid sequences disclosed herein. These sequences can be used as primers in nucleic acid amplification reactions, and/or as probes in a nucleic acid hybridization method. The kits are useful for determining the presence of a parvovirus nucleic acid sequence in a sample. Components in the kit can either be obtained commercially or made according to well known methods in the art. In addition, the components of the kit can be in solution or lyophilized as appropriate. In one embodiment, the components are in the same compartment, and in another embodiment, the components are in separate compartments. In the preferred embodiment, the kit further comprises instructions for use.

The following examples are provided for illustration only.

EXAMPLES

Example 1

Detection of Parvovirus B19 D11 Variant by PCR

The D11 variant is detected from a biological source such as, for example, plasma, blood, bone marrow, or tissue sample for organ screening.

Approximately 1 ml of plasma or other biological source sample is added to approximately 200 μl of a buffered solution containing reagents designed to facilitate the precipitation of parvovirus B19 virions. To facilitate capsid disruption and pelleting, the buffered solution contains a chaotropic agent (e.g., guanidine isothiocyanate) and/or a detergent (e.g., sodium dodecyl sulfate (SDS)). Samples are mixed thoroughly by vortexing or inversion, and centrifuged. The supernatant is discarded and approximately 600 μl of a buffered solution containing a chaotropic agent such as, for example, guanidine thiocyanate is added to the pellet to completely disrupt the viral capsids. The parvovirus B19 DNA is then precipitated using, for example, approximately 700 μl isopropanol. Samples are thoroughly mixed by vortexing or inversion, and centrifuged using conditions that allow for the majority of the DNA to be recovered. Optionally, the pellet is washed, for example with approximately 1 ml 70% ethanol. After centrifugation, the parvovirus B19 variant DNA is recovered following resuspension of the pellet in a buffered solution to a volume (e.g., 200 μl) that allows for subsequent DNA amplification.

The D11 variant nucleic acid is amplified via PCR using techniques well-known in the art. For example, about 35 to 45 μl of a working master mix comprising of i) a buffer solution, ii) D 11 variant-specific oligonucleotides of which one is biotinylated on its 5' end, iii) dideoxy-trinucleotides, and iv) DNA polymerase is added into a PCR tube or plate for amplification. Five to 15 μl of the resuspended sample is added to the PCR tube or plate containing the working master mix. Using a standard PCR thermocycler, such as the BioRad iCycler (Bio-Rad Laboratories), the samples and all relevant controls are subjected to PCR amplification. The PCR amplification condition comprises, for example, i) a step of denaturation (e.g. 94° C. for 60 seconds), ii) about forty cycles comprising thermal denaturation (e.g. 94° C. for 15 seconds) and polymerase extension (e.g. 65° C. for 30 seconds), and iii) a final step of polymerase extension (e.g. 60° C. for 7 minutes).

Following amplification, the resulting amplicons are detected using a variety of methods well known in the art. For example, the amplicons are detected by first denaturing the resulting amplified product and annealing the denatured nucleic acid sequences with complementary RNA probes to form RNA:DNA complexes. RNA probes are designed from the parvovirus B19 variant sequence. The complexes will be captured on streptavidin-coated plates and detected and/or quantified using, for example, antibodies directed to the complexes in an ELISA format.

There are a variety ELISA formats known in the art. For example, fifty μl of a sample diluent (e.g. Multiprep Specimen Diluent (MP DIL) (Roche Molecular Systems, Branchburg, N.J.)) is placed into a 96 well plate and 25 μl of a denaturation reagent (1.25 N NaOH) is added. Five to 10 μl of the amplified material is then added to each well containing the sample diluent and denaturation solution. After all the samples are transferred, the ELISA plates are covered and the samples mixed by placing the plates on a rotary shaker for about 30 to 60 seconds. The plates are incubated at room temperature for 10 to 20 minutes before adding about 25 μl of the RNA probe (500 pmole/L in neutralization buffer) to each well. After all the samples are transferred, the plates are covered and the samples mixed by placing the plates on a rotary shaker for about 30 to 60 seconds followed by incubation at 65° C. for 25 to 35 minutes.

After incubation, the contents of each well is transferred into another 96 well plate previously coated with streptavidin. After all the samples are transferred, the plate(s) are covered and the samples are mixed by placing the plates on a rotary shaker for 25 to 35 minutes. This latter step allows for the RNA:DNA complexes comprising the incorporated biotin label to bind to the streptavidin-coated plate. After the incubation and removal of the contents of the well, 100 μl of an appropriately diluted antibody coupled to alkaline phosphatase that is targeted to recognize the RNA:DNA complexes is added to each well and incubated at room temperature for about 25 to 35 minutes on a rotary shaker.

Following incubation, each well is washed about 4-5 times with a buffered wash solution (e.g. 80 mM Tris pH 7.5, 150 mM NaCl, 0.05% Tween 20) to remove non-binding reagents. The RNA:DNA:antibody complexes that are bound to the plate are detected using an alkaline phosphatase substrate such as, for example, p-nitrophenyl phosphate (pNPP). The rate of reaction or intensity of the signal is measured at 405 nanometers using a standard ELISA plate reader. The amount of color corresponds to the relative amount of the RNA:DNA: antibody complex present in the well. The quantity of the D11 variant is interpolated from a standard curve comprised of various concentrations of the D11 variant or suitable control standard (e.g. calibrated plasmids, amplicons, etc.) that are treated in the same manner as the samples to be determined.

Example 2

Detection of Parvovirus B19 D11 Variant by Real-Time PCR

The D11 variant is also detected and/or quantified using real-time PCR, which is well known in the art.

Samples comprising viral nucleic acids are prepared as described above. Amplification is carried out in a PCR tube or plate using an appropriate volume of PCR working master mix. The working master mix comprises a buffer solution comprising i) D11 variant specific oligonucleotides of which one contains a fluorescent dye on its 5' end and a quencher near or at its 3' end, ii) deoxyribonucleotides, and iii) a thermophilic DNA polymerase with 5' to 3' exonuclease activity. Five to 15 µL of the resuspended samples are added to the PCR tube or plate containing the working master mix for amplification. Using real-time PCR such as, for example, the AB7300 Real-Time PCR System (Applied Biosystems), the samples and all relevant controls are amplified.

Real-time PCR amplification conditions comprise, for example, i) a step of denaturation (e.g. 94° C. for 60 seconds), ii) about forty cycles comprising thermal denaturation (e.g. 94° C. for 15 seconds) and polymerase extension (e.g. 65° C. for 30 seconds), and iii) a final step of polymerase extension (e.g. 60° C. for 7 minutes).

During amplification, the resulting amplicons are detected using an appropriate energy source to excite the fluorescent dye cleaved from the oligonucleotide and filters to capture the fluorescence emitted. This detection is performed during each amplification cycle by measuring the relative fluorescence of the target and comparing it to the background fluorescence of the sample and instrument. This relative fluorescence is plotted against a standard curve derived using known amounts of a characterized molecular standard and a quantity is assigned to the sample based on the known quantity of the controls used to generate the standard curve.

Example 3

Parvovirus B19 D11 Variant Infectivity Assay

To determine infectivity of the D11 variant, primer(s) and a probe are used to amplify and detect an amplicon from the D11 variant mRNA. The amplicon serves as an indicator of viral replication as described in *Virology* 301:374-380 (2002).

Cultured cells susceptible to parvovirus B19 infection or replication are either infected with D11 variant or transfected with the viral DNA. Following viral gene expression, the cells are lysed by a suitable buffer such as, for example, the guanidine-based buffer described above. Nucleic acid is recovered from the lysate by alcohol-based precipitation or by binding to a matrix in a column (e.g., Promega SV Total RNA Isolation System) or particle format such as magnetic beads (e.g., Ambion's MagMAX Viral RNA Isolation Kits). The recovered nucleic acid are washed to remove cellular debris and resuspended in a suitable solution, such as water or TE buffer. A fraction of the recovered nucleic acid is treated with DNase to degrade DNA. Accordingly, two types of samples are prepared, one with total infected cell nucleic acid and one enriched for infected cell RNA.

Oligonucleotide primer or primers and an intervening probe comprising DNA sequences unique to the D11 variant described herein are used to amplify and detect D11 variant RNA in the samples. The viral RNA is reverse transcribed into cDNA using standard techniques well known in the art. For example, specific primers or random oligomers are used to prime the reverse transcription step using a reagent such as, for example, SuperScript III Reverse Transcriptase (Invitrogen).

Following reverse transcription of viral RNA into cDNA, the D11 variant nucleic acid is amplified using standard amplification technologies such as, for example, PCR, Transcription Mediated Amplification (TMA), or Ligase Chain Reaction. The amplified parvovirus B19 variant product is detected following hybridization to a labeled complementary oligonucleotide probe comprising a label such as, for example, a radioactive, a fluorescent, or a biotin label. The label, and hence the variant, is detected, for example, by direct detection of the label, by release of fluorescence during amplification in a TaqMan reaction, or through an indirect detection such as binding of an enzyme to the biotin or binding of a labeled antibody to the probe. Alternatively, one can target regions that result in spliced mRNAs. The shorter amplified mRNA target can be readily differentiated from native DNA template using methods that discriminate nucleic acids based on length.

Example 4

Detection of Parvovirus B19 D11 Variant without Prior Amplification

The D11 variant is detected and/or quantified using non-amplification techniques well known in the art. These methods allow detection of very low abundance nucleic acid sequences due to detection of single molecules with a high signal-to-noise ratio.

For example, the polymerase extension reaction, as described in *Anal. Chem.* 76:4169 (2004), is used to detect parvovirus B19 variants in samples prepared as described above. Highly fluorescent nucleic acid reporter molecules are made based on a unique sequence of the parvovirus B19 variant target nucleic acid as template. For example, the reporter molecule is made by annealing an oligonucleotide primer unique to the D11 variant to the target. The primer is then extended with a DNA polymerase and free oligonucleotides. One of these free oligonucleotides is labeled with a fluorophore. Fluorescence detection indicates the presence of the D11 variant in the sample.

D11 variant is also detected in a sample using confocal single molecule detection (SMD) of fluorescent molecular beacons (MB) as described in *Analyst* 130:483 (2005). This technique utilizes an oligonucleotide with sequences unique to the parvovirus B19 D11 variant described herein. In its native conformation, the molecular beacon forms a hairpin structure where the close proximity of the quencher and fluorophore prevents fluorescence. The hairpin structure will be released upon annealing to the target parvovirus B19 variant oligonucleotide so that the fluorophore is released from the quencher causing fluorescence. This increase in fluorescence is detected by confocal microscopy.

D11 variant is also detected in a sample using a method as described in *Analyst* 131:484 (2006). Such a technique allows for rapid and sensitive detection of parvovirus B19 variant nucleic acids using two-color quantum dots (QDs) and single-molecule coincidence detection. Quantum dots (QDs) have broad excitation spectra with a narrow emission bandwidth and possess exceptional photochemical stability with relatively high quantum yield. According to this method, two biotinylated oligonucleotide probes unique to the D11 variant are used to recognize and detect specific complementary target DNA through a sandwich hybridization reaction. The DNA hybrid is first captured on the surface of one type of QD through specific streptavidin-biotin binding. A different type of QD with a different emission spectrum binds the other end of the DNA hybrid to form a QD/DNA hybrid/QD complex. This hybrid possesses coincident spectra due to the binding of both QDs that is absent when target D11 variant DNA is not present.

Example 5

Differential Detection of Parvovirus B19 D11 Variant-Specific Sequences

The D11 variant described herein is also differentially detected from among other parvovirus B19 such as Au, A6, V9, and D91.1. Samples are prepared as described above and D11 variant nucleic acid is detected using nucleic acid oligonucleotides that specifically target variant sequence but not the other genotypes. Sequence-specific variations among parvovirus B19 genotypes is determined using various alignment algorithms and/or programs known in the art including, but not limited to FASTA, BLAST, or ENTREZ (available through the National Center for Biotechnology Information, National Library of Medicine, National Institutes of Health, Bethesda, Md.). FASTA and BLAST are available as a part of the GCG sequence analysis package (University of Wisconsin, Madison, Wis.).

The targeted nucleic acid can be genomic DNA from intact virions or viral mRNA from parvovirus replicating in cells. Viral DNA or mRNA is prepared as described above and optionally, hybrid capture methods for the selection of specific sequences might be added in tandem to facilitate the enrichment of targeted nucleic acids. Nucleic acid sequences specific to the D11 variant are used as oligonucleotide primers for specific amplification of the variant nucleic acid, as labeled oligonucleotide probes for detection (e.g. incorporation of fluorophores, dyes, or other molecules used for detection), or as selective capture and retention moieties so as to enrich for the target variant while eliminating non-specific nucleic acid sequences.

Nucleic acid amplification and detection are performed as described above. For example, the variant nucleic acids are detected as part of an amplification reaction using labeled oligonucleotide probes (e.g. TaqMan or molecular beacons). Alternatively, variant nucleic acids are differentially amplified using primers specific to the D11 variant described herein and visualized using a variety of methods including, but not limited to gel electrophoresis, micro-well plate systems for detection of amplified nucleic acids, and various fluorogenic methodologies for generating signal as described in *J. Virol Methods* 136:210 (2006) and *J. Clin. Microbiol.* 44:2212 (2006).

Example 6

Identification of Conserved Regions of the Parvovirus B19 DNA Genome

To identify novel target regions of the parvovirus B19 genome that would expand the specificity of B19 detection assays to include detection of parvovirus B19 Genotypes 1, 2, 3, and variants and subtypes within each genotype, in silico analysis was performed to determine highly conserved regions of the parvovirus B19 genome by comparing Genotype 1, 2 and 3 partial and full coding sequences including the novel D11, E3, and P1 variants of the present invention.

A total of seven searches of GenBank (release 159) were performed to identify DNA sequences of parvovirus B19 variants and Genotypes 1, 2, and 3 prototype strains present in the database. These searches were performed using the following terms: 'parvovirus B19', 'Human parvovirus B19', 'Human parvovirus A6', 'Human parvovirus V9', 'Human parvovirus D91.1', 'parvovirus B19 genotype', and 'parvovirus B19 variant'. The identified DNA sequences were imported into the local Vector NTI database and filtered to exclude sequences shorter than 100 bases or longer than 5600 bases, sequences representing human B19 receptor and immunoglobulin genes, circular vectors, parvovirus 4, and parvovirus of other species such as simian and canine. Sequences shorter than 100 bases were omitted since the flanking regions are most likely primer derived and not necessarily actual native parvovirus sequence. Sequences longer than 5600 bases were omitted because the parvovirus B19 genome is only 5600 bases and sequences longer than this includes flanking regions of vector that would alter the consensus sequence. The other omitted sequences are not representative of native parvovirus B19 sequence, and therefore should not be included in the overall consensus calculation. The remaining DNA sequences including the novel D11, E3, and P1 variants of the present invention were aligned using the AlignX program in Vector NTI, v7.1 according to the Alignment Settings in Table 1. These are the default settings in Vector NTI, v.7.1. Pairwise alignment settings dictate the alignment of two individual sequences to each other, while multiple alignment settings dictate how each of the individual pairwise alignments are aligned with all other pairwise alignments.

TABLE 1

Alignment Settings for pairwise alignment (left) and multiple alignment (right) utilized to generate a multiple sequence alignment in Vector NTI, v7.1

| Pairwise Alignment | | Multiple Alignment | |
|---|---|---|---|
| Parameter | Setting | Parameter | Setting |
| Use FAST Algorithm | N/A | Gap Opening Penalty | 15 |
| K-tuple size | N/A | Gap Extension Penalty | 6.66 |
| Number of Best Diagonals | N/A | Gap Separation Penalty Range | 8 |
| Window Size | N/A | No End Gap Separation Penalty | N/A |
| Gap Penalty | N/A | % Identity for Alignment Delay | 40 |
| Gap Opening Penalty | 15 | Residue Specific Gaps Off | N/A |
| Gap Extension Penalty | 6.66 | Hydrophilic Residue Gap Off | N/A |
| | | Transition Weighting | 0 |

Consensus sequences were calculated at 100%, 99%, 98%, 97%, and 95% by Vector NTI according to the following Alignment Display Settings: Consider only identical residues in consensus calculation, Ignore gaps in consensus calculation, and the residue fraction for consensus was set at 1.0, 0.99, 0.98, 0.97, and 0.95 respectively. The function of using a specific sequence as a consensus was left un-checked. Table 2 shows the similarity table used in the consensus calculation. Only strong similarities were considered in consensus calculation.

TABLE 2

Alignment display setup nucleotide similarity table

| Residue | Strong Similarity |
|---------|-------------------|
| A | A |
| C | C |
| G | G |
| T | T |

The consensus sequence calculated at 97% provided the highest degree of sequence homology and minimal nucleotide gaps between the filtered parvovirus sequences. This was the consensus sequence used to design oligonucleotide primer and probe sets for evaluation in real-time PCR detection of parvovirus B19.

Initial identification of primer and probe sets was performed by visual inspection of conserved regions for presence of target regions. A target region was defined as a region in which primers and detection probes could be designed. Target regions were identified that had between 100 and 200 nucleotides and have two flanking sequences (primer binding regions) of 15 to 25 continuous nucleotides with an internal continuous sequence (probe binding region) greater than 20 nucleotides. Also, the internal sequence had to be in close proximity (within 20 nucleotides) to either flanking sequence. The identified primer sequences were further evaluated for primer dimer formation, presence of secondary structure, and melting temperature. Identified detection probes were evaluated to ensure; absence of secondary structure, absence of primer/probe dimers, absence of a 5' guanine residue, and the melting temperature was 7 to 10° C. higher than the flanking primer pair.

The combination of search terms in GenBank identified 881 DNA sequences that were imported into the local Vector NTI database. The 881 imported sequences were filtered according to the criteria stated above and the remaining 565 DNA sequences were aligned using the AlignX program in Vector NTI, v7.1.

A DNA consensus sequence was generated from the alignment of 565 parvovirus B19 DNA sequences utilizing the Alignment Display Settings of Vector NTI shown in Tables 1 and 2. Different DNA consensus sequences were generated with 100%, 99%, 98%, 97%, and 95% homology by changing the 'Residue fraction for consensus' value while retaining all other settings. The 97% consensus sequence was aligned with the Au isolate of B19 (Accession number: M13178) as the reference sequence (FIG. 5) to show the locations of the conserved regions and where no nucleotides are present at the 97% level of sequence homology.

A review of the 97% DNA sequence homology consensus revealed two regions of the parvovirus B19 genome as highly conserved across all of the 565 aligned parvovirus B19 sequences. Relative to parvovirus B19 Genotype 1 prototype strain Au, these two regions encompass nucleotides 1351 to 2426 (FIG. 6) and nucleotides 3704 to 4804 (FIG. 7).

The highly conserved sequence spanning nucleotides 1351 through 2426 was analyzed further to locate any DNA regions that could be utilized as target regions. Four (4) target regions were identified and designated region 1, 2, 4 and 5 (FIG. 8 and Table 3).

TABLE 3

Target Region and oligonucleotide sequences derived from highly conserved regions of the parvovirus B19 genome.

| Target Region | Function | Name | SEQ ID NO: | Sequence (5' to 3') | Tm |
|---|---|---|---|---|---|
| 1 | Forward primer | B19_2043F | 136 | TGAAACCCCGCGCTCTA | 59.6 |
| | Reverse primer | B19_2171R | 137 | AACTAACAGTTCACGAAACTG | 56.7 |
| | Detection probe | B19_2069F_FAM | 138 | TCCCCGGGACCAGTTCAGGAGAA | 68.1 |
| 2 | Forward primer | B19_1962F | 139 | TCAGCAGCAGTGGTGGT | 59.6 |
| | Reverse primer | B19_2043R | 140 | TAGAGCGCGGGGTTTCA | 59.6 |
| | Detection probe | B19_1979F-FAM | 141 | TGAAAGCTCTGAAGAACTCAGTGAAAGCAGCTTT | 67.0 |
| | Forward primer | B19_1903F | 142 | AATGCAGATGCCCTCCAC | 59.9 |
| | Detection probe | B19_1962F-FAM | 143 | TCAGCAGCAGTGGTGGTGAAAGCTCTGAA | 68.9 |
| | Reverse primer | B19_2027R | 144 | TGTTCCAGGCGCCTG | 58.9 |
| 3 | Forward primer | B19_4700F | 145 | CACAGCTACAGATGCAAA | 55.3 |

TABLE 3-continued

Target Region and oligonucleotide sequences derived from highly conserved regions of the parvovirus B19 genome.

| Target Region | Function | Name | SEQ ID NO: | Sequence (5' to 3') | Tm |
|---|---|---|---|---|---|
| | Reverse primer | B19_4769R | 146 | GGTGCACACGGCTTTT | 56.7 |
| | Detection probe | B19_4733R_FAM | 147 | TGTCCACAATTCTTCAGGCTTTTCATATCC | 64.6 |
| | Detection probe | B19_4733F_FAM | 148 | TGGATATGAAAAGCCTGAAGTATTGTGGAC | 64.6 |
| | Forward primer | B19_4672F | 149 | GGTCATTTACCATATGTACT | 54.2 |
| | Detection probe | B19_4703F-FAM | 150 | AGCTACAGATGCAAANCAACACCACAGACA† | 66.7 |
| 4 | Forward primer | B19_1500F | 151 | GAAAACTTTCCATTTAATGATGT | 53.8 |
| | Reverse primer | B19_1631R | 152 | ATTTTTTGATCTACCCTGGT | 54.2 |
| | Detection probe | B19_1537F-FAM | 153 | TTGGTGGTCTGGGATGAAGG | 62.4 |
| 5 | Forward primer | B19_1411F | 154 | GTTTTATGGGCCGCCAAGTA | 60.4 |
| | Reverse primer | B19_1537R | 155 | TTCATCCCAGACCACCAAGG | 62.4 |
| | Detection probe | B19_1450F-FAM | 156 | ATGGCTATTGCTAAAACTGTTCCAGTGTA | 63.2 |
| | Detection probe | B19_1492F-FAM | 157 | TGGAATAATGAAAACTTTCCATTTAATGATGTAG | 61.0 |
| | Detection probe | B19_1448F-FAM | 158 | CAATGGCCATTGCTAAAAGTGTTCCA | 63.0 |

†N = a universal base analogue including, without limitation, 5-nitroindole, inosine, and 4-nitrobenzimidazole.

The highly conserved sequence spanning nucleotides 3704 through 4804 was also analyzed further to locate any potential target regions. One (1) target region was identified and designated as region 3 (FIG. 8 and Table 3).

Figure 9:
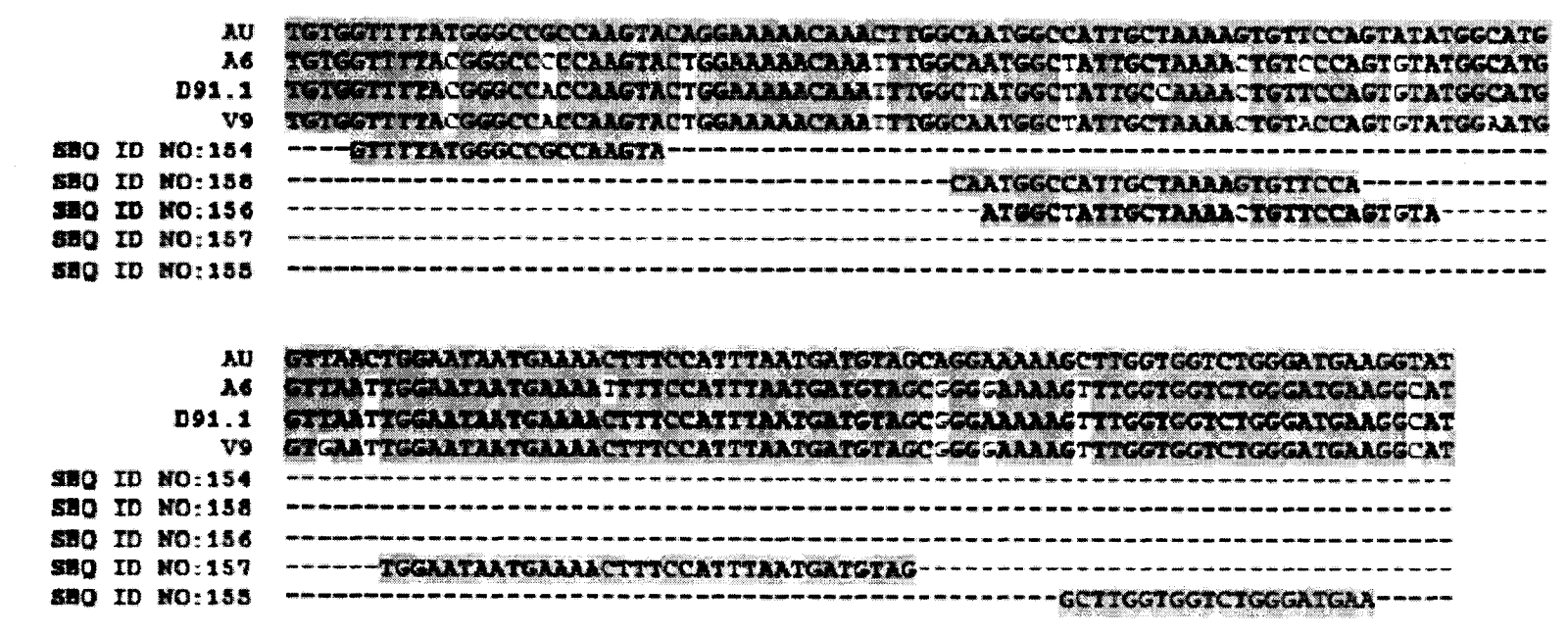

Regions 1, 2, 4 and 5 are positioned within the parvovirus B19 gene coding for non-structural protein 1 (NS 1) and region 3 is positioned within overlapping genes coding for viral protein 1 and 2 (VP1, VP2) (FIG. 8). FIG. 9 shows alignment of e.g., primer/probe sequences of target region 5 to parvovirus B19 Genotype 1 prototype strain Au (i.e., SEQ ID NO:130).

Accordingly, an alignment of 565 parvovirus B19 variant and Genotype 1, 2, and 3 DNA sequences identified five highly conserved target regions of the parvovirus B19 genome at 97% DNA sequence homology. At the 97% DNA sequence homology, 13 oligonucleotide primers in 5 different regions were designed with 100 percent homology to the consensus sequence. At the same level, 10 oligonucleotide detection probes were designed. Of these 10 probes, 6 have a 100 percent homology. At least one probe (i.e., B19_4703-FAM) has 97% homology to the 97% consensus sequence. This probe, B19_4703-FAM, has one base at nucleotide 16 from the 5' end that is blank in the consensus sequence. A universal base (5-nitroindole) was inserted in this position to facilitate hybridization of the probe to the B19 viral DNA sequence. Exemplary universal base analogues include, without limitation, 5-nitroindole, inosine, and 4-nitrobenzimidazole.

Example 7

Evaluating a New Targeting Strategy for Parvovirus B19 Detection

The consensus sequence resulting from alignment of full and partial genomic sequences of human parvovirus B19 Genotypes 1, 2, and 3 present in GenBank was utilized to identify highly conserved regions of the parvovirus B19 genome and design oligonucleotide primers and probes within each conserved region (see Table 3 and FIG. 10). To evaluate experimentally whether the conserved DNA sequence regions identified as potential target regions for parvovirus B19 actually enhance the specificity of detection of parvovirus B19 variants and genotypes, oligonucleotide probes and primers were designed for amplification and detection of the identified regions. A total of 16 primer/probe combination sets were evaluated (Table 4).

TABLE 4

Primer/Probe Combinations for B19 New Targeting Strategy Evaluation.

| Region | Primer/Probe Set | SEQ ID NO: | Oligonucleotide Name | Tm (° C.) |
|---|---|---|---|---|
| 1 | 1 | 136 | B19_2043F | 59.6 |
|   |   | 137 | B19_2171R | 56.7 |
|   |   | 138 | B19_2069F_FAM | 68.1 |
| 2 | 2a | 139 | B19_1962F | 59.6 |
|   |   | 140 | B19_2043R | 59.6 |
|   |   | 141 | B19_1979F-FAM | 67.0 |
|   | 2b | 139 | B19_1962F | 59.6 |
|   |   | 144 | B19_2027R | 58.9 |
|   |   | 141 | B19_1979F-FAM | 67.0 |
|   | 2c | 142 | B19_1903F | 59.9 |
|   |   | 144 | B19_2027R | 58.9 |
|   |   | 141 | B19_1979F-FAM | 67.0 |
|   | 2d | 142 | B19_1903F | 59.9 |
|   |   | 140 | B19_2043R | 59.6 |
|   |   | 141 | B19_1979F-FAM | 67.0 |
|   | 2e | 142 | B19_1903F | 59.9 |
|   |   | 140 | B19_2043R | 59.6 |
|   |   | 143 | B19_1962F-FAM | 68.9 |
|   | 2f | 142 | B19_1903F | 59.9 |
|   |   | 144 | B19_2027R | 58.9 |
|   |   | 143 | B19_1962F-FAM | 68.9 |
| 3 | 3a | 145 | B19_4700F | 55.3 |
|   |   | 146 | B19_4769R | 56.7 |
|   |   | 148 | B19_4733F_FAM | 64.6 |
|   | 3b | 145 | B19_4700F | 55.3 |
|   |   | 146 | B19_4769R | 56.7 |
|   |   | 147 | B19_4733R_FAM | 64.6 |
|   | 3c | 149 | B19_4672F | 54.2 |
|   |   | 146 | B19_4769R | 56.7 |
|   |   | 150 | B19_4703F-FAM | 66.7 |
|   | 3d | 149 | B19_4672F | 54.2 |
|   |   | 146 | B19_4769R | 56.7 |
|   |   | 148 | B19_4733F_FAM | 64.6 |
|   | 3e | 149 | B19_4672F | 54.2 |
|   |   | 146 | B19_4769R | 56.7 |
|   |   | 147 | B19_4733R_FAM | 64.6 |
| 4 | 4 | 151 | B19_1500F | 53.8 |
|   |   | 152 | B19_1631R | 54.2 |
|   |   | 153 | B19_1537F-FAM | 62.4 |
| 5 | 5a | 154 | B19_1411F | 60.4 |
|   |   | 155 | B19_1537R | 62.4 |
|   |   | 156 | B19_1450E-FAM | 63.2 |
|   | 5b | 154 | B19_1411F | 60.4 |
|   |   | 155 | B19_1537R | 62.4 |
|   |   | 157 | B19_1492F-FAM | 61.0 |
|   | 5c | 154 | B19_1411F | 60.4 |
|   |   | 155 | B19_1537R | 62.4 |
|   |   | 158 | B19_1448F-FAM | 63.0 |

All oligonucleotides were purchased from Integrated DNA Technologies (IDT) (Coralville, Iowa) with 100 nmole synthesis scale for primers and 250 nmole scale for probes. Each oligonucleotide was suspended in RNase-, DNase-free water. A B19 master mix was prepared with the oligonucleotide sets (Table 4). The plasma samples utilized for extraction panels are: NAT-056 (Genotype 1), E3 (i.e., SEQ ID NO: 128) (Genotype 1), P1 (i.e., SEQ ID NO: 129) (Genotype 3). Plasma containing parvovirus B19 Genotype 2 is currently not available for assessment. A full-length Genotype 2 amplicon may be obtained for future assessment. Dilution panels of P1 (i.e., SEQ ID NO: 129) and E3 (i.e., SEQ ID NO: 128) were made for initial extraction by 10 fold serial dilutions of the stock material to a $10^{-9}$ final dilution in normal human plasma. The $10^{-4}$, $10^{-7}$, and $10^{-9}$ test sample dilutions were evaluated with the primer and probe combinations in Table 4. Each extraction set included the test samples and controls listed in Table 5.

TABLE 5

Test samples and controls utilized for assessment of primers and probes

| Sample | Dilution | N Size |
|---|---|---|
| B19 Negative Control | NA | 3 |
| B19 Low Positive Control | NA | 3 |
| B19 High Positive Control | NA | 3 |
| B19 100 IU/mL | NA | 2 |
| E3 $1.0 \times 10^{-4}$ | $1:10^4$ | 2 |
| E3 $1.0 \times 10^{-7}$ | $1:10^7$ | 2 |
| E3 $1.0 \times 10^{-9}$ | $1:10^9$ | 2 |
| P1 $1.0 \times 10^{-4}$ | $1:10^4$ | 2 |
| P1 $1.0 \times 10^{-7}$ | $1:10^7$ | 2 |
| P1 $1.0 \times 10^{-9}$ | $1:10^9$ | 2 |

Amplification and detection were performed on the AB7300 Real Time PCR System (Applied Biosystems, Foster City, Calif.). All extracted samples were amplified in duplicate. The amplification controls included five B19 quantification standards for each oligonucleotide set. The assay controls consisted of the B19 Negative Control, B19 Low Positive Control, and B19 High Positive Control. The test master mixes used to amplify the extracted samples were made using the different primer and probe combinations listed in Table 4. Each primer and probe combination was amplified at 2 anneal/extension temperatures: 60° C. and 55° C. to accommodate lower melting temperatures (Tm) of some primers and probes (Table 4).

Results for parvovirus B19 detection for each of the primer and probe combinations at 55° C. and 60° C. for each sample concentration is shown in Table 6.

TABLE 6

Summary of parvovirus B19 amplification and detection for primer/probe sets amplified at 55° C. and 60° C. anneal/extension temperatures.

| Primer/Probe Set | Sample | Temperature 55° C. | 60° C. | Comments |
|---|---|---|---|---|
| 1 | P1 | + | + | Good detection |
|   | E3 | + | + |   |
| 2a | P1 | + | + | Did not detect $10^{-9}$ test sample dilution at 55° C. All test sample dilutions were detected at 60° C. |
|   | E3 | + | + |   |
| 2b | P1 | − | − | Primer/probe failure likely due to proximity of primer to probe proximity |
|   | E3 | − | − |   |
| 2c | P1 | − | − | Reverse primer B19_2027R unable to amplify and detect target |
|   | E3 | − | − |   |

TABLE 6-continued

Summary of parvovirus B19 amplification and detection for primer/probe sets amplified at 55° C. and 60° C. anneal/extension temperatures.

| Primer/Probe Set | Sample | Temperature 55° C. | 60° C. | Comments |
|---|---|---|---|---|
| 2d | P1 | + | + | Good detection, especially at 60° C. |
|  | E3 | + | + |  |
| 2e | P1 | + | + | Good detection at 60° C. |
|  | E3 | + | + | Did not detect all $10^{-9}$ test sample dilutions |
| 2f | P1 | − | − | Not analyzed since reverse primer shared |
|  | E3 | − | − | with Primer/probe Set 2c |
| 3a | P1 | + | + | At 60° C., only $10^{-4}$ test sample dilution amplified and detected |
|  | E3 | + | + | Good detection at 55° C. |
| 3b | P1 | + | + | Good detection |
|  | E3 | + | + |  |
| 3c | P1 | + | + | Good detection at 55° C. |
|  | E3 | + | + | At 60° C., only $10^{-4}$ test sample dilution amplified and detected |
| 3d | P1 | + | + | No robust amplification and detection at low test sample concentrations |
|  | E3 | + | + |  |
| 3e | P1 | + | + | No robust amplification and detection at low test sample concentrations |
|  | E3 | + | + |  |
| 4 | P1 | + | − | Poor detection at 55° C. |
|  | E3 | + | − | No detection at 60° C. |
| 5a | P1 | + | − |  |
|  | E3 | + | − |  |
| 5b | P1 | + | + | Good detection |
|  | E3 | + | + | Good detection |
| 5c | P1 | − | − |  |
|  | E3 | + | + | Good detection |

Key:
(+) indicates detection and
(−) indicates no detection.

Figure 11:
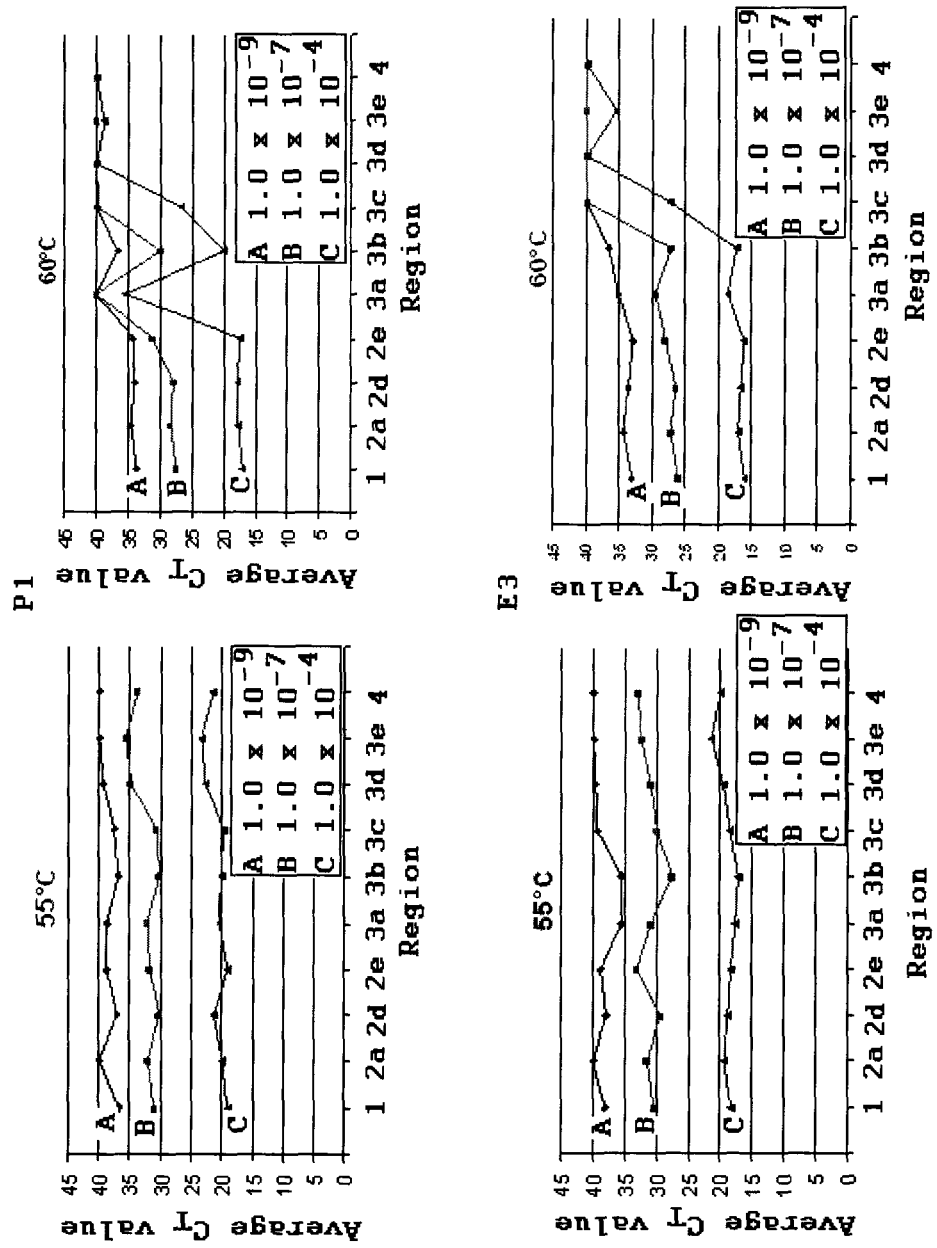
FIG. 11 shows average $C_T$ values for P1 (i.e., SEQ ID NO: 129) and E3 (i.e., SEQ ID NO: 128) across target regions 1 through 4. Test sample dilutions that showed no amplification and detection are plotted as $C_T=40$.
Figure 12:
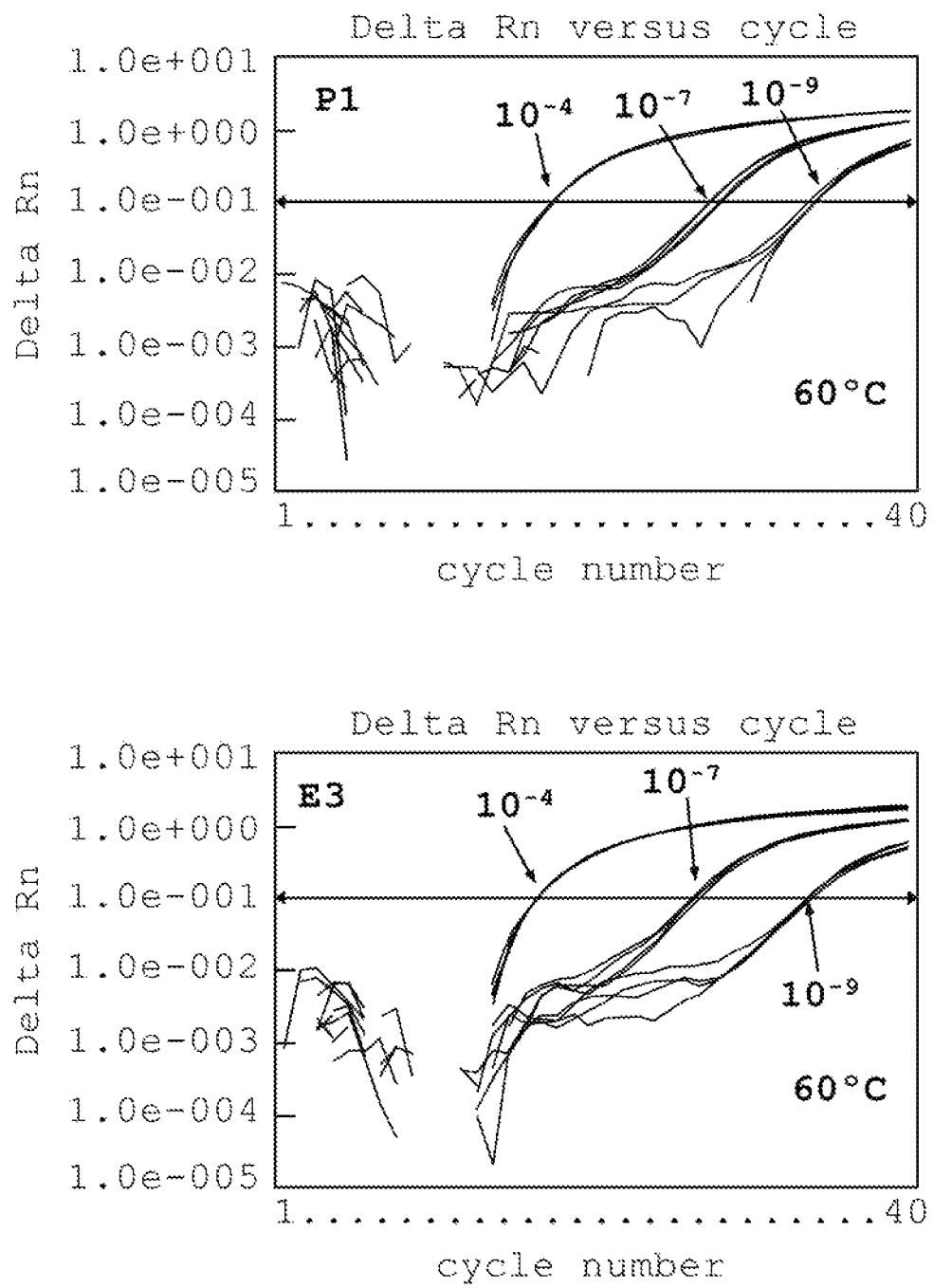
FIG. 12 shows amplification plots for Primer/probe Set 2d at 60° C.: P1 (i.e., SEQ ID NO: 129) and E3 (i.e., SEQ ID NO: 128).
Figure 13:
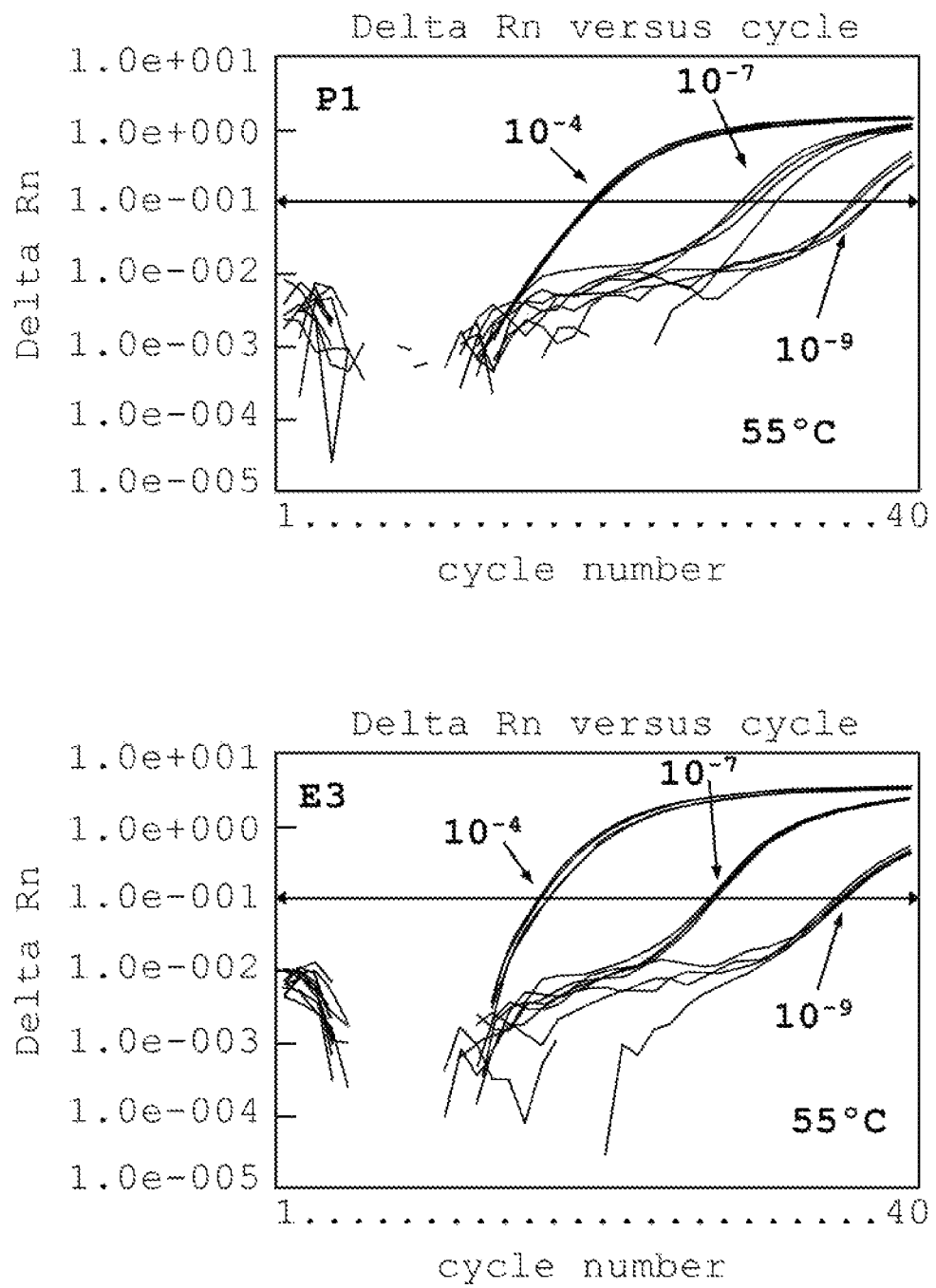
FIG. 13 shows amplification plots for Primer/probe Set 3b at 55° C.: P1 (i.e., SEQ ID NO: 129) and E3 (i.e., SEQ ID NO: 128).

Thirteen out of 16 primer/probe sets representing all 5 conserved regions showed detection of P1 (i.e., SEQ ID NO: 129) and/or E3 (i.e., SEQ ID NO: 128). Primer/probe Set 2b did not demonstrate amplification and detection. Further oligonucleotide and B19 genomic region sequence analysis proved that the probe and forward primer were positioned too close to each other (probe overlapping the 3' end of the primer) to generate amplification and detection. Primer/probe Set 2c also did not demonstrate amplification and detection, most likely due to poor design/performance of the reverse primer. Primer/probe Set 2f was not analyzed because it shared the same reverse primer with Primer/probe Set 2c. The average $C_T$ values from the amplification and detection of P1 (i.e., SEQ ID NO: 129) and E3 (i.e., SEQ ID NO: 128) at both anneal/extension temperatures for 10 of the 12 primer/probe sets are shown in FIG. 11. Examples of amplification plots are shown for Primer/probe Sets 2d and 3b in FIGS. 12 and 13.

All 5 target regions that were identified as conserved regions of the parvovirus B19 genome showed detection of both P1 and E3 variants, confirming that these target regions were conserved at least for parvovirus B19 genotypes 1 and 3. Primer/probe sets designed to detect the 5 target regions provided good robust amplification and detection.

What is claimed is:

1. A method for detecting a parvovirus B19 nucleic acid in a sample, the method comprising:
   a) performing PCR with at least a portion of the sample using a forward primer, the nucleotide sequence of which consists of SEQ ID NO:145, and a reverse primer, the nucleotide sequence of which consists of SEQ ID NO:146; and
   b) determining the presence or absence of an amplicon, wherein the presence of the amplicon is indicative of the presence of the parvovirus B19 nucleic acid in the sample, wherein determining comprises annealing an oligonucleotide to the amplicon.

2. The method of claim 1, wherein the oligonucleotide comprises the sequence set forth in:
   (SEQ ID NO:147) or the sequence fully complementary thereto.

3. The method of claim 1, wherein the presence of the amplicon indicates the presence of a parvovirus B19 genotype 1 or 3 if present in the sample.

* * * * *

```
                    SEQUENCE LISTING

<160> NUMBER OF SEQ ID NOS: 158

<210> SEQ ID NO 1
<211> LENGTH: 4778
<212> TYPE: DNA
<213> ORGANISM: Erythrovirus B19

<400> SEQUENCE: 1
cagctctttc ttttggggtt gcttttacct ggacttttct tgctgtctttt tgcgtgctaa      60 ctaacaggta tttatactac ttgttaactt actaacatgg agttatttag aggggtgatt     120
caagtttctt ctaacattct tgactgtgct aacgataact ggtggtgctc tatgctggat     180
ttagacactt ctgactggga accattaact cattctaaca gactaatggc aatatattta     240
agcagcgtgg cttctaagct tgactttaca ggggggccct tagctgggtg cttgtactt      300
```

```
tttcaggtgg aatgtaacaa atttgaggaa ggctatcata tccatgtggt tattgggga      360 ccagggctaa accctagaaa cctaacagtg tgtgtagagg gattatttaa taatgtactt     420
taccaccttg taactgaaaa tgtaaagctt aaattttac caggaatgac tacaaaaggc     480
aaatatttta gagatggaga acaatttata gaaaattatt taatgaaaaa atacccttta    540
aatgttgtat ggtgtgtaac caatattgat gggtacatag atacctgcat ttctgcttct   600
tttagacggg gagcctttca ggctaaaaaa ccccgcatta gtgcaaacac tgatgggggt   660
tctaatgaac caggggaatc tagcgctaca ggggagatg ttgtgccatt tgctgggaag    720
gggactaaag ctggaataaa atttcaaact atggtaaatt ggttgtgtga aataggggtt   780
tttacagagg ataagtggaa actagttgac tttaaccagt acactttact tagcagtagt   840
cacagtggga gctttcaaat acaaagtgca ttaaaactag ctatttataa ggctaccaat   900
ttagtgccta caagtacatt tttgttacac acagactttg agcaggctaa ctgtattaaa    960
gaaaataaaa tagttaaact gttactgtgt caaaattatg acccccttgtt ggtgggacag   1020 catgtgttaa agtggattga taaaaaatgt ggcaaaaaaa atacactgtg gttttatggc    1080
ccaccaagta caggaaaaac aaatttagca atggctattg ctaaaactgt tccagtgtat    1140
ggtatggtta attggaataa tgaaaatttt ccatttaatg atgtagcagg aaaaagcttg    1200
gtggtctggg atgagggtat tattaagtct actattgtag aagctgcaaa agccatttta   1260
ggagggcaac caaccagggt agatcaaaaa atgcgtggaa gtgtagcagt gcctggagta   1320
ccagtggtaa taaccagcaa tggtgacatt acttttgttg ttagtgggaa cactacaaca   1380
actgtccatg ctaaagcctt aaaggagcga atggtaaagt taaactttac cataagatgt   1440
agccctgaca tgggcttact tacagaggct gacgtgcagc aatggcttac atggtgtaat   1500
gcacaaagct ggagccacta tgaaaactgg gcaataaact acactttga tttccctgga   1560 ataaatgcag atgccctcca cccagacctc caaaccaccc caattgtcac agacaccagt   1620
gtcagcagca gtggtggtga aagctctgaa gaactcagtg aaagcagctt tctcaacctc   1680 atcacccag gcgcctggaa cactgaaacc ccgcgctcta gtacgccagt ccccgggacc    1740
agttcaggag aatcatttgt cggaagctca atttcctccg aagctgtagc tgcatcgtgg   1800
gaagaagcct tctacacacc tttggcagat cagtttcgtg aactgttagt tggggttgac   1860
tatgtatggg atggtataag ggggtttacct gtttgttgtg tgcaacatat taataacagt   1920
gggggaggct tgggattttg tccccattgc attaatgtgg gggcttggta taatggatgg   1980
aagtttcgag aatttacccc agatttggtg cggtgtagct gtcatgtagg agcttctaat   2040
cctttttctg tgttaacctg caaaaaatgt gcttacctat ctggcttgca aagttttgta    2100
gattatgagt aaagaaattg gtaaatggtg ggaaagtgat gataaatttg ctaaggacgt   2160
gtataagcaa tttgtagaat tttatgaaaa agttactgga acagacttag agcttattca   2220
aatattaaaa gatcattaca atatttcttt agataatcct ctagaaaacc catcttcttt    2280
gtttgactta gtggctcgta ttaaaagtaa ccttaaaaac tctccagact tatatagtca   2340
tcattttcaa agtcatggac agttatctga ccacccccat gccttatcat ccagtaacag   2400
tgatgcagaa cctagaggag aaaatgcagt attatctagt gaagacttac acaagcctgg   2460
gcaagttagc atacaactac ccggtactaa ctatgttggg cctggcaatg agctacaagc   2520
tgggcccccg cagagtgctg tggacagtgc tgcaaggatt catgacttta ggtatagcca   2580
actggctaag ctgggaataa atccatatac tcattggact gtagcagatg aggagctgtt    2640
aaaaaatata aaaaatgaaa ctgggttca agctcaagta gtaaaagact actttacttt    2700
```

```
aaaaggtgca gctgcccctg tggcccattt tcaaggaagt ttgccggaag ttcccgctta    2760
caacgcctca gaaaaatacc caagcatgac ttcagttaat tctgcagaag ccagcactgg    2820
tgcaggaggg ggcggcagta atcctactaa aagcatgtgg agtgaggggg ctacttttac    2880
tgccaactct gtaacttgta cattttccag acagttttta atcccatatg atccagagca    2940
ccattataaa gtgttttctc ccgcagccag tagctgccac aatgccagtg aaaagaggc     3000 aaaagtttgc accattagtc ccataatggg atactccaca ccatggagat acttagattt    3060
taatgcttta aatttatttt tttcacccttt agagtttcaa catttaattg agaattatgg    3120
aagtatagct cctgatgctt taactgttgc catatcagaa attgccatta aagatgttac    3180
agacaaaact ggaggagggg tacaggttac tgacagtact acagggcgtt tatgcatgtt    3240
agtagaccat gaatacaagt acccatatgt attaggtcaa ggacaagata ccttagcccc    3300
agagcttcca atttgggtgt actttccacc tcaatatgct tacttaacag taggagatgt    3360
aaacacgcag ggaatttctg gggacagtaa aaaattagct agtgaagaat cagcgtttta    3420
tgtcctggaa cacagctctt ttgaactttt aggtacaggg ggctctgcta ctatgtctta    3480
taagttccct ccagtgcccc cagagaattt agaaggctgt agtcaacact tttatgaaat    3540
gtacaacccg ttatatggat cccgtttagg agtccctgat acattaggag gggaccccaa    3600
atttagatct ttaacacatg aagaccacgc agttcagcca caaaatttta tgccagggcc    3660
actggtaaac tcagtttcca caaggagggg agacagttct aacacaggag cgggaaaagc    3720
cctaacaggc cttagcacag gcactagtca aagtactaga atatcattac gccctggtcc    3780
agtgtctcaa ccatatcacc actgggacac agataaaatat gtaacaggga taaatgccat    3840
ttctcatggt caaaccactt atggcaatgc tgaagacaaa gagtatcaac agggcgtggg    3900
taggtttccc aatgaaaaag aacaactaaa acagttacag ggtttaaata tacacacata    3960
ttttcccaat aaaggtaccc agcaatatac agatcaaatt gagcgcccccc taatggtagg    4020 ctctgtatgg aacagaagag cccttcacta tgaaagccag ctgtggagta aaataccaaa    4080
tttagatgac agctttaaaa ctcagtttgc agctttagga ggttgggggac tacatcagcc    4140 accccctcaa atatttttaa aaatattacc acaaagtggg ccaattgggg gtattaagtc    4200
aatgggaata acaacattag ttcaatatgc tgtgggtatt atgacagtaa ctatgacatt    4260
taaattaggg cctcgcaaag ctacaggacg gtggaatcct caacctggag tgtaccctcc    4320
tcacgcagca ggccatttac catatgtact atatgacccc acagctacag atgcaaagca    4380
acaccacaga catggatatg aaaagcctga agaattgtgg actgccaaaa gccgtgtgca    4440
cccattgtaa acactcccca ccgtgccctc agccaggatg tgtaactaaa cgcccaccag    4500
tgccacctag actgtattta ccccccctg tacctataag acagcctacc acaaaagaca    4560
cagacaatgt agagtttaaa tacttaagcc gctatgaaca acatgtaatt agaatgttaa    4620
gattgtgtaa tatgtataaa aatttagaaa aataaacact tgttgcagtt aataaattgc    4680
gtatgttgtg tttttaaaaat ttaaaagaag acaccaaatc agatgccgcc ggtcgccgcc    4740
ggtaggcggg acttccggta caagatggcg gaaattca                           4778
```

<210> SEQ ID NO 2
<211> LENGTH: 18
<212> TYPE: DNA
<213> ORGANISM: Erythrovirus B19

<400> SEQUENCE: 2
gataactggt ggtgctct                                                  18

<210> SEQ ID NO 3
<211> LENGTH: 14
<212> TYPE: DNA
<213> ORGANISM: Erythrovirus B19

<400> SEQUENCE: 3
acttctgact ggga                                                      14

<210> SEQ ID NO 4
<211> LENGTH: 17
<212> TYPE: DNA
<213> ORGANISM: Erythrovirus B19

<400> SEQUENCE: 4
gaatgtaaca aatttga                                                   17

<210> SEQ ID NO 5
<211> LENGTH: 14
<212> TYPE: DNA
<213> ORGANISM: Erythrovirus B19

<400> SEQUENCE: 5
ttatttaata atgt                                                      14

<210> SEQ ID NO 6
<211> LENGTH: 13
<212> TYPE: DNA
<213> ORGANISM: Erythrovirus B19

<400> SEQUENCE: 6
cttgtaactg aaa                                                       13

<210> SEQ ID NO 7
<211> LENGTH: 14
<212> TYPE: DNA
<213> ORGANISM: Erythrovirus B19

<400> SEQUENCE: 7
tttagagatg gaga                                                      14

<210> SEQ ID NO 8
<211> LENGTH: 14
<212> TYPE: DNA
<213> ORGANISM: Erythrovirus B19

<400> SEQUENCE: 8
ttaatgaaaa aaat                                                      14

<210> SEQ ID NO 9
<211> LENGTH: 14
<212> TYPE: DNA
<213> ORGANISM: Erythrovirus B19

<400> SEQUENCE: 9
cctttaaatg ttgt                                                      14

<210> SEQ ID NO 10
<211> LENGTH: 15
<212> TYPE: DNA
<213> ORGANISM: Erythrovirus B19

<400> SEQUENCE: 10

-continued

```
cagactttga gcagg                                              15

<210> SEQ ID NO 11
<211> LENGTH: 14
<212> TYPE: DNA
<213> ORGANISM: Erythrovirus B19

<400> SEQUENCE: 11
tggaataatg aaaa                                               14

<210> SEQ ID NO 12
<211> LENGTH: 20
<212> TYPE: DNA
<213> ORGANISM: Erythrovirus B19

<400> SEQUENCE: 12
tttccattta atgatgtagc                                         20

<210> SEQ ID NO 13
<211> LENGTH: 17
<212> TYPE: DNA
<213> ORGANISM: Erythrovirus B19

<400> SEQUENCE: 13
ttggtggtct gggatga                                            17

<210> SEQ ID NO 14
<211> LENGTH: 23
<212> TYPE: DNA
<213> ORGANISM: Erythrovirus B19

<400> SEQUENCE: 14
gaagctgcaa aagccatttt agg                                     23

<210> SEQ ID NO 15
<211> LENGTH: 14
<212> TYPE: DNA
<213> ORGANISM: Erythrovirus B19

<400> SEQUENCE: 15
accagggtag atca                                               14

<210> SEQ ID NO 16
<211> LENGTH: 23
<212> TYPE: DNA
<213> ORGANISM: Erythrovirus B19

<400> SEQUENCE: 16
ataaccagca atggtgacat tac                                     23

<210> SEQ ID NO 17
<211> LENGTH: 17
<212> TYPE: DNA
<213> ORGANISM: Erythrovirus B19

<400> SEQUENCE: 17
catgctaaag ccttaaa                                            17

<210> SEQ ID NO 18
<211> LENGTH: 14
<212> TYPE: DNA
<213> ORGANISM: Erythrovirus B19
```

```
<400> SEQUENCE: 18
agccctgaca tggg                                                  14

<210> SEQ ID NO 19
<211> LENGTH: 21
<212> TYPE: DNA
<213> ORGANISM: Erythrovirus B19

<400> SEQUENCE: 19
tggtgtaatg cacaaagctg g                                          21

<210> SEQ ID NO 20
<211> LENGTH: 30
<212> TYPE: DNA
<213> ORGANISM: Erythrovirus B19

<400> SEQUENCE: 20
ccactatgaa aactgggcaa taaactacac                                 30

<210> SEQ ID NO 21
<211> LENGTH: 17
<212> TYPE: DNA
<213> ORGANISM: Erythrovirus B19

<400> SEQUENCE: 21
tttgatttcc ctggaat                                               17

<210> SEQ ID NO 22
<211> LENGTH: 23
<212> TYPE: DNA
<213> ORGANISM: Erythrovirus B19

<400> SEQUENCE: 22
aatgcagatg ccctccaccc aga                                        23

<210> SEQ ID NO 23
<211> LENGTH: 14
<212> TYPE: DNA
<213> ORGANISM: Erythrovirus B19

<400> SEQUENCE: 23
ctccaaacca cccc                                                  14

<210> SEQ ID NO 24
<211> LENGTH: 35
<212> TYPE: DNA
<213> ORGANISM: Erythrovirus B19

<400> SEQUENCE: 24
tcagcagcag tggtggtgaa agctctgaag aactc                           35

<210> SEQ ID NO 25
<211> LENGTH: 16
<212> TYPE: DNA
<213> ORGANISM: Erythrovirus B19

<400> SEQUENCE: 25
ccaggcgcct ggaaca                                                16

<210> SEQ ID NO 26
<211> LENGTH: 24
<212> TYPE: DNA
<213> ORGANISM: Erythrovirus B19
```

```
<400> SEQUENCE: 26 tgaaacccccg cgctctagta cgcc                                        24

<210> SEQ ID NO 27
<211> LENGTH: 38
<212> TYPE: DNA
<213> ORGANISM: Erythrovirus B19

<400> SEQUENCE: 27
tccccgggac cagttcagga gaatcatttg tcggaagc                          38

<210> SEQ ID NO 28
<211> LENGTH: 20
<212> TYPE: DNA
<213> ORGANISM: Erythrovirus B19

<400> SEQUENCE: 28
cagtttcgtg aactgttagt                                              20

<210> SEQ ID NO 29
<211> LENGTH: 20
<212> TYPE: DNA
<213> ORGANISM: Erythrovirus B19

<400> SEQUENCE: 29
gcttggtata atggatggaa                                              20

<210> SEQ ID NO 30
<211> LENGTH: 14
<212> TYPE: DNA
<213> ORGANISM: Erythrovirus B19

<400> SEQUENCE: 30
aaatgtgctt acct                                                    14

<210> SEQ ID NO 31
<211> LENGTH: 19
<212> TYPE: DNA
<213> ORGANISM: Erythrovirus B19

<400> SEQUENCE: 31
tttgtagatt atgagtaaa                                               19

<210> SEQ ID NO 32
<211> LENGTH: 17
<212> TYPE: DNA
<213> ORGANISM: Erythrovirus B19

<400> SEQUENCE: 32
atttctttag ataatcc                                                 17

<210> SEQ ID NO 33
<211> LENGTH: 19
<212> TYPE: DNA
<213> ORGANISM: Erythrovirus B19

<400> SEQUENCE: 33
tatatagtca tcattttca                                               19

<210> SEQ ID NO 34
<211> LENGTH: 43
<212> TYPE: DNA
```

<213> ORGANISM: Erythrovirus B19

<400> SEQUENCE: 34
catggacagt tatctgacca cccccatgcc ttatcatcca gta        43

<210> SEQ ID NO 35
<211> LENGTH: 33
<212> TYPE: DNA
<213> ORGANISM: Erythrovirus B19

<400> SEQUENCE: 35
cagaacctag aggagaaaat gcagtattat cta        33

<210> SEQ ID NO 36
<211> LENGTH: 31
<212> TYPE: DNA
<213> ORGANISM: Erythrovirus B19

<400> SEQUENCE: 36
tgaagactta cacaagcctg ggcaagttag c        31

<210> SEQ ID NO 37
<211> LENGTH: 35
<212> TYPE: DNA
<213> ORGANISM: Erythrovirus B19

<400> SEQUENCE: 37
tacccggtac taactatgtt gggcctggca atgag        35

<210> SEQ ID NO 38
<211> LENGTH: 13
<212> TYPE: DNA
<213> ORGANISM: Erythrovirus B19

<400> SEQUENCE: 38
tacaagctgg gcc        13

<210> SEQ ID NO 39
<211> LENGTH: 39
<212> TYPE: DNA
<213> ORGANISM: Erythrovirus B19

<400> SEQUENCE: 39
gacagtgctg caaggattca tgactttagg tatagccaa        39

<210> SEQ ID NO 40
<211> LENGTH: 23
<212> TYPE: DNA
<213> ORGANISM: Erythrovirus B19

<400> SEQUENCE: 40
ttaaaaaata taaaaaatga aac        23

<210> SEQ ID NO 41
<211> LENGTH: 53
<212> TYPE: DNA
<213> ORGANISM: Erythrovirus B19

<400> SEQUENCE: 41
tactttactt taaaaggtgc agctgccct gtggcccatt ttcaaggaag ttt        53

<210> SEQ ID NO 42
<211> LENGTH: 23

```
<212> TYPE: DNA
<213> ORGANISM: Erythrovirus B19

<400> SEQUENCE: 42
tacaacgcct cagaaaaata ccc                                          23

<210> SEQ ID NO 43
<211> LENGTH: 17
<212> TYPE: DNA
<213> ORGANISM: Erythrovirus B19

<400> SEQUENCE: 43
agcatgactt cagttaa                                                 17

<210> SEQ ID NO 44
<211> LENGTH: 26
<212> TYPE: DNA
<213> ORGANISM: Erythrovirus B19

<400> SEQUENCE: 44
tctgcagaag ccagcactgg tgcagg                                       26

<210> SEQ ID NO 45
<211> LENGTH: 17
<212> TYPE: DNA
<213> ORGANISM: Erythrovirus B19

<400> SEQUENCE: 45
aaaagcatgt ggagtga                                                 17

<210> SEQ ID NO 46
<211> LENGTH: 17
<212> TYPE: DNA
<213> ORGANISM: Erythrovirus B19

<400> SEQUENCE: 46
agtagctgcc acaatgc                                                 17

<210> SEQ ID NO 47
<211> LENGTH: 17
<212> TYPE: DNA
<213> ORGANISM: Erythrovirus B19

<400> SEQUENCE: 47
ttagatttta atgcttt                                                 17

<210> SEQ ID NO 48
<211> LENGTH: 14
<212> TYPE: DNA
<213> ORGANISM: Erythrovirus B19

<400> SEQUENCE: 48
gatgctttaa ctgt                                                    14

<210> SEQ ID NO 49
<211> LENGTH: 20
<212> TYPE: DNA
<213> ORGANISM: Erythrovirus B19

<400> SEQUENCE: 49
tatgcttact taacagtagg                                              20

<210> SEQ ID NO 50
```

-continued

```
<210> SEQ ID NO 50
<211> LENGTH: 14
<212> TYPE: DNA
<213> ORGANISM: Erythrovirus B19

<400> SEQUENCE: 50
agtgaagaat cagc                                                       14

<210> SEQ ID NO 51
<211> LENGTH: 17
<212> TYPE: DNA
<213> ORGANISM: Erythrovirus B19

<400> SEQUENCE: 51
ttttatgaaa tgtacaa                                                    17

<210> SEQ ID NO 52
<211> LENGTH: 20
<212> TYPE: DNA
<213> ORGANISM: Erythrovirus B19

<400> SEQUENCE: 52
gctgaagaca aagagtatca                                                 20

<210> SEQ ID NO 53
<211> LENGTH: 14
<212> TYPE: DNA
<213> ORGANISM: Erythrovirus B19

<400> SEQUENCE: 53
aatgaaaaag aaca                                                       14

<210> SEQ ID NO 54
<211> LENGTH: 14
<212> TYPE: DNA
<213> ORGANISM: Erythrovirus B19

<400> SEQUENCE: 54
tggaacagaa gagc                                                       14

<210> SEQ ID NO 55
<211> LENGTH: 14
<212> TYPE: DNA
<213> ORGANISM: Erythrovirus B19

<400> SEQUENCE: 55
cttcactatg aaag                                                       14

<210> SEQ ID NO 56
<211> LENGTH: 21
<212> TYPE: DNA
<213> ORGANISM: Erythrovirus B19

<400> SEQUENCE: 56
cctcaaatat ttttaaaaat a                                               21

<210> SEQ ID NO 57
<211> LENGTH: 21
<212> TYPE: DNA
<213> ORGANISM: Erythrovirus B19

<400> SEQUENCE: 57
cctcaaatat ttttaaaaat a                                               21
```

```
<210> SEQ ID NO 58
<211> LENGTH: 17
<212> TYPE: DNA
<213> ORGANISM: Erythrovirus B19

<400> SEQUENCE: 58
catttaccat atgtact                                                    17

<210> SEQ ID NO 59
<211> LENGTH: 26
<212> TYPE: DNA
<213> ORGANISM: Erythrovirus B19

<400> SEQUENCE: 59
tatgacccca cagctacaga tgcaaa                                          26

<210> SEQ ID NO 60
<211> LENGTH: 29
<212> TYPE: DNA
<213> ORGANISM: Erythrovirus B19

<400> SEQUENCE: 60
ggatatgaaa agcctgaaga attgtggac                                       29

<210> SEQ ID NO 61
<211> LENGTH: 39
<212> TYPE: DNA
<213> ORGANISM: Erythrovirus B19

<400> SEQUENCE: 61
cacttctgac tgggaaccat taactcattc taacagact                            39

<210> SEQ ID NO 62
<211> LENGTH: 39
<212> TYPE: DNA
<213> ORGANISM: Erythrovirus B19

<400> SEQUENCE: 62
atgtaaagct taaatttta ccaggaatga ctacaaaag                             39

<210> SEQ ID NO 63
<211> LENGTH: 39
<212> TYPE: DNA
<213> ORGANISM: Erythrovirus B19

<400> SEQUENCE: 63
aatattttag agatggagaa caatttatag aaaattatt                            39

<210> SEQ ID NO 64
<211> LENGTH: 39
<212> TYPE: DNA
<213> ORGANISM: Erythrovirus B19

<400> SEQUENCE: 64
attttagaga tggagaacaa tttatagaaa attatttaa                            39

<210> SEQ ID NO 65
<211> LENGTH: 39
<212> TYPE: DNA
<213> ORGANISM: Erythrovirus B19

<400> SEQUENCE: 65
taaccaatat tgatgggtac atagataact gcatttctg                            39
```

<210> SEQ ID NO 66
<211> LENGTH: 39
<212> TYPE: DNA
<213> ORGANISM: Erythrovirus B19

<400> SEQUENCE: 66
atgggtacat agatacctgc atttctgctt cttttagac                              39

<210> SEQ ID NO 67
<211> LENGTH: 39
<212> TYPE: DNA
<213> ORGANISM: Erythrovirus B19

<400> SEQUENCE: 67
ttagacgggg agcctttcag gctaaaaaac cccgcatta                              39

<210> SEQ ID NO 68
<211> LENGTH: 39
<212> TYPE: DNA
<213> ORGANISM: Erythrovirus B19

<400> SEQUENCE: 68
gaaccagggg aatctagcgc tacaggggga gatgttgtg                              39

<210> SEQ ID NO 69
<211> LENGTH: 39
<212> TYPE: DNA
<213> ORGANISM: Erythrovirus B19

<400> SEQUENCE: 69
tgccatttgc tgggaagggg actaaagctg gaataaaat                              39

<210> SEQ ID NO 70
<211> LENGTH: 39
<212> TYPE: DNA
<213> ORGANISM: Erythrovirus B19

<400> SEQUENCE: 70
ggactaaagc tggaataaaa tttcaaacta tggtaaatt                              39

<210> SEQ ID NO 71
<211> LENGTH: 39
<212> TYPE: DNA
<213> ORGANISM: Erythrovirus B19

<400> SEQUENCE: 71
taaattggtt gtgtgaaaat agggtttttta cagaggata                             39

<210> SEQ ID NO 72
<211> LENGTH: 39
<212> TYPE: DNA
<213> ORGANISM: Erythrovirus B19

<400> SEQUENCE: 72
attggttgtg tgaaaatagg gttttttacag aggataagt                             39

<210> SEQ ID NO 73
<211> LENGTH: 39
<212> TYPE: DNA
<213> ORGANISM: Erythrovirus B19

<400> SEQUENCE: 73
ttaaccagta cactttactt agcagtagtc acagtggga                              39

<210> SEQ ID NO 74
<211> LENGTH: 39
<212> TYPE: DNA
<213> ORGANISM: Erythrovirus B19

<400> SEQUENCE: 74
taaaactagc tatttataag gctaccaatt tagtgccta                              39

<210> SEQ ID NO 75
<211> LENGTH: 39
<212> TYPE: DNA
<213> ORGANISM: Erythrovirus B19

<400> SEQUENCE: 75
tagctattta taaggctacc aatttagtgc ctacaagta                              39

<210> SEQ ID NO 76
<211> LENGTH: 39
<212> TYPE: DNA
<213> ORGANISM: Erythrovirus B19

<400> SEQUENCE: 76
ctaccaattt agtgcctaca agtacatttt tgttacaca                              39

<210> SEQ ID NO 77
<211> LENGTH: 39
<212> TYPE: DNA
<213> ORGANISM: Erythrovirus B19

<400> SEQUENCE: 77
caagtacatt tttgttacac acagactttg agcaggcta                              39

<210> SEQ ID NO 78
<211> LENGTH: 39
<212> TYPE: DNA
<213> ORGANISM: Erythrovirus B19

<400> SEQUENCE: 78
cacacagact tgagcaggc taactgtatt aaagaaaat                               39

<210> SEQ ID NO 79
<211> LENGTH: 39
<212> TYPE: DNA
<213> ORGANISM: Erythrovirus B19

<400> SEQUENCE: 79
gtgtcaaaat tatgaccect tgttggtggg acagcatgt                              39

<210> SEQ ID NO 80
<211> LENGTH: 39
<212> TYPE: DNA
<213> ORGANISM: Erythrovirus B19

<400> SEQUENCE: 80
ggattgataa aaaatgtggc aaaaaaaata cactgtggt                              39

<210> SEQ ID NO 81
<211> LENGTH: 39
<212> TYPE: DNA
<213> ORGANISM: Erythrovirus B19

<400> SEQUENCE: 81
atacactgtg gttttatggc ccaccaagta caggaaaaa         39

<210> SEQ ID NO 82
<211> LENGTH: 39
<212> TYPE: DNA
<213> ORGANISM: Erythrovirus B19

<400> SEQUENCE: 82
gtacaggaaa aacaaattta gcaatggcta ttgctaaaa         39

<210> SEQ ID NO 83
<211> LENGTH: 39
<212> TYPE: DNA
<213> ORGANISM: Erythrovirus B19

<400> SEQUENCE: 83
gcttggtggt ctgggatgag ggtattatta agtctacta         39

<210> SEQ ID NO 84
<211> LENGTH: 39
<212> TYPE: DNA
<213> ORGANISM: Erythrovirus B19

<400> SEQUENCE: 84
gcttacttac agaggctgac gtgcagcaat ggcttacat         39

<210> SEQ ID NO 85
<211> LENGTH: 39
<212> TYPE: DNA
<213> ORGANISM: Erythrovirus B19

<400> SEQUENCE: 85
ccccgcgctc tagtacgcca gtccccggga ccagttcag         39

<210> SEQ ID NO 86
<211> LENGTH: 39
<212> TYPE: DNA
<213> ORGANISM: Erythrovirus B19

<400> SEQUENCE: 86
agaatcattt gtcggaagct caatttcctc cgaagctgt         39

<210> SEQ ID NO 87
<211> LENGTH: 39
<212> TYPE: DNA
<213> ORGANISM: Erythrovirus B19

<400> SEQUENCE: 87
atcatttgtc ggaagctcaa tttcctccga agctgtagc         39

<210> SEQ ID NO 88
<211> LENGTH: 39
<212> TYPE: DNA
<213> ORGANISM: Erythrovirus B19

<400> SEQUENCE: 88
agctcaattt cctccgaagc tgtagctgca tcgtgggaa         39

<210> SEQ ID NO 89
<211> LENGTH: 39
<212> TYPE: DNA
<213> ORGANISM: Erythrovirus B19

<400> SEQUENCE: 89

```
tgactatgta tgggatggta taagggttt acctgtttg                    39
```

<210> SEQ ID NO 90
<211> LENGTH: 39
<212> TYPE: DNA
<213> ORGANISM: Erythrovirus B19

<400> SEQUENCE: 90

```
ttaataacag tggggaggc tgggattttt gtccccatt                    39
```

<210> SEQ ID NO 91
<211> LENGTH: 39
<212> TYPE: DNA
<213> ORGANISM: Erythrovirus B19

<400> SEQUENCE: 91

```
cagtgggga ggcttgggat tttgtcccca ttgcattaa                    39
```

<210> SEQ ID NO 92
<211> LENGTH: 39
<212> TYPE: DNA
<213> ORGANISM: Erythrovirus B19

<400> SEQUENCE: 92

```
gcaaaaaatg tgcttaccta tctggcttgc aaagttttg                   39
```

<210> SEQ ID NO 93
<211> LENGTH: 39
<212> TYPE: DNA
<213> ORGANISM: Erythrovirus B19

<400> SEQUENCE: 93

```
aatgtgctta cctatctggc ttgcaaagtt ttgtagatt                   39
```

<210> SEQ ID NO 94
<211> LENGTH: 39
<212> TYPE: DNA
<213> ORGANISM: Erythrovirus B19

<400> SEQUENCE: 94

```
tttgtagatt atgagtaaag aaattggtaa atggtggga                   39
```

<210> SEQ ID NO 95
<211> LENGTH: 39
<212> TYPE: DNA
<213> ORGANISM: Erythrovirus B19

<400> SEQUENCE: 95

```
ttatgagtaa agaaattggt aaatggtggg aaagtgatg                   39
```

<210> SEQ ID NO 96
<211> LENGTH: 39
<212> TYPE: DNA
<213> ORGANISM: Erythrovirus B19

<400> SEQUENCE: 96

```
cttctttgtt tgacttagtg gctcgtatta aaagtaacc                   39
```

<210> SEQ ID NO 97
<211> LENGTH: 39
<212> TYPE: DNA
<213> ORGANISM: Erythrovirus B19

<400> SEQUENCE: 97
atgaaactgg gtttcaagct caagtagtaa aagactact                                    39

<210> SEQ ID NO 98
<211> LENGTH: 39
<212> TYPE: DNA
<213> ORGANISM: Erythrovirus B19

<400> SEQUENCE: 98
tcctgatgct ttaactgttg ccatatcaga aattgccat                                    39

<210> SEQ ID NO 99
<211> LENGTH: 39
<212> TYPE: DNA
<213> ORGANISM: Erythrovirus B19

<400> SEQUENCE: 99
ttgccatatc agaaattgcc attaaagatg ttacagaca                                    39

<210> SEQ ID NO 100
<211> LENGTH: 39
<212> TYPE: DNA
<213> ORGANISM: Erythrovirus B19

<400> SEQUENCE: 100
tgccatatca gaaattgcca ttaaagatgt tacagacaa                                    39

<210> SEQ ID NO 101
<211> LENGTH: 39
<212> TYPE: DNA
<213> ORGANISM: Erythrovirus B19

<400> SEQUENCE: 101
aatacaagta cccatatgta ttaggtcaag gacaagata                                    39

<210> SEQ ID NO 102
<211> LENGTH: 39
<212> TYPE: DNA
<213> ORGANISM: Erythrovirus B19

<400> SEQUENCE: 102
aagatacctt agccccagag cttccaattt gggtgtact                                    39

<210> SEQ ID NO 103
<211> LENGTH: 39
<212> TYPE: DNA
<213> ORGANISM: Erythrovirus B19

<400> SEQUENCE: 103
cagtaggaga tgtaaacacg cagggaattt ctggggaca                                    39

<210> SEQ ID NO 104
<211> LENGTH: 39
<212> TYPE: DNA
<213> ORGANISM: Erythrovirus B19

<400> SEQUENCE: 104
agaatcagcg ttttatgtcc tggaacacag ctcttttga                                    39

<210> SEQ ID NO 105
<211> LENGTH: 39
<212> TYPE: DNA
<213> ORGANISM: Erythrovirus B19

<400> SEQUENCE: 105
ctactatgtc ttataagttc cctccagtgc ccccagaga					39

<210> SEQ ID NO 106
<211> LENGTH: 39
<212> TYPE: DNA
<213> ORGANISM: Erythrovirus B19

<400> SEQUENCE: 106
tccctccagt gccccagag aatttagaag gctgtagtc					39

<210> SEQ ID NO 107
<211> LENGTH: 39
<212> TYPE: DNA
<213> ORGANISM: Erythrovirus B19

<400> SEQUENCE: 107
cccgtttagg agtccctgat acattaggag gggacccca					39

<210> SEQ ID NO 108
<211> LENGTH: 39
<212> TYPE: DNA
<213> ORGANISM: Erythrovirus B19

<400> SEQUENCE: 108
aacacatgaa gaccacgcag ttcagccaca aaattttat					39

<210> SEQ ID NO 109
<211> LENGTH: 39
<212> TYPE: DNA
<213> ORGANISM: Erythrovirus B19

<400> SEQUENCE: 109
acgcagttca gccacaaaat tttatgccag ggccactgg					39

<210> SEQ ID NO 110
<211> LENGTH: 39
<212> TYPE: DNA
<213> ORGANISM: Erythrovirus B19

<400> SEQUENCE: 110
ggccactggt aaactcagtt tccacaaagg agggagaca					39

<210> SEQ ID NO 111
<211> LENGTH: 39
<212> TYPE: DNA
<213> ORGANISM: Erythrovirus B19

<400> SEQUENCE: 111
aggagggaga cagttctaac acaggagcgg gaaaagccc					39

<210> SEQ ID NO 112
<211> LENGTH: 39
<212> TYPE: DNA
<213> ORGANISM: Erythrovirus B19

<400> SEQUENCE: 112
gtcaaagtac tagaatatca ttacgccctg gtccagtgt					39

<210> SEQ ID NO 113
<211> LENGTH: 39
<212> TYPE: DNA

<213> ORGANISM: Erythrovirus B19

<400> SEQUENCE: 113
gccctggtcc agtgtctcaa ccatatcacc actgggaca                              39

<210> SEQ ID NO 114
<211> LENGTH: 39
<212> TYPE: DNA
<213> ORGANISM: Erythrovirus B19

<400> SEQUENCE: 114
gtccagtgtc tcaaccatat caccactggg acacagata                              39

<210> SEQ ID NO 115
<211> LENGTH: 39
<212> TYPE: DNA
<213> ORGANISM: Erythrovirus B19

<400> SEQUENCE: 115
cagataaata tgtaacaggg ataaatgcca tttctcatg                              39

<210> SEQ ID NO 116
<211> LENGTH: 39
<212> TYPE: DNA
<213> ORGANISM: Erythrovirus B19

<400> SEQUENCE: 116
ctgaagacaa agagtatcaa cagggcgtgg gtaggtttc                              39

<210> SEQ ID NO 117
<211> LENGTH: 39
<212> TYPE: DNA
<213> ORGANISM: Erythrovirus B19

<400> SEQUENCE: 117
aagacaaaga gtatcaacag ggcgtgggta ggtttccca                              39

<210> SEQ ID NO 118
<211> LENGTH: 39
<212> TYPE: DNA
<213> ORGANISM: Erythrovirus B19

<400> SEQUENCE: 118
agggcgtggg taggtttccc aatgaaaaag aacaactaa                              39

<210> SEQ ID NO 119
<211> LENGTH: 39
<212> TYPE: DNA
<213> ORGANISM: Erythrovirus B19

<400> SEQUENCE: 119
aacagttaca gggtttaaat atacacacat attttccca                              39

<210> SEQ ID NO 120
<211> LENGTH: 39
<212> TYPE: DNA
<213> ORGANISM: Erythrovirus B19

<400> SEQUENCE: 120
gtttaaatat acacacatat tttcccaata aaggtaccc                              39

<210> SEQ ID NO 121
<211> LENGTH: 39

-continued

<212> TYPE: DNA
<213> ORGANISM: Erythrovirus B19

<400> SEQUENCE: 121
taccaaattt agatgacagc tttaaaactc agtttgcag                                    39

<210> SEQ ID NO 122
<211> LENGTH: 39
<212> TYPE: DNA
<213> ORGANISM: Erythrovirus B19

<400> SEQUENCE: 122
agctttagga ggttggggac tacatcagcc accccctca                                    39

<210> SEQ ID NO 123
<211> LENGTH: 39
<212> TYPE: DNA
<213> ORGANISM: Erythrovirus B19

<400> SEQUENCE: 123
ggccaattgg gggtattaag tcaatgggaa taacaacat                                    39

<210> SEQ ID NO 124
<211> LENGTH: 39
<212> TYPE: DNA
<213> ORGANISM: Erythrovirus B19

<400> SEQUENCE: 124
ttaagtcaat gggaataaca acattagttc aatatgctg                                    39

<210> SEQ ID NO 125
<211> LENGTH: 39
<212> TYPE: DNA
<213> ORGANISM: Erythrovirus B19

<400> SEQUENCE: 125
tagttcaata tgctgtgggt attatgacag taactatga                                    39

<210> SEQ ID NO 126
<211> LENGTH: 39
<212> TYPE: DNA
<213> ORGANISM: Erythrovirus B19

<400> SEQUENCE: 126
taactatgac atttaaatta gggcctcgca aagctacag                                    39

<210> SEQ ID NO 127
<211> LENGTH: 39
<212> TYPE: DNA
<213> ORGANISM: Erythrovirus B19

<400> SEQUENCE: 127
accctcctca cgcagcaggc catttaccat atgtactat                                    39

<210> SEQ ID NO 128
<211> LENGTH: 4611
<212> TYPE: DNA
<213> ORGANISM: Erythrovirus B19

<400> SEQUENCE: 128
acgcggggac tacagtatat atagcacggc actgccgcag ctctttcttt ctgagctgct             60
ttttcctgga cttcttgct gttgtttgtg agctaactaa caggtattta tactacttgt            120

```
taacatacta acatggagct atttagaggg gtgcttcaag tttcttctaa tgttctggac    180
tgtgctaacg ataactggtg gtgctctttta ctggatttag acacctctga ctgggaacca    240
ctaactcata ctaacagact aatggcaata tacctaaaac agtgtggctt ctaagcttga    300
ctttaccggg gggccactag cagggtgctt gtactttttt caagttgaat gtaacaaatt    360
tgaagaaggc tatcatattc atgtggttat tgggggggcca gggttaaacc ccagaaacct    420
aacagtgtgt gtagagggt tatttaacaa tgtactttat cacccttgtaa ctggagatgt    480
aaagctaaaa tttttgccag gaatgactac aaaaggcaaa tactttagag atggagagca    540
gtttatagaa aactatttaa tgaaaaaaat accttttgaat gttgtatggt gtgttactaa    600
tattgatgga tatatagata cctgtatttc tgctactttt agaaggggag cttgccatgc    660
caagaaaccc cgcatgacca cagccataaa tgatactagt agtgatgctg gggagtctag    720
cggcacaggg gcagaggttg tgccatttaa tggaaaggga actaaggcta gcataaagtt    780
tcagactatg gtaaactggt tgtgtgaaaa tagagtgttt acagaggata agtgaaaact    840
agttgacttt aaccagtaca ctttactaag cagtagtcac agtggaagtt ttcaaattca    900
aagtgcacta aaactagcaa tttataaagc aactaattta gtgcctacta gcacatttt    960
attgcataca gactttgagc aggttatgtg tattaaagac aataaaattg ttaaattgtt   1020
actttgtcaa aactatgacc ccctattggt ggggcagcat gtgttaaagt ggattgataa   1080
aaaatgtggc aagaaaaata cactgtggtt ttatgggccg ccaagtacag gaaaaacaaa   1140
cttggcaatg gctattgcta aaagtgttcc agtatatggc atggttaact ggaataatga   1200
aaactttcca tttaatgatg tagcaggaa agcttggtg gtctgggatg aaggtattat   1260
taagtccaca attgtagaag ctgcaaaagc catttttaggc gggcaaccta ccagggtaga   1320
tcaaaaaatg cgtggaagtg tagctgtgcc tggagtacct gtggttataa ccagcaatgg   1380
tgacattact tttgttgtaa gcgggaacac tacaacaact gtacacgcta aagccttaaa   1440
agagcgcatg gtaaagttaa actttactgt aagatgcagc cctgacatgg ggttactaac   1500
agaggctgat gtacaacagt ggcttacatg gtgtaatgca caaagctggg accactatga   1560
aaactgggca ataaactaca cttttgtattt ccctggaatt aatgcagatg ccctccaccc   1620
agacctccaa accacccccaa ttgtcacaga caccagtatc agcagcagtg gtggtgaaag   1680
ctctgaagaa ctcagtgaaa gcagtttttt taacctcatc accccaggcg cctgaacac    1740
tgaaaccccg cgctctagta cgcccatccc cgggaccagt tcaggagaat catctgtcgg   1800
aagcccagtt cctccgaagg ttgtagctgc atcgtgggaa gaagccttct acacacctt   1860
ggcagaccag tttcgtgaac tgttagttgg ggttgattat gtgtgggacg gtgtaagggg   1920
tttacctgtg tgttgtgtgc agcatattaa caatagtggg ggaggcttgg gactttgtcc   1980
ccattgcatt aatgtagggg cttggtataa tggatggaaa tttcgagaat ttaccccaga   2040
tttggtgcgg tgtagctgcc atgtgggagc ttctaatccc tttttctgtgc taacctgcaa   2100
aaaatgtgct tacctgtctg gattgcaaag cttttgtagat tatgagtaaa gaaagtggca   2160
aatggtggga aagtgatgat aaatttgcta aagctgtgta tcagcaattt gtggaatttt   2220
atgaaaagct tactggaaca gactagagc ttattcaaat attaaagat cattacaata   2280
tttctttaga taatccccta gaaaacccat cctctctgtt tgacttagtt gctcgtatta   2340
aaaataacct taaaaactct ccagactat atagtcatca ttttcaaagt catggacagt   2400
tatctgacca ccccccatgcc ttatcatcca gtaacagtca tgcagaacct agaggagaaa   2460
atgcagtatt atctagtgaa gacttacaca agcctgggca agttagcgta caactacccg   2520
```

```
gtactaacta tgttgggcct ggcaatgagc tacaagctgg gcccccgcaa agtgctgttg    2580
acagtgctgc aaggattcat gactttaggt atagccaact ggctaagttg gaataaatc     2640 catatactca ttggactgta gcagatgaag agcttttaaa taatataaaa aatgaaactg    2700
ggtttcaagc acaagtagta aaagactact ttactttaaa aggtgcagct gcccctgtgg    2760
cccattttca aggaagtttg ccggaagttc ccgcttacaa cgcctcagaa aaatacccaa    2820
gcatgacttc agtaattct gcagaagcca gcactggtgc aggagggggg ggcagtaatc     2880
ctgttaaaag catgtggagt gaggggggcca cttttagtgc caactctgta acttgtacat   2940
tttccagaca gtttttaatt ccatatgacc cagagcacca ttataaggtg ttttctcccg    3000
cagcaagtag ctgccacaat gccagtggaa aggaggcaaa ggtttgcacc attagtccca    3060
taatgggata ctcaaccccca tggagatatt tagattttaa tgctttaaat ttgtttttt     3120 cacctttaga gtttcagcat ttaattgaaa actatggaag tatagctcct gatgctttaa    3180
ctgtaaccat atcagaaatt gctgttaagg atgttacaga caaaactgga gggggagtac    3240
aagttactga cagcactacc gggcgcctat gcatgttagt agaccatgaa tacaagtacc    3300
catatgtgtt agggcaaggt caggatactt tagcccccaga acttcctatt tgggtatact    3360
ttccccctca atatgcttac ttgacagtag agatgttaa cacacaagga atttctggag     3420
acagcaaaaa attagcaagt gaagaatcag catttatgt tttggaacac agttcttttc      3480
agcttttagg tacaggaggt acagcaacta tgtcctataa gtttcctcca gtgccccag     3540 aaaatttaga gggctgcagt caacactttt atgaaatgta caatccctta tacggatctc    3600 gcttagggt ccctgacaca ttaggaggtg acccaaaatt tagatcttta acacatgaag     3660
accatgcaat tcagccccaa aactttatgc cagggccact agtaaactca gtgtctacaa    3720
aggagggaga cagctctagt actggagctg gaaaagcctt aacaggcctt agcacaggaa    3780
cctctcaaaa cactagaata tccttacgcc ctgggccagt gtctcagcca tatcaccact    3840
gggacacaga taaatatgtt acaggaataa atgccatttc tcatggtcag accacatatg    3900
gtaatgctga agataaagag tatcagcaag gagtgggtag atttccaaat gaaaagaac     3960 agctaaaaca gttacagggc ttaaacatgc acacctattt tcccaataaa ggaacccagc    4020
aatatacaga tcaaattgag cgcccccctaa tggtgggttc tgtatggaac agaagagccc    4080
ttcactatga aagccagctg tggagtaaaa ttccaaattt agatgacagt tttaaaactc    4140
agtttgcagc cttaggagga tgggggtttgc atcagccacc tcctcaaata ttttaaaaa    4200 tattaccaca aagtgggccc attggaggta ttaaatcaat gggaattact accttagttc    4260
agtatgccgt gggaattatg acagtcacta tgacattaa attgggggcc cgtaaagcta    4320
cgggacggtg gaatcctcaa cctggagtat atccccgca cgccgcaggt catttaccat    4380
atgtactata tgacccaca gctacagatg caaaacaaca ccacagacat ggatatgaaa    4440
agcctgaaga attgtggaca gccaaaagcc gtgtgcaccc attgtaaaca ctcccaccg     4500 tgccctcagc caggatgcgt aactaaacgc ccaccagtac cacccagact gtacctgccc    4560
ccgcgtatac ctataagaca gcctaacaca aagatatag acaatgtaga a              4611
```

<210> SEQ ID NO 129
<211> LENGTH: 4846
<212> TYPE: DNA
<213> ORGANISM: Erythrovirus B19

<400> SEQUENCE: 129

```
atctgatttg gtgtcttctt tttaaaattt tggcgggctt tttcccgcct tatgcaaata    60
agctgccatg tttaatattt tattttaatt taattggaca gacgcctaac ggttattata   120
ggcggagtta cgggcggtat ataagcagct gtgctctgtg gcactttctt ttctggttgc   180
ttttgactgg aactcacttg ctgttctttg cctgctaact aacaggtatt tatactaact   240
tttaatttac taacatggag ctatttcggg gtgtcttgca catttcctct aacattctgg   300
actgtgctaa tgataactgg tggtgctcta tgctagactt agatacttct gattgggaac   360
cactaactca ttctaacaga ttaatggcaa tatatttaag cagtgttgct tctaagcttg   420
attttactgg ggggccgcta gcaggttgct tatactttt ccaggtggag tgtaacaaat   480
ttgaggaagg ctatcatatt catgtagtta ttggtggtcc aggactaaat gctagaaact   540
taactgtgtg tgtagaaggt ttatttaata atgttcttta ccaccttgta actgaaagtg   600
ttaaacttaa attttttgcca gggatgacta ccaaaggaaa atattttaga gatggagagc   660
agtttataga aaattactta atgaaaaaaa ttccttaaaa tgttgtgtgg tgtgtaacaa   720
atattgacgg gtatatagac acctgtattt ccgcctcttt tcggcgagga gcttgtcaag   780
ctaaaagacc ccgcattgcc gcaaatgcag acagtgttac tagtgaaacc ggggagtcta   840
gctgtgcagg gggagatgtt gtaccatttg ctggaaaggg aacaaaagcg gggttaaagt   900
ttcaaaccat ggtaaattgg ctatgtgaaa acagagtatt tactgaagat aaatggaagt   960
tagtagattt taaccagtat accttattaa gtagtagtca cagtggcagc tttcaaatac  1020
aaagtgcctt aaagttagct atttataaag ctactaactt agtacccact agtacattct  1080
tgttacatgc agactttgag caggttactt gcattaaaga aaataaaata gttaaattat  1140
tactgtgtca aaactatgat cctctgctag tggggcaaca tgtgttaagg tggattgaca  1200
aaaaatgtgt taaaaaaaac accctatggt tttacgggcc accaagtact ggaaaaacaa  1260
atttagctat ggctattgct aaaactgtac ccgtgtatgg aatggttaac tggaataatg  1320
aaaactttcc atttaatgat gtggcgggga aaagtttggt ggtctgggat gaaggcatta  1380
ttaagtccac tattgtggaa gctgcaaaag ccattctagg tggtcagcca accagggtag  1440
atcagaaaat gcgtggcagt gtggcagtgc ccggtgtgcc tgtggtcata accagcaacg  1500
gtgacattac atttgttgta agtggtaata ccactacaac tgtgcatgct aaagccttaa  1560
aagaacggat ggtaaagcta aatttttacca taaggtgtag ccctgacatg ggtttactaa  1620
cagaggctga tgtgcaacag tggctaactt ggtgtaatgc acaaagctgg agccactatg  1680
aaaactgggc aataaactac acgtttgatt tccctggaat aaatgcagat gccctccacc  1740
cagatctcca aaccaccccc attgtcccag acaccagtat cagcagcagt ggtggtgaaa  1800
gctctgaaga actcagtgaa agcagctttt tcaacctcat cactccaggc gcctggaaca  1860
gtgaaacccc gcgctctagt acgcccgtcc ccgggaccag ttcaggagaa tcatttgtcg  1920
gaagcccagt ttcctccgaa gtggtagccg cgtcgtggga ggaagctttt tacacgccgc  1980
ttgcagatca gtttcgtgaa ctgttagtag gggttgacta tgtatgggat ggtgtaaggg  2040
gattgcctgt ttgctgtgtg gaacatatta ataacagtgg gggagggttg gggctttgtc  2100
ctcattgtat tcatgtggga gcttggtata atggatggaa atttagagag tttactccag  2160
acttagtgcg ctgtagttgt catgtaggag cctctaaccc attttctgtg ttaacttgta  2220
aaaaatgtgc ttacctgtct ggtttacaaa gctttgtaga ttatgagtaa aaccactgac  2280
aaatggtggg aaagtagtga caaatttgcc caggacgtgt ataagcagtt tgtacaattt  2340
tatgaaaaag ctactggaac agatttagag cttattcaaa ttttaaaaga tcattacaac  2400
```

```
atttctttag acaatccttt agaaaacccc tcttctttat ttgacttagt tgctcgcatt    2460
aaaagcaatc ttaaaaactc tccagaccta tatagtcatc attttcagag ccatggacag    2520
ttatctgacc accccattc cttatcaccc agtaacagta gtacagaacc tagaggagaa    2580
aatgcagtat tatctagtga agacttacac aagcctgggc aagttagcat acaattaccc    2640
ggtactaact atgttgggcc tggcaatgag ctacaagctg ggcctccgca gaatgctgtg    2700
gacagtgctg caaggattca tgactttagg tatagccaat tggctaagtt gggaataaat    2760
ccttatactc attggacggt agcagatgag gaattgttaa aaatatataaa aaatgaaaca    2820
gggtttcaag cacaagcagt aaaagactac tttactttaa aaggtgcagc tgcccctgtg    2880
gcccattttc aaggaagttt accggaagtg cccgcgtaca acgcctcaga aaatacccc    2940
agcatgactt cagttaactc tgcagaagcc agcactggtg caggcggggg aggtagcaac    3000
cctacaaaaa gcatgtggaa tgaaggggct acattcactg ctaattctgt aacatgcaca    3060
ttctctaggc aattttttaat tccatatgat ccagagcatc attataaagt gttctcccca    3120
gcagctagta gctgccacaa tgctagcgga aaagaggcaa aagtgtgcac tattagtccc    3180
attatggggt actctactcc gtggagatac ttagatttta atgctttaaa cttgtttttc    3240
tcaccattag agtttcagca cttaattgaa aattatggca gcatagctcc agatgcttta    3300
actgtaacta tttcagaaat tgctgtaaaa gatgttacag acaaaacagg gggaggtgtg    3360
caagttactg acagcacaac aggacgtttg tgtatgttag tggatcatga gtataagtac    3420
ccatatgtgc taggtcaggg acaagacaca ctagctccag aactgcccat ttgggtgtac    3480
tttccccccc aatatgctta cttaacagta ggtgaagtaa acacacaagg aatttcagga    3540
gacagcaaaa aattagctag tgaagaatca gcttttttatg tgttagagca cagttcattt    3600
gaactttttag gtacaggggg atcagccaca atgtcctaca aatttccagc agtgccccca    3660
gaaaacttag aaggttgcag ccaacatttt tatgaaaatgt acaacccct gtacggttcc    3720
cgattagggg tacctgacac attaggaggg gaccctaaat ttagatcatt aacacacgaa    3780
gaccatgcaa ttcagccaca aaactttatg cctgggccac taataaaattc agtatctacc    3840
aaagaaggag acaattctaa tacaggtgct ggaaaagccc ttacggggct tagtactggc    3900
actagtcaaa acaccagaat ttccctacgc ccagggccag tgtctcagcc ataccatcac    3960
tgggacactg ataaatatgt tacaggaata aatgccattt cacatggaca aaccacctat    4020
ggaaatgctg aggacaaaga atatcagcaa ggggtaggaa gatttccaaa cgaaaaagaa    4080
cagcttaagc agttacaggg tcttaacatg cacacatact ttcctaataa aggaacccaa    4140
caatacacag accaaattga acgccccctt atggtaggct ctgtttggaa cagaagagca    4200
cttcactatg aaagtcagct gtggagtaaa atccctaact tagatgatag ttttaaaact    4260
caatttgcag ccctaggagg ttggggttg catcaaccac ccctcaaat atttttaaaa    4320
atactaccgc aaagtgggcc aattggaggt attaaatcca tggaattac tactttagtt    4380
caatatgctg tgggaataat gacagttact atgacattta aattgggacc tcgaaaggct    4440
actggaaggt ggaatcccca gcctggagtg tatcctcctc atgcagctgg tcatttacca    4500
tatgtactgt atgaccccac agctacagat gcaaagcaac accacagaca cggatatgaa    4560
aagcctgaag aattgtggac tgccaaaagc cgtgtgcacc cattgtaaac attccccacc    4620
gtgccctctg ccaggaaccg tcaccaatcg cccacctgta ccgccagat tatatgtgcc    4680
ccctccaata ccccgtaggc aaccatctat aaaagataca gacgctgtag agtataaatt    4740
```

```
actaacccga tatgaacaac atgtaataag aatgctaaga ttatgtaata tgtacacaaa    4800
cttggaaaaa taaaaacctt aaataaaaaa ttaatagtgt atggtg                   4846

<210> SEQ ID NO 130
<211> LENGTH: 5112
<212> TYPE: DNA
<213> ORGANISM: Erythrovirus B19

<400> SEQUENCE: 130
gaattccgcc aaatcagatg ccgccggtcg ccgccggtag gcgggacttc cggtacaaga      60
tggcggacaa ttacgtcatt tcctgtgacg tcatttcctg tgacgtcaca ggaaatgacg     120
taattgtccg ccatcttgta ccggaagtcc cgcctaccgg cggcgaccgg cggcatctga     180
tttggtgtct tcttttaaat tttagcgggc ttttttcccg ccttatgcaa atgggcagcc     240
attttaagtg ttttactata attttattgg ttagttttgt aacggttaaa atgggcggag     300
cgtaggcggg gactacagta tatatagcac ggtactgccg cagctctttc tttctgggct     360 gcttttcct ggactttctt gctgtttttt gtgagctaac taacaggtat ttatactact      420
tgttaacatc ctaacatgga gctatttaga ggggtgcttc aagtttcttc taatgttcta     480
gactgtgcta acgataactg gtggtgctct ttactggatt tagacacttc tgactgggaa     540
ccactaactc atactaacag actaatggca atatacttaa gcagtgtggc ttctaagctt     600
gactttaccg gggggccact agcagggtgc ttgtactttt tcaagtaga atgtaacaaa      660 tttgaagaag gctatcatat tcatgtggtt actgggggc cagggttaaa ccccagaaac      720
cttacagtgt gtgtagaggg gttatttaat aatgtacttt atcaccttgt aactgaaaat     780
gtgaagctaa aattttgcc aggaatgact acaaaaggca atactttag agatggagag       840 cagtttatag aaaactattt aatgaaaaaa ataccttaa atgttgtatg gtgtgttact       900
aatattgatg gatatataga tacctgtatt tctgctactt ttagaagggg agcttgccat     960
gccaagaaac cccgcattac cacagccata atgatactag tagtgatgc tggggagtct    1020 agcggcacag gggcagaggt tgtgccattt aatgggaagg gaactaaggc tagcataaag    1080
tttcaaacta tggtaaactg gttgtgtgaa acagagtgt ttacagagga taagtggaaa     1140
ctagttgact ttaaccagta cactttacta agcagtagtc acagtggaag ttttcaaatt    1200
caaagtgcac taaaactagc aatttataaa gcaactaatt tagtgcctac tagcacattt    1260
ttattgcata cagactttga gcaggttatg tgtattaaag acaataaaat tgttaaattg    1320
ttactttgtc aaaactatga ccccctattg gtggggcagc atgtgttaaa gtggattgat    1380
aaaaaatgtg gtaagaaaaa tacactgtgg ttttatgggc cgccaagtac aggaaaaaca    1440
aacttggcaa tggccattgc taaaagtgtt ccagtatatg gcatggttaa ctggaataat    1500
gaaaactttc catttaatga tgtagcagga aaaagcttgg tggtctggga tgaaggtatt    1560
attaagtcta caattgtaga agctgcaaaa gccatttag gcgggcaacc caccagggta     1620
gatcaaaaaa tgcgtggaag tgtagctgtg cctggagtac ctgtgttat aaccagcaat    1680 ggtgacatta ctttgtgt aagcgggaac actacaacaa ctgtacatgc taaagcctta     1740
aaagagcgca tggtaaagtt aaactttact gtaagatgca gccctgacat ggggttacta    1800
acagaggctg atgtacaaca gtggcttaca tggtgtaatg cacaaagctg ggaccactat    1860
gaaaactggg caataaacta cacttttgat ttccctggaa ttaatgcaga tgccctccac    1920
ccagacctcc aaaccacccc aattgtcaca gacaccagta tcagcagcag tggtggtgaa    1980
agctctgaag aactcagtga aagcagcttt tttaacctca tcacccccagg cgcctggaac    2040
```

```
actgaaaccc cgcgctctag tacgcccatc cccgggacca gttcaggaga atcatttgtc    2100
ggaagcccag tttcctccga agttgtagct gcatcgtggg aagaagcctt ctacacacct    2160
ttggcagacc agtttcgtga actgttagtt ggggttgatt atgtgtggga cggtgtaagg    2220
ggtttacctg tgtgttgtgt gcaacatatt aacaatagtg ggggagggtt gggactttgt    2280
ccccattgca ttaatgtagg ggcttggtat aatggatgga aatttcgaga atttacccca    2340
gatttggtgc gatgtagctg ccatgtggga gcttctaatc cctttctgt gctaacctgc    2400 aaaaaatgtg cttacctgtc tggattgcaa agctttgtag attatgagta aaaaagtgg    2460 caaatggtgg gaaagtgatg ataaatttgc taaagctgtg tatcagcaat ttgtggaatt    2520
ttatgaaaag gttactggaa cagacttaga gcttattcaa atattaaaag atcattataa    2580
tatttcttta gataatcccc tagaaaaccc atcctctctg tttgacttag ttgctcgtat    2640
taaaaataac cttaaaaact ctccagactt atatagtcat cattttcaaa gtcatggaca    2700
gttatctgac caccccatg ccttatcatc cagtagcagt catgcagaac ctagaggaga    2760
aaatgcagta ttatctagtg aagacttaca caagcctggg caagttagcg tacaactacc    2820
cggtactaac tatgttgggc ctggcaatga gctacaagct gggcccccgc aaagtgctgt    2880
tgacagtgct gcaaggattc atgactttag gtatagccaa ctggctaagt tgggaataaa    2940
tccatatact cattggactg tagcagatga agagcttta aaaatataa aaatgaaac    3000 tgggtttcaa gcacaagtag taaaagacta ctttacttta aaggtgcag ctgcccctgt    3060 ggcccatttt caaggaagtt tgccggaagt tcccgcttac aacgcctcag aaaaatacccc    3120 aagcatgact tcagttaatt ctgcagaagc cagcactggt gcaggagggg ggggcagtaa    3180
ttctgtcaaa agcatgtgga gtgaggggc cacttttagt gctaactctg taacttgtac    3240
attttccaga cagttttaa ttccatatga cccagagcac cattataagg tgttttctcc    3300
cgcagcgagt agctgccaca atgccagtgg aaaggaggca aaggtttgca ccatcagtcc    3360
cataatggga tactcaaccc catggagata tttagatttt aatgctttaa atttattttt    3420 ttcacccttta gagtttcagc acttaattga aaattatgga agtatagctc ctgatgcttt    3480
aactgtaacc atatcagaaa ttgctgttaa ggatgttaca gacaaaactg gaggggggt    3540 acaggttact gacagcacta cagggcgcct atgcatgtta gtagaccatg aatacaagta    3600
cccatatgtg ttagggcaag gtcaggatac tttagcccca gaacttccta tttgggtata    3660 cttccccct caatatgctt acttaacagt aggagatgtt aacacacaag gaatttctgg    3720
agacagcaaa aaattagcaa gtgaagaatc agcatttat gttttggaac acagttcttt    3780 tcagcttta ggtacaggag gtacagcatc tatgtcttat aagtttcctc cagtgccccc    3840
agaaaattta gagggctgca gtcaacactt ttatgaaatg tacaatccct tatacgatc    3900 ccgcttaggg gttcctgaca cattaggagg tgacccaaaa tttagatctt taacacatga    3960
agaccatgca attcagccccc aaaacttcat gccaggccca ctagtaaact cagtgtctac    4020
aaaggaggga gacagctcta atactggagc tggaaaagcc ttaacaggcc ttagcacagg    4080
tacctctcaa aacactagaa tatccttacg ccctgggcca gtgtctcagc cataccacca    4140
ctgggacaca gataaatatg tcacaggaat aaatgccatt tctcatggtc agaccactta    4200
tggtaacgct gaagacaaag agtatcagca aggagtgggt agatttccaa atgaaaaaga    4260
acagctaaaa cagttacagg gtttaaacat gcacacctac tttcccaata aaggaaccca    4320
gcaatataca gatcaaattg agcgcccct aatggtgggt tctgtatgga acagaagagc    4380
```

```
ccttcactat gaaagccagc tgtggagtaa aattccaaat ttagatgaca gttttaaaac    4440
tcagtttgca gccttaggag gatggggttt gcatcagcca cctcctcaaa tattttaaa     4500 aatattacca caaagtgggc caattggagg tattaaatca atgggaatta ctaccttagt    4560
tcagtatgcc gtgggaatta tgacagtaac tatgacattt aaattggggc ccgtaaagc     4620 tacgggacgg tggaatcctc aacctggagt atatcccccg cacgcagcag gtcatttacc    4680
atatgtacta tatgacccca cagctacaga tgcaaaacaa caccacagac atggatatga    4740
aaagcctgaa gaattgtgga cagccaaaag ccgtgtgcac ccattgtaaa cactccccac    4800
cgtgccctca gccaggatgc gtaactaaac gcccaccagt accacccaga ctgtacctgc    4860
cccctcctgt acctataaga cagcctaaca caaagatat agacaatgta gaatttaagt     4920
acttaaccag atatgaacaa catgttatta gaatgttaag attgtgtaat atgtatcaaa    4980
atttagaaaa ataaacattt gttgtggtta aaaaattatg ttgttgcgct ttaaaaattt    5040
aaaagaagac accaaatcag atgccgccgg tcggccggta ggcgggactt ccggtacaag    5100
atggcggaat tc                                                       5112

<210> SEQ ID NO 131
<211> LENGTH: 4844
<212> TYPE: DNA
<213> ORGANISM: Erythrovirus B19

<400> SEQUENCE: 131
ttttaaattt tcgcgggctt tttcccgcct tatgcaaatt acctgccatg tttaatgctt      60
tattttaatt tgattggaca aaagttaacg gttttatg ggcggagtta cgcaaggtat       120
ataagcagat gaattttgta aaactttctt tcctggctgc ttttactggg gataacttg      180 ctgttatttg cctgctaatt aacaggtatt tatactaact tttaatttac taacatggag     240
ctatttaggg gtgtgttgca tatttcctct aacatttag actgtgctaa tgataactgg      300
tggtgctcta tgctggattt agatacttct gactgggaac cactaactca ctctaacaga     360
ctaatggcaa tatatttaag taatgttgct tctaaactgg attttactgg ggggccgctg     420
gcgggttgct tatacttttt tcaggtggaa tgtaacaaat ttgaggaagg ctaccatatt     480
catgtagtta ttggtggtcc aggacttaat gctagaaact taacagtgtg tgtagaaggc     540
ttgtttaata atgtgcttta ccacctggta aatgaaagtg ttaaactgaa atttttgcca    600
ggaatgacta caaaaggaaa gtattttaga gatggagagc agtttataga aaattaccta     660
atgaaaaaaa ttcctttaaa tgttgtgtgg tgtgtaacaa atattgacgg gtatatagac     720
acctgtattt ctgcatcttt tagacgagga gcttgccatg ctaaaaaacc tcgaattagt     780
acaaacacag acactgtaaa taatgaagga ggggaatcaa gctgtggagg gggagatgtg     840
gtgccatttg ccgggaaggg aaccaaggca ggcttaaagt ttcaaacaat ggtaaattgg     900
ctatgtgaaa acagagtgtt tactgaagac aaatggaagt tagtggattt taatcagtat    960
acattattaa gcagtagtca tagtgggagt tttcaaatac aaagtgcatt aaagctagct    1020
atttataaag ctactaactt agttcctact agtacatttt taatgcattc agactttgag    1080
caggttacct gcattaaaga aaataaaata gttaaactat tattatgcca gaattatgat    1140
cctcttttag tgggtcaaca tgtttttaag tggattgaca aaaatgtgg taaaaaaaac    1200 accctgtggt tttacgggcc cccaagtact ggaaaaacaa atttggcaat ggctattgct    1260
aaaactgtcc cagtgtatgg catggttaat tggaataatg aaaattttcc atttaatgat    1320
gtagcgggga aaagtttggt ggtctgggat gaaggcatta ttaagtccac tattgtggaa    1380
```

```
gctgcaaaag ccatttagg tgggcagcca accagggtag atcaaaaaat gcgtggcagt    1440
gtggcagtgc ctggtgtgcc agtggtaata accagcaatg gtgacattac ctttgttgta    1500
agtggtaata ccactacaac tgtccatgct aaagccttaa aggagcgaat ggtaaagcta    1560
aactttaccg taagatgcag ccctgacatg ggcttactta cagaggctga tgtacagcaa    1620
tggctaactt ggtgtaatgc acaaagctgg aaccactatg aaaactgggc aataaactac    1680
acgtttgatt tccctggaat aaatgcagat gccctccacc cagacctcca aaccgtcccc    1740
attgtcgcag acaccagtgt cagcagcagt ggtggtgaaa gctctgaaga actcagtgaa    1800
agcagctttt tcaacctcat cactcccggc gcctggaaca gtgaaacccc gcgctctagt    1860
acacccgtcc ccgggaccag ttcaggagaa tcatttgtcg gaagcccagt tcctccgaa    1920 gtggtagccg cgtcgtggga ggaagccttt tacactccac ttgcagacca gtttcgtgaa    1980
ctgttagttg ggttgactta tgtgtgggat ggtgtgaggg gattgcctgt ttgttgtgtg    2040
cagcatatta ataatagtgg gggagggtta ggcctttgtc ctcattgtat taatgtggga    2100
gcttggtata atggatggaa gtttcgtgaa tttactccag atttggtacg gtgcagctgc    2160
catgtaggag cttctaatcc cttttctgtg ttaacctgca aaaatgtgc ttacttgtct    2220 ggattacaga gttttgtgga ttatgagtaa aaaaagtgac aagtggtggg aaagtgatga    2280
taaatttgct aaggacgtgt ataagcaatt tgtagaattt tatgaaaaag ttactgagac    2340
agacttagag cttattcaaa tattaaaaga tcattataat atttctttag ataatccctt    2400
agaaaaccca tcttccctgt ttgacttagt tgctcgtatt aaaagtaatc ttaaagacac    2460
tccagaccta tatagtcatc attttcaaag tcatggacag ttatttgacc accccatgc    2520 cttatcaccc agtagcagtc atacagaacc tagaggagaa gatgcagtat tatctagtga    2580
agacttacac aagcctgggc gagttagcat acaactaccc ggtactaact atattgggcc    2640
tggcaatgag ctacaagctg gccccccgca aagtgctgtg gatagtgctg caaggattca    2700
tgactttagg tatagccaat tggctaagct gggaataaat ccatatactc attggactgt    2760
agcagatgag gaactgttaa aaaatataaa aaatgaaact gggtttcaag cacaagcagt    2820
aaaagattac tttactttaa aaggtgcagc tgcccctgtg gcccattttc aaggaagttt    2880
gccggaagtt cccgcataca acgcctcaga aaagtaccca agcatgactt cagttaattc    2940
tgcagaagcc agcactggtg caggagggg aggcagtaat cctgtcaaaa gcatgtggag    3000
tgagggcgcc acttttactg ccaactctgt aacttgtaca ttttccagac agttttttaat    3060 cccatatgac ccagagcacc attataaagt gttttctccc gcagctagta gctgccataa    3120
tgccagtggg aaagaggcaa aggtttgcac tattagtccc ataatgggct actcaacgcc    3180
atggagatac ttagacttta tgctttaaa cttattttt tcacctttag aatttcaaca    3240
tttaattgaa aattatggaa gtatagcccc tgatgcttta actgttacca tatcagaaat    3300
tgctgttaaa gatgttacag acaaaacagg aggagggtg caggttactg acagtactac    3360
agggcgttta tgcatgttag tagatcatga gtacaagtat ccatatgtgt taggtcaggg    3420
acaggatacc ttagccccag aactgcctat ttgggtgtac tttccccctc aatatgctta    3480
tttaaccgtg ggagatgtaa acacacaggg aatttcaggg gacagtaaaa agctagcaag    3540
tgaagaatca gcattttatg ttttggaaca cagttcattt gaactgttag gtacaggtgg    3600
ctctgccact atgtcctata aatttccacc agtgccccca gaaaacttgg agggttgtag    3660
ccaacacttt tatgaaatgt acaacccccct gtatgggtct cgtttagggg tacctgacac    3720
```

```
actagggggg gaccctaaat ttagatcatt aactcacgaa gatcatgcaa ttcagccaca    3780
aaactttatg cctggcccac tagtaaactc agtgtccact aaagagggag acacttccaa    3840
tacaggcgcc ggaaaagccc ttacggggct tagtactggc actagtcaaa gcaccagaat    3900
atccctgcgc ccaggaccag tgtctcagcc ataccattac tgggacactg ataagtatgt    3960
cacaggaata aatgctattt cacacggaca aaccacttat ggaaatgctg aagacaaaga    4020
gtatcagcaa ggggtaggaa gattcccaaa tgaaaagag caacttaaac agttacaagg    4080
cctaaacatt cacacatact ttccaaacaa aggaacccaa caatacacag atcaaattga    4140
acgccccttta atggtagggt ctgtgtggaa cagaagagcc cttcattatg agagtcagct    4200
gtggagtaaa atccccaact tagatgacag ttttaaaacc caatttgcag ccctgggcgg    4260
gtggggttta catcaaccac ctcctcaaat attttttaaaa atactgccac aaagtggacc    4320
aattggggggt attaaatcca tgggaatcac taccctagtt caatatgcag tgggaattat    4380
gacagttact atgacattta aattgggacc tcgtaaggct actggtaggt ggaatccaca    4440
gcctggagtg tatcctcctc atgcagctgg tcatttacca tatgtactgt atgaccctac    4500
agctacagat gcaaaccaac accacaaaca cggatatgaa aagcctgaag aattgtggac    4560
tgccaaaagc cgtgtgcacc cattgtaaac actccccacc gtgtcctcag ccaggaaccg    4620
taaccaaccg tcctcctgta ccacccagat tatatgtgcc cccgccaata ccccgcagag    4680
aaccgcttgt aaaagataca aatgctgtag aatataagtt actaacccgt tatgaacaac    4740
atgtaattag aatgcttaga ttgtgtaata tgtatacaaa tttggaaaaa taaataactt    4800
aaataaaatag ctaatagtgt atgttacttt aaaaattttt aaaa                    4844
```

<210> SEQ ID NO 132
<211> LENGTH: 5028
<212> TYPE: DNA
<213> ORGANISM: Erythrovirus B19

<400> SEQUENCE: 132

```
gacgtcacag gaaatgacgt aactgtccgc catcttgtac cggaagtccc gcctaccggc      60
ggcgaccggc ggcatctgat ttggtgtctt cttttttgaaa ttttggcggg cttttttccg     120
ccttatgcaa ataagcggcc atgttttaatg ttatattta atttaattgg acaaacgcct     180
aacggttact aggggcggag ttacggggcgg tatataagca gctgcgttcc ctgacacttt     240
cttttctggt tgcttttgac tggaactcac ttgctgttct ttgcctgcta agtaacaggt     300
atttatacta acttttaatt tactaacatg gagctatttc ggggtgtctt gcacatttcc     360
tctaacattc tggactgtgc taatgataac tggtggtgct ctatgctaga cttagatact     420
tctgactggg aaccactaac ccattctaac agattaatgg caatatattt aagcagtgtt     480
gcttctaaac ttgatttac tgggggggccg ctagcaggtt gcttatactt ttttcaggtg     540
gaatgtaaca aatttgagga aggctatcat atccatgtag ttattggtgg tccaggacta     600
aatgctagaa acttaactgt gtgcgtagaa ggtttatttta ataatgttct ttaccatctt     660
gtaactgaaa gtgttaaact taaattttg ccagggatga ctaccaaagg aaaatatttt     720
agagatggag agcagtttat agaaaattac ttaatgaaaa aaattccttt aaatgttgtg     780
tggtgtgtaa caaatattga cgggtatata gacacctgta tttccgcctc ttttcggcga     840
ggagcttgtc atgctaaaag accccgcatt actgcaaata cagacagtgc tactaatgaa     900
actggggagt ctagctgtgg agggggagat gttgtgccat cgctggaaa gggaacaaaa     960
gcggggttaa agtttcaaac catggtaaat tggctatgtg aaaacagagt atttactgaa    1020
```

```
gataaatgga aattagtgga ttttaaccaa tatactttat taagtagcag tcacagtggc    1080
agctttcaaa ttcaaagtgc cttaaagtta gctatttata aagctactaa cttagtaccc    1140
actagtacat tcttgttaca ttcagacttt gagcaggtta cttgcattaa agaaaataaa    1200
atagtaaaat tattattgtg tcaaaactat gatcctcttt tagtgggtca acatgtgtta    1260
aggtggattg acaaaaaatg tggtaaaaaa acaccctgt ggttttacgg gccaccaagt     1320 actgaaaaa caaatttggc aatggctatt gctaaaactg taccagtgta tggaatggtg     1380
aattggaata atgaaaactt tccatttaat gatgtagcgg ggaaaagttt ggtggtctgg    1440
gatgaaggca ttattaagtc cactattgtg aagctgcaa aagccatttt aggtggtcag     1500
ccaaccaggg tagatcagaa aatgcgtggc agtgtggcag tgcccggtgt gcctgtggtt    1560
ataaccagca atggtgacat tacatttgtt gtgagtggta ataccactac aactgtgcat    1620
gctaaagcct taaggaacg gatggtaaag ctaaacttta ccataagatg tagccctgac     1680
atgggtttac ttacagaggc tgatgtacaa caatggctaa cttggtgtaa tgcacaaagc    1740
tggagccact atgaaaactg gcaataaaac tacacatttg atttccctgg aataaatgca    1800
gatgccctcc acccagatct ccaaaccacc cccattgtcc cagacaccag tatcagcagc    1860
agtggtggtg aaagctctga agaactcagt gaaagcagct ttttcaacct catcactcca    1920
ggcgcctgga acagtgaaac cccgcgctct agtacgcccg tccccgggac cagttcagga    1980
gaatcatttg tcggaagccc agtttcctcc gaagtggtag ccgcgtcgtg ggaggaagct    2040
ttttacacgc cgcttgccga tcagtttcgt gaactgttag taggggttga ctttgtatgg    2100
gatggtgtga ggggattgcc tgtttgctgt gtggaacata taaacaacag tggggagggg    2160
ttggggcttt gccctcattg tattaatgtg ggagcttggt ataatggatg gaaatttaga    2220
gagtttactc cagacttagt gcgctgcagt tgtcatgtag gagcctctaa cccatttttct   2280 gtgttaactt gtaaaaaatg tgcttacctg tctggattac aaagttttgt agattatgag    2340
taaaaccact aacaaatggt gggaaagcag tgacaaattt gcccaggacg tgtataagca    2400
gtttgtgcaa ttttatgaaa aagctactgg aacagactta gagcttattc aaattttaaa    2460
agaccattac aacatttctt tagataatcc tttagaaaac ccctcttctt tatttgactt    2520
agttgctcgc attaaaagta atcttaaaaa ctctccagac ctatatagtc atcattttca    2580
gagccatgga cagttatctg accacccca tgccttatca tccagtaaca gtagtgcaga     2640
acctagagga gaaatgcag tattatctag tgaagactta cacaagcctg gcaagttag      2700 catacaatta cccggtacta actatgttgg gcctggcaat gagctacaag ctgggcctcc    2760
gcagaatgct gtggacagtg ctgcaaggat tcatgacttt aggtatagcc aattggctaa    2820
gttgggaata atccttata cacattggac ggtagcagat gaagaattgt taaaaaatat     2880
aaaaaatgaa acagggttc aagcacaagc agtaaaagat tactttacttt taaaggtgc     2940 agctgccct gtggcccatt ttcaaggaag tttaccggaa gtgcccgcgt acaacgcctc     3000
agaaaaatac cccagcatga cttcagttaa ctctgcagaa gccagcactg gtgcaggcgg    3060
gggaggtagc aaccctacaa aaagcatgtg gagtgaaggg gctacattta ctgctaattc    3120
tgtaacgtgt acattctcta ggcaattttt aattccatat gatccagagc atcattataa    3180
agtgttctct ccagcagcta gtagctgcca caatgctagt gggaaagagg caaaagtgtg    3240
cactattagt cccattatgg ggtactctac tccgtggaga tacttagatt ttaatgcttt    3300
aaatttgttt ttctcaccat tagagtttca gcacttaatt gaaaattatg gtagtatagc    3360
```

```
tccagatgct ttaactgtaa ctatttcaga aattgctgta aaagatgtca cagacaaaac    3420
aggaggaggt gtgcaagtta ctgacagcac cacaggacgt ttgtgtatgt tagtggatca    3480
tgagtataaa tacccatatg tgctaggtca gggacaagac acactagctc cagaactgcc    3540
catttgggtt tactttcccc cccagtatgc ttacttaaca gtaggtgaag taaacacaca    3600
aggaatttca ggagacagca aaaaattggc tagtgaagaa tcagcttttt atgtgttaga    3660
gcacagttca tttgaacttt tgggtacagg gggatctgcc actatgtcct acaaatttcc    3720
agctgtgccc ccagaaaacc tagaaggctg cagccaacat ttttatgaaa tgtacaaccc    3780
tttgtacggt tctcgtttag gggtacctga cacattagga ggggacccta aatttagatc    3840
attgacacac gaagaccacg caattcagcc acaaaacttt atgcctgggc cactaataaa    3900
ttcagtgtct accaaagaag gagacaattc taatacaggt gctggaaaag cccttacggg    3960
gcttagtact ggcactagcc aaaacaccag aatttcccta cgccccgggc cagtatctca    4020
gccataccat cactgggaca ctgataaata tgttacagga ataaatgcca tttcacatgg    4080
acaaaccact tatggaaatg ctgaggacaa agagtatcag caaggggtag gaagatttcc    4140 aaaatgaaaaa gaacagctta agcagttaca aggtcttaac atgcacacat acttccctaa    4200
taaaggaacc caacaataca cagaccaaat tgaacgccct cttatggtgg gctctgtttg    4260
gaacagaaga gctcttcact atgaaagtca gctgtggagt aaaatcccta acttagatga    4320
cagttttaaa actcaatttg cagccctagg cgggtggggt tgcatcaac cacccccctca    4380 aatatttta aaaatactac cacaaagtgg gccaattgga ggtattaaat ccatgggaat    4440
tactacttta gttcaatatg ctgtgggaat aatgacagtt accatgacct ttaaattggg    4500
acctcgaaag gctactggaa ggtggaatcc ccagcctggc gtttatcctc ctcatgcagc    4560
tggtcattta ccatatgtac tgtatgaccc cacagctaca gatgcaaagc aacaccacag    4620
acacggatat gaaaagcctg aagaattgtg gactgccaaa agccgtgtgc acccattgta    4680
aacattcccc accgtgtcct cagccaggaa ccgtcaccca ccgccacct gtgccgccca    4740 gattatatgt gcccctcca taccccgta ggcaaccatc tataaaagat acagacgctg    4800
tagaatataa attattaact agatatgaac aacatgtaat tagaatgcta agattatgta    4860
atatgtacac aagtttggaa aaataaaagc cttaaataaa taattcatag tgtatggttc    4920
tttaaaaatt tcaaaagaa gacaccaaat cagatgccgc cggtcgccgc cggtaggcgg    4980
gacttccggt acaagatggc ggacagttac gtcatttcct gtgacgtc                5028
```

<210> SEQ ID NO 133
<211> LENGTH: 5017
<212> TYPE: DNA
<213> ORGANISM: Erythrovirus B19

<400> SEQUENCE: 133

```
acaggaaatg acgtaactgt ccgccatctt gaaccggaag tcccgcctac cggcggcgac      60
cggcggcatc tgatttggtg tcttcttttt aaaattttg gcgggctttt tcccgcctta    120
tgcaaatgaa cagccatgtt tggtgtatta ttttaatttt attggacaca ggcctaacgg    180
ttattatagg cggagttacg gacagtatat aagcagctga gttcgtgac actttctttt    240 ctggttgctt cttactggaa ctcacttgct gttatttgcc tgctaactaa caggtattta    300
tactaacttt taacttacta acatggaact atttaggggt gtgctgcaca tttcctctaa    360
cattctggac tgcgctaatg ataactggtg gtgctctatg ctggacctag acacttctga    420 ctggggagcca ctaacccact ctaacagact catggcaata tatttaagca gcgttgcttc    480
```

```
taagcttgat tttactgggg ggccactggc aggttgctta tacttttttc aggtggaatg    540
taacaaattt gaggaaggct atcacattca tgtggttatt ggtggtccag gactgaatgc    600
tagaaattta actgtgtgtg tagaaggttt atttaataat gttctttacc atcttgtaac    660
tgaaactgtt aaacttaaat ttttgccagg gatgactact aaaggaaaat attttagaga    720
tggagagcag tttatagaaa attacttaat gaaaaaaatt cctttaaatg ttgtgtggtg    780
tgtaacaaat attgacgggt atatagacac ctgtatttct gcctcttttc ggcgaggagc    840
ctgtcatgct aaaagacccc gcattactgc aaatacagac aatgttacta gtgaaaccgg    900
ggagtctagc tgtggagggg gagatgttgt accatttgct ggaaagggaa caaaggcagg    960
gttaaagttt caaaccatgg taaattggct atgtgaaaac agagtattta ctgaggataa   1020
atggaaatta gtagatttta accaatatac tttattaagc agtagtcaca gtggcagctt   1080
tcagatacaa agtgcattaa agttagctat ctataaagcc actaacttag tacctactag   1140 cactttttg ttacattcag actttgagca ggttacttgc attaaagata ataaaatagt   1200
taaattgtta ctgtgccaaa actatgatcc tcttctagta gggcaacatg tgttaaagtg   1260
gattgacaaa aaatgtggta aaaaaaacac cttgtggttt tacgggccac caagtactgg   1320
aaaaacaaat ttggctatgg ctattgccaa aactgttcca gtgtatggca tggttaattg   1380
gaataatgaa aactttccat ttaatgatgt agcgggaaaa agtttggtgg tctgggatga   1440
aggcataatt aaatccacta ttgtggaagc tgcaaaagcc attttaggtg gccagccaac   1500
cagggtagat caaaaaatgc gtggcagtgt ggcagtgcct ggtgtgcctg tggttataac   1560
cagcaatggt gacattacct ttgttgtaag tggtaatacc actacaactg tgcatgctaa   1620
agccttaaaa gaaggatgg taaagctaaa ctttaccgta agatgcagcc ctgacatggg   1680
cttacttaca gaggctgatg tgcagcaatg gctaacttgg tgtaatgcac aaagctggaa   1740
ccactatgaa aactgggcaa taaactacac gtttgatttc cctggaataa atgcagatgc   1800
cctccaccca gacctccaaa ccaccccat tgtcccagac accagtatca gcagcagtgg   1860
tggtgaaagc tctgaagaac tcagtgaaag cagcttttc aacctcatca ctccaggcgc   1920
ctggaacagt gaaaccccgc gctctagtac gcccgtcccc gggaccagtt caggagaatc   1980
atttgtcgga agcccagttt cctccgaagt ggtagccgcg tcgtgggagg aagccttta   2040 cacgccactt gcagatcagt ttcgtgaact gttagtaggg gttgactttg tatgggatgg   2100
tgtgagggga ttgcctgttt gttgtgtgga acatattaat aacagtgggg gagggttggg   2160
gctttgtcct cattgtatta atgtgggagc ttggtataat ggatggaaat ttagagagtt   2220
tactccagac ttagtgcgct gtagttgtca tgtaggagct tctaacccat tttctgtgtt   2280
aacttgtaag aaatgtgctt acctgtctgg attacaaagc tttgtagatt atgagtaaaa   2340
ccactgacag atggtgggaa agtaatgaca catttgccca ggacgtgtat aagcaatttg   2400
tacaatttta tgaaaagtc actggtacag atttagaact tattcaaatt ttaaaagatc   2460
attataacat ttctttagat aatcctttag agaacccctc ttccttattt gacttagttg   2520
ctcgcattaa aagtaatctt aaaaactctc cagacctata tagtcatcat tttcagagcc   2580
atggacagtt atctgaccac ccccatgcct tatcatccag taacagtagt acagaaccta   2640
gaggagaaaa tgcagtatta tctaatgaag acttacacaa gcctgggcaa gttagcatgc   2700
aactacccgg tactaactat gttgggcctg gcaatgagtt acaagctggg cctccgcaga   2760
atgctgtgga cagtgctgca aggattcatg actttaggta tagccaattg gctaagttgg   2820
```

```
gaataaaccc ttatactcac tggacggtag cagacgaaga gttgttaaaa aatataaaaa    2880
atgaaacagg gtttcaagca caagcagtaa aagattactt tactttaaaa ggtgcagctg    2940
cccctgtggc ccattttcaa ggaagtttac cggaagtgcc cgcgtacaac gcctcagaaa    3000 aatacccccag catgacttca gttaactctg cagaagccag cactggtgca ggcggggggag   3060 ggagcaaccc tacaaaaagc atgtggagtg aagggctac atttactgct aattctgtaa     3120
catgcacatt ctctaggcag ttttaattc catatgaccc agagcatcat tataaagtat     3180
tttctccagc agccagtagc tgccacaatg ctagtgggaa agaggcaaaa gtgtgcacta    3240
ttagtcctat tatgggatac tctactccgt ggagatactt agattttaat gctttgaatt    3300 tgttttttc accactagag tttcagcact taattgagaa ttatggcagt atagctccag     3360
atgctttaac tgtaactatt tcagaaattg ctgttaaaga tgttacagac aaaacaggag    3420
gaggtgtgca agtaactgac agcaccacag gacgtttgtg tatgttagtg gaccatgaat    3480
ataagtaccc atatgtgctg ggtcagggac aagacacatt agctccagaa ctgcctattt    3540
gggtgtactt tcctccccag tatgcttact aacagtagg tgaagtaaac acacaaggag     3600
tttcaggaga cagcaaaaaa ttggctagtg aagaatcagc tttttatgtt ttggaacaca    3660
gctcctttca acttttaggt acaggtgct ctgctacaat gtcctataaa tttccagccg     3720
tgcccccaga aaacttagag ggctgcagtc agcatttta tgaaatgtac aaccccctgt     3780
atggttctcg tttaggagtg cctgacacat taggagggga ccctaaattt agatcattaa    3840
cacacgagga ccacgcaatt cagccacaaa actttatgcc tgggccactg attaactcag    3900
tgtctaccaa agaaggagac acctctaata caggtgctgg aaaagccctt acggggctta    3960
gtactggcac tagtcaaagc accagaattt ccctgcgccc aggtccagtg tctcagccat    4020
accatcactg ggacactgat aaatatgtaa caggaataaa tgccatctca catgacaaa    4080 ccacttatgg aaatgctgaa gacaaagagt atcagcaagg ggtaggaagg tttccaaatg    4140
aaaaagaaca acttaagcag ttacaagggc taaacatgca cacatacttt cctaataaag    4200
gtacccaaca atacacagat caaattgaaa gaccttaat ggtgggctct gtgtggaaca    4260
gaagagctct tcactatgaa agtcagttat ggagtaaaat ccctaactta gatgatagtt    4320
ttaaaactca atttgcagcg ttaggcgggt ggggattgca ccaaccaccc cctcaaatat    4380
ttttaaaaat actaccgcaa agtgggccca ttggaggtat aaatccatg ggaattacta     4440 ctttagtcca gtatgctgta ggaattatga cagtcactat gacatttaaa ttgggacctc    4500
gaaaagccac tggaaggtgg aatcctcaac ctggagttta ccctcctcat gcagctggtc    4560
atttaccata tgtactgtat gaccccacag ctacagatgc aaagcaacac cacagacacg    4620
gatatgaaaa gcctgaagaa ttgtggactg ccaaaagccg tgtgcaccca ctgtaaacat    4680 tcccaccgt gtcctaagcc aggaaccgtc acccaccgtc cacctgtacc gcctagatta    4740
tatgtgcccc ctcctgtacc cagtaggcaa ccatctgtaa aagatacaga cgctgtagaa    4800
tataaattgc taactagata tgaacaacat gtaattagaa tgcttagatt atgtaatatg    4860
tacacaaatt tggaaaaata aaagcctaaa ataataact aatagtgtat gttgctttaa     4920
aaattttaaa aagaagacac caaatcagat gccgccggtc gccgccggta ggcgggactt    4980
ccggttcaag atggcggaca gttacgtcat ttcctgt                            5017
```

<210> SEQ ID NO 134
<211> LENGTH: 50
<212> TYPE: DNA
<213> ORGANISM: Erythrovirus B19

```
<400> SEQUENCE: 134
tcagcagcag tggtggtgaa agctctgaag aactcagtga aagcagcttt          50

<210> SEQ ID NO 135
<211> LENGTH: 18
<212> TYPE: DNA
<213> ORGANISM: Erythrovirus B19

<400> SEQUENCE: 135
cttaaaaact ctccagac                                             18

<210> SEQ ID NO 136
<211> LENGTH: 17
<212> TYPE: DNA
<213> ORGANISM: Erythrovirus B19

<400> SEQUENCE: 136
tgaaaccccg cgctcta                                              17

<210> SEQ ID NO 137
<211> LENGTH: 21
<212> TYPE: DNA
<213> ORGANISM: Erythrovirus B19

<400> SEQUENCE: 137
aactaacagt tcacgaaact g                                         21

<210> SEQ ID NO 138
<211> LENGTH: 23
<212> TYPE: DNA
<213> ORGANISM: Erythrovirus B19

<400> SEQUENCE: 138
tccccgggac cagttcagga gaa                                       23

<210> SEQ ID NO 139
<211> LENGTH: 17
<212> TYPE: DNA
<213> ORGANISM: Erythrovirus B19

<400> SEQUENCE: 139
tcagcagcag tggtggt                                              17

<210> SEQ ID NO 140
<211> LENGTH: 17
<212> TYPE: DNA
<213> ORGANISM: Erythrovirus B19

<400> SEQUENCE: 140
tagagcgcgg ggtttca                                              17

<210> SEQ ID NO 141
<211> LENGTH: 34
<212> TYPE: DNA
<213> ORGANISM: Erythrovirus B19

<400> SEQUENCE: 141
tgaaagctct gaagaactca gtgaaagcag cttt                           34

<210> SEQ ID NO 142
<211> LENGTH: 18
<212> TYPE: DNA
```

```
<213> ORGANISM: Erythrovirus B19

<400> SEQUENCE: 142
aatgcagatg ccctccac                                              18

<210> SEQ ID NO 143
<211> LENGTH: 29
<212> TYPE: DNA
<213> ORGANISM: Erythrovirus B19

<400> SEQUENCE: 143
tcagcagcag tggtggtgaa agctctgaa                                  29

<210> SEQ ID NO 144
<211> LENGTH: 15
<212> TYPE: DNA
<213> ORGANISM: Erythrovirus B19

<400> SEQUENCE: 144
tgttccaggc gcctg                                                 15

<210> SEQ ID NO 145
<211> LENGTH: 18
<212> TYPE: DNA
<213> ORGANISM: Erythrovirus B19

<400> SEQUENCE: 145
cacagctaca gatgcaaa                                              18

<210> SEQ ID NO 146
<211> LENGTH: 16
<212> TYPE: DNA
<213> ORGANISM: Erythrovirus B19

<400> SEQUENCE: 146
ggtgcacacg gctttt                                                16

<210> SEQ ID NO 147
<211> LENGTH: 30
<212> TYPE: DNA
<213> ORGANISM: Erythrovirus B19

<400> SEQUENCE: 147
tgtccacaat tcttcaggct tttcatatcc                                 30

<210> SEQ ID NO 148
<211> LENGTH: 30
<212> TYPE: DNA
<213> ORGANISM: Erythrovirus B19

<400> SEQUENCE: 148
tggatatgaa aagcctgaag tattgtggac                                 30

<210> SEQ ID NO 149
<211> LENGTH: 20
<212> TYPE: DNA
<213> ORGANISM: Erythrovirus B19

<400> SEQUENCE: 149
ggtcatttac catatgtact                                            20

<210> SEQ ID NO 150
<211> LENGTH: 30
```

```
<212> TYPE: DNA
<213> ORGANISM: Artificial
<220> FEATURE:
<223> OTHER INFORMATION: Description of Artificial Sequence: synthetic
      oligonucleotide; n is a universal base analogue
<220> FEATURE:
<221> NAME/KEY: misc_feature
<222> LOCATION: (16)..(16)
<223> OTHER INFORMATION: Description of Artificial Sequence: synthetic
      oligonucleotide; n is a universal base analogue

<400> SEQUENCE: 150
agctacagat gcaaancaac accacagaca                                    30

<210> SEQ ID NO 151
<211> LENGTH: 23
<212> TYPE: DNA
<213> ORGANISM: Erythrovirus B19

<400> SEQUENCE: 151
gaaaactttc catttaatga tgt                                           23

<210> SEQ ID NO 152
<211> LENGTH: 20
<212> TYPE: DNA
<213> ORGANISM: Erythrovirus B19

<400> SEQUENCE: 152 atttttttgat ctaccctggt                                              20

<210> SEQ ID NO 153
<211> LENGTH: 20
<212> TYPE: DNA
<213> ORGANISM: Erythrovirus B19

<400> SEQUENCE: 153
ttggtggtct gggatgaagg                                               20

<210> SEQ ID NO 154
<211> LENGTH: 19
<212> TYPE: DNA
<213> ORGANISM: Erythrovirus B19

<400> SEQUENCE: 154
ttttatgggc cgccaagta                                                19

<210> SEQ ID NO 155
<211> LENGTH: 20
<212> TYPE: DNA
<213> ORGANISM: Erythrovirus B19

<400> SEQUENCE: 155
ttcatcccag accaccaagg                                               20

<210> SEQ ID NO 156
<211> LENGTH: 29
<212> TYPE: DNA
<213> ORGANISM: Erythrovirus B19

<400> SEQUENCE: 156
atggctattg ctaaaactgt tccagtgta                                     29

<210> SEQ ID NO 157
<211> LENGTH: 34
<212> TYPE: DNA
```

```
<213> ORGANISM: Erythrovirus B19

<400> SEQUENCE: 157
tggaataatg aaaactttcc atttaatgat gtag                              34

<210> SEQ ID NO 158
<211> LENGTH: 26
<212> TYPE: DNA
<213> ORGANISM: Erythrovirus B19

<400> SEQUENCE: 158
caatggccat tgctaaaagt gttcca                                       26
```